(12) United States Patent
Cass et al.

(10) Patent No.: US 11,131,663 B2
(45) Date of Patent: Sep. 28, 2021

(54) ANALYTE DETECTION METHOD

(71) Applicant: IMPERIAL COLLEGE INNOVATIONS LIMITED, London (GB)

(72) Inventors: Anthony Edward George Cass, London (GB); Joshua Benno Edel, London (GB); Jasmine Y. Y. Sze, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 0 days.

(21) Appl. No.: 16/604,293

(22) PCT Filed: Apr. 10, 2018

(86) PCT No.: PCT/GB2018/050956
§ 371 (c)(1),
(2) Date: Oct. 10, 2019

(87) PCT Pub. No.: WO2018/189530
PCT Pub. Date: Oct. 18, 2018

(65) Prior Publication Data
US 2020/0041497 A1 Feb. 6, 2020

(30) Foreign Application Priority Data

Apr. 10, 2017 (GB) ..................................... 1705764

(51) Int. Cl.
| | |
|---|---|
| *A61K 48/00* | (2006.01) |
| *C07H 21/02* | (2006.01) |
| *G01N 33/53* | (2006.01) |
| *G01N 33/487* | (2006.01) |
| *C12N 15/115* | (2010.01) |

(52) U.S. Cl.
CPC ....... *G01N 33/5308* (2013.01); *C12N 15/115* (2013.01); *G01N 33/487* (2013.01); *C12N 2310/16* (2013.01)

(58) Field of Classification Search
CPC .......................... C12N 2310/16; C12N 15/113
See application file for complete search history.

(56) References Cited

U.S. PATENT DOCUMENTS

| | | |
|---|---|---|
| 2007/0166741 A1 | 7/2007 | Heil |
| 2010/0021899 A1 | 1/2010 | Ikebukuro et al. |
| 2014/0246317 A1 | 9/2014 | Mayer et al. |
| 2015/0080242 A1 | 3/2015 | Chen et al. |
| 2015/0354001 A1 | 12/2015 | Porath et al. |
| 2016/0053300 A1 | 2/2016 | Maglia et al. |

FOREIGN PATENT DOCUMENTS

| | | | |
|---|---|---|---|
| WO | 2013016280 | 1/2013 | |
| WO | 2013121201 | 8/2013 | |
| WO | WO 2014/160192 A1 * | 10/2014 | ......... C12N 2310/16 |
| WO | 2015121394 | 8/2015 | |

OTHER PUBLICATIONS

Bell et al. (J Am Chem Soc, 2015, 137(5), 2035-2041).*
Actis et al. (Biosensors and Bioelectronics, 26, 2011, 4503-4507).*
Narendran et al., Biotex, 2012, 1 page).*
Bi, Wenjing, et al. "DNA-templated aptamer probe for identification of target proteins." Analytical chemistry 89.7 (2017): 4071-4076.
Singh, Seema, et al. "A quantum dot—MUC1 aptamer conjugate for targeted delivery of protoporphyrin IX and specific photokilling of cancer cells through ROS generation." Integrative Biology 8.10 (2016): 1040-1048.
Ogasawara, Daisuke, et al. "Detection system based on the conformational change in an aptamer and its application to simple bound/free separation." Biosensors and Bioelectronics 24.5 (2009): 1372-1376.
Abe, Koichi, et al. "Aptameric sensors based on structural change for diagnosis." Faraday discussions 149 (2011): 93-105.
Thomson, Karen, et al. "Preliminary nanopore cheminformatics analysis of aptamer-target binding strength." BMC bioinformatics. vol. 8. No. 7. BioMed Central, 2007.
Arnaut, Vera, Martin Langecker, and Friedrich C. Simmel. "Nanopore Force Spectroscopy of Aptamer-Ligand Complexes." Biophysical journal 105.5 (2013): 1199-1207.
Yang, Zhugen, et al. "A novel immobilization strategy for electrochemical detection of cancer biomarkers: DNA-directed immobilization of aptamer sensors for sensitive detection of prostate specific antigens." Analyst 140.8 (2015): 2628-2633.
Huang, Yong, et al. "Attomolar detection of proteins via cascade strand-displacement amplification and polystyrene nanoparticle enhancement in fluorescence polarization aptasensors." Analytical chemistry 87.16 (2015): 8107-8114.
Lin, Xiaoyan, Aleksandar P. Ivanov, and Joshua B. Edel. "Selective single molecule nanopore sensing of proteins using DNA aptamer-functionalised gold nanoparticles." Chemical science 8.5 (2017): 3905-3912.
Rauf, Sana, et al. "Label-free nanopore biosensor for rapid and highly sensitive cocaine detection in complex biological fluids." ACS sensors 2.2 (2016): 227-234.
Gu, Li-Qun, and Ji Wook Shim. "Single molecule sensing by nanopores and nanopore devices." Analyst 135.3 (2010): 441-451.
Sze, Jasmine YY, et al. "Single molecule multiplexed nanopore protein screening in human serum using aptamer modified DNA carriers." Nature communications 8.1 (2017): 1552.

(Continued)

*Primary Examiner* — Amy H Bowman
(74) *Attorney, Agent, or Firm* — Meunier Carlin & Curfman LLC

(57) ABSTRACT

THE present application relates to a method of detecting one or more analytes in a sample, the method comprising (a) providing a carrier nucleic acid molecule with at least one single-stranded region; (b) providing one or more aptamers specific for the analyte, wherein the aptamers additionally comprise a single-stranded portion complementary to at least one single-stranded region on the carrier nucleic acid; (c) contacting the carrier nucleic acid and one or more aptamers with the sample, forming a carrier nucleic acid/N aptamer/analyte complex, and; (d) detecting the presence of the carrier nucleic acid/aptamer/analyte complex.

10 Claims, 41 Drawing Sheets

Specification includes a Sequence Listing.

(56) References Cited

OTHER PUBLICATIONS

Lv et al. "A label-free fluorescence assay for thrombin based on aptamer exonuclease protection and exonuclease III-assisted recycling amplification-responsive cascade zinc(II)-protoporphyrin IX/G-quadruplex supramolecular fluorescent labels", Analyst, 2014, 139, 2583-2588.
Bell, et al. "Specific Protein Detection Using Designed DNA Carriers and Nanopores", J. Am. Chem. Soc., 2015, 137, 2035-2041.
Dekker, Cees. "Solid-state nanopores." Nature nanotechnology 2.4 (2007): 209.
Miles, Benjamin N., et al. "Single molecule sensing with solid-state nanopores: novel materials, methods, and applications." Chemical Society Reviews 42.1 (2013): 15-28.
Shi et al. (2017), 'Nanopore Sensing' Anal. Chem. 2017, 89, 157-188.
Howorka, Stefan, and Zuzanna S. Siwy. "Nanopore analytics: sensing of single molecules." Chem. Soc. Rev., 2009, 38, 2360-2384.
Meller, Amit, Lucas Nivon, and Daniel Branton. "Voltage-driven DNA translocations through a nanopore." Physical Review Letters 86.15 (2001): 3435.
Li, Jiali, et al. "DNA molecules and configurations in a solid-state nanopore microscope." Nature materials 2.9 (2003): 611.
Storm, Arnold J., et al. "Fast DNA translocation through a solid-state nanopore." Nano letters 5.7 (2005): 1193-1197.
Kasianowicz, John J., et al. "Characterization of individual polynucleotide molecules using a membrane channel." Proceedings of the National Academy of Sciences 93.24 (1996): 13770-13773.
Plesa, Calin, et al. "Fast translocation of proteins through solid state nanopores." Nano letters 13.2 (2013): 658-663.
Li, Wenhong, et al. "Single protein molecule detection by glass nanopores." ACS nano 7.5 (2013): 4129-4134.
Wanunu, Meni, et al. "Rapid electronic detection of probe-specific microRNAs using thin nanopore sensors." Nature nanotechnology 5.11 (2010): 807.
Gu, Li-Qun, et al. "Stochastic sensing of organic analytes by a pore-forming protein containing a molecular adapter." Nature 398.6729 (1999): 686.
Maglia, Giovanni, et al. "DNA strands from denatured duplexes are translocated through engineered protein nanopores at alkaline pH." Nano letters 9.11 (2009): 3831-3836.
Oukhaled, G., et al. "Unfolding of proteins and long transient conformations detected by single nanopore recording." Physical review letters 98.15 (2007): 158101.
Rodriguez-Larrea, David, and Hagan Bayley. "Multistep protein unfolding during nanopore translocation." Nature nanotechnology 8.4 (2013): 288.
Rosen, Christian B., David Rodriguez-Larrea, and Hagan Bayley. "Single-molecule site-specific detection of protein phosphorylation with a nanopore." Nature biotechnology 32.2 (2014): 179.
Nivala, Jeff, Douglas B. Marks, and Mark Akeson. "Unfoldase-mediated protein translocation through an α-hemolysin nanopore." Nature biotechnology 31.3 (2013): 247.
Nivala, Jeff, et al. "Discrimination among protein variants using an unfoldase-coupled nanopore." ACS nano 8.12 (2014): 12365-12375.
Storm, A. J., et al. "Fabrication of solid-state nanopores with single-nanometre precision." Nature materials 2.8 (2003): 537.
Ayub, Mariam, et al. "Precise electrochemical fabrication of sub-20 nm solid-state nanopores for single-molecule biosensing." Journal of Physics: Condensed Matter 22.45 (2010): 454128.
Kowalczyk, Stefan W., Adam R. Hall, and Cees Dekker. "Detection of local protein structures along DNA using solid-state nanopores." Nano letters 10.1 (2009): 324-328.
Spiering, Andre, et al. "Nanopore translocation dynamics of a single DNA-bound protein." Nano letters 11.7 (2011): 2978-2982.
Squires, Allison, Evrim Atas, and Amit Meller. "Nanopore sensing of individual transcription factors bound to DNA." Scientific reports 5 (2015): 11643.
Smeets, R. M. M., et al. "Translocation of RecA-coated double-stranded DNA through solid-state nanopores." Nano letters 9.9 (2008): 3089-3095.
Yusko, Erik C., et al. "Controlling protein translocation through nanopores with bio-inspired fluid walls." Nature nanotechnology 6.4 (2011): 253.
Yusko, Erik C., et al. "Real-time shape approximation and fingerprinting of single proteins using a nanopore." Nature nanotechnology 12.4 (2017): 360.
Singer, Alon, et al. "Nanopore based sequence specific detection of duplex DNA for genomic profiling." Nano letters 10.2 (2010): 738-742.
Tuerk, Craig, and Larry Gold. "Systematic evolution of ligands by exponential enrichment: RNA ligands to bacteriophage T4 DNA polymerase." science 249.4968 (1990): 505-510.
Ellington, Andrew D., and Jack W. Szostak. "In vitro selection of RNA molecules that bind specific ligands." nature 346.6287 (1990): 818.
Smith, Joshua E., et al. "Aptamer-conjugated nanoparticles for the collection and detection of multiple cancer cells." Analytical Chemistry 79.8 (2007): 3075-3082.
Kelly, Jennifer A., Juli Feigon, and Todd O. Yeates. "Reconciliation of the X-ray and NMR structures of the thrombin-binding aptamer d(GGTTGGTGTGGTTGG)." (1996): 417-422.
Russo Krauss, Irene, et al. "Thrombin-aptamer recognition: a revealed ambiguity." Nucleic acids research 39.17 (2011): 7858-7867.
Pasternak, Anna, et al. "Improved thrombin binding aptamer by incorporation of a single unlocked nucleic acid monomer." Nucleic acids research 39.3 (2010): 1155-1164.
Russo Krauss, Irene, et al. "High-resolution structures of two complexes between thrombin and thrombin-binding aptamer shed light on the role of cations in the aptamer inhibitory activity." Nucleic acids research 40.16 (2012): 8119-8128.
Le, Thao T., Orada Chumphukam, and Anthony EG Cass. "Determination of minimal sequence for binding of an aptamer. A comparison of truncation and hybridization inhibition methods." RSC Advances 4.88 (2014): 47227-47233.
Chumphukam, Orada, Thao Le, and Anthony Cass. "High efficiency acetylcholinesterase immobilization on DNA aptamer modified surfaces." Molecules 19.4 (2014): 4986-4996.
Singer, Alon, et al. "Electronic barcoding of a viral gene at the single-molecule level." Nano letters 12.3 (2012): 1722-1728.
Kong, Jinglin, Nicholas AW Bell, and Ulrich F. Keyser. "Quantifying nanomolar protein concentrations using designed DNA carriers and solid-state nanopores." Nano letters 16.6 (2016): 3557-3562.
Bell, Nicholas AW, and Ulrich F. Keyser. "Digitally encoded DNA nanostructures for multiplexed, single-molecule protein sensing with nanopores." Nature nanotechnology 11.7 (2016): 645.
Fanzio, Paola, et al. "Selective protein detection with a dsLNA-functionalized nanopore." Biosensors and Bioelectronics 64 (2015): 219-226.
Wen, Shuang, et al. "Highly sensitive and selective DNA-based detection of mercury (II) with α-hemolysin nanopore." Journal of the American Chemical Society 133.45 (2011): 18312-18317.
Kong, Jinglin, Jinbo Zhu, and Ulrich F. Keyser. "Single molecule based SNP detection using designed DNA carriers and solid-state nanopores." Chemical Communications 53.2 (2017): 436-439.
International Search Report and Written Opinion dated Aug. 2, 2018, from International Application No. PCT/GB2018/050956, 18 pages.
Search Report under Section 17(5) dated Jan. 18, 2018, issued in related GB Application No. GB1705764.7, 4 pages.

* cited by examiner

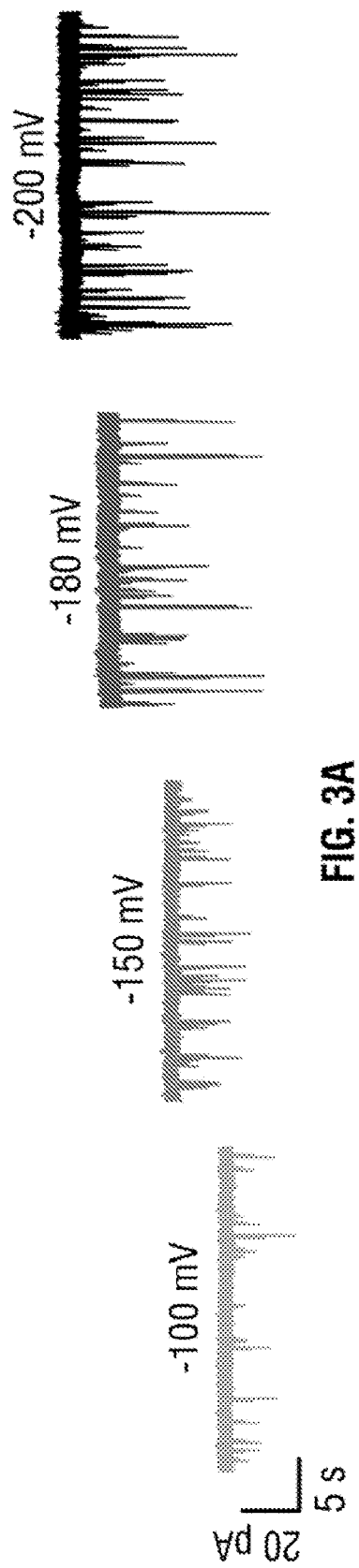
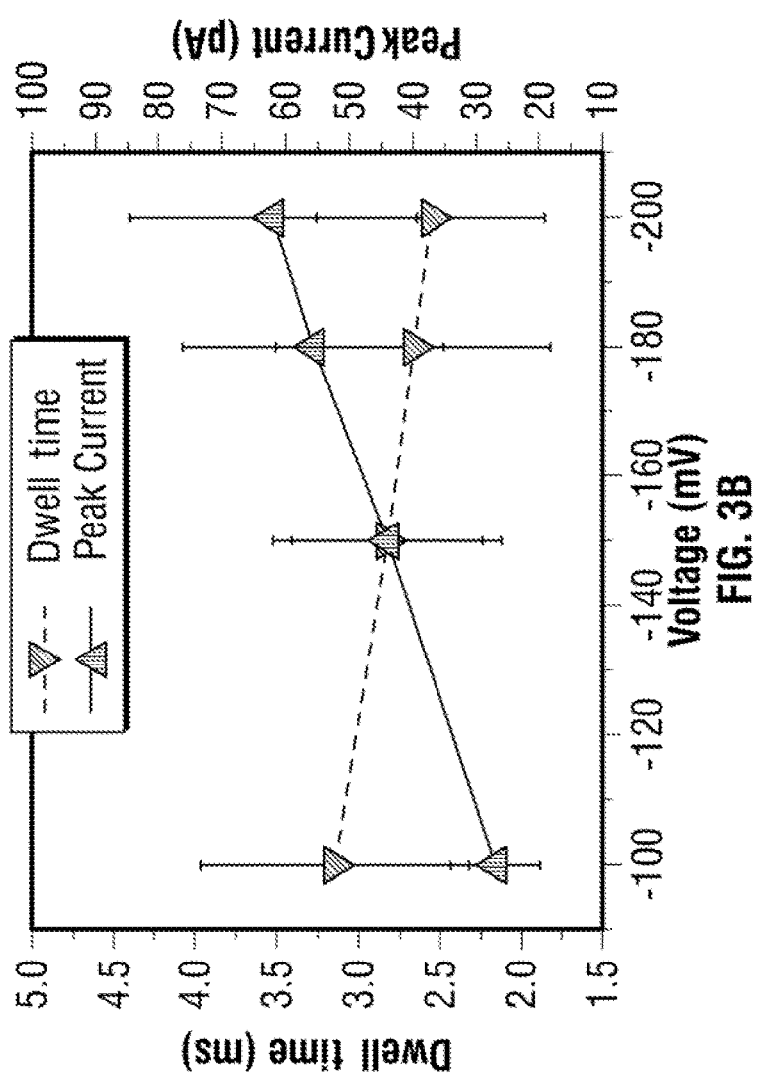
FIG. 3A
FIG. 3B (i) (ii) (iii)

ANALYTE DETECTION METHOD

CROSS REFERENCE TO RELATED APPLICATIONS

This Application is a national stage application filed under 35 U.S.C. § 371 of PCT/GB2018/050956 filed Apr. 10, 2018, which claims priority to Great Britain Application No. 1705764.7, filed on Apr. 10, 2017, applications which are incorporated herein by reference in their entirety.

FIELD OF INVENTION

The present invention provides methods for the detection of analytes, including but not limited to biological molecules such as proteins or peptides, via the use of aptamers. The methods find particular utility in detecting analytes in complex biological samples such as serum or plasma. In preferred embodiments the methods described provide for the multiplexed detection of multiple different biological molecules. In particular, the methods utilise nanopore detection, which relies on monitoring changes in ionic current as molecules pass through the pore under the influence of an applied potential.

BACKGROUND

Measureable changes in the concentration of proteins found in serum as well as other physiological fluids can often be indicative of disease; with early diagnosis allowing the implementation of accurate and effective treatment to prevent disease progression. While current biosensors have demonstrated the ability to identify and quantify proteins, they usually lack the specificity and sensitivity for early stage precision diagnosis in real samples containing many (thousands) of background proteins. Nanopores[1-4] have been proven to be a promising tool for the detection of DNA[5-7], RNA[8], proteins[9-10] and other molecules[8, 11] as they allow the possibility of single molecular level and rare event analysis which is normally masked by ensemble averaging in classical measurement methods. The simple nanopore detection method relies on modulations of the ionic current as molecules pass through the pore under the influence of an applied potential. The change in the ionic current will depend on the presence, location and conformation of a single molecule in the pore.

Direct detection of proteins with biological nanopores is challenging due to the small fixed orifice as well as a well-defined geometry that only allows the passage of a limited number of analytes or folded proteins to pass through. Strategies such as adding a small organic molecule at a specific site have been demonstrated in the α-haemolysin pore i.e. having hydrophobic groups that bind organic molecules[12] or a biotin-labelled chain that can probe biotin-binding proteins[1]. Alternatively the use of denaturing reagents[13-14], high mechanical force with oligonucleotide tethers[15-16] or unfoldase-mediated enzyme[17-18] induce unfolding of protein molecules allowing prompt translocations provide new mechanisms for protein detection. Though the use of biological nanopores have proven successful, there remains a number of limitations with them such as stability issues with an embedded lipid bilayer, non-tuneable pore size and difficulty of multiplex detection in the same nanopore. An alternative to biological nanopores is to use solid state nanopores. They can be fabricated with a high degree of control of pore size[19-20], allowing proteins of various size to translocate through the pore. While nanopores have been shown in the detection of variable size of proteins[10], peptides and DNA binding proteins[21-24], recent results have indicated that the fast translocation speeds of most proteins lead to poor detection limits at typical experimental bandwidths.[9] While advances in the use of high bandwidth amplifiers have led to improvements in resolution, protein translocation selectivity through nanopores still remains a limitation due to the stochastic nature of nanopore sensing.

Challenges still remain in differentiating single protein molecule translocations from nonspecific binding translocations or various interactions between the analytes of a complex mixture. Keyser and co-workers demonstrated the use of a DNA nanotechnology construct, employing a 7.2 kb single stranded DNA (ssDNA) as a carrier hybridised to 190 complimentary oligonucleotides ('staples'). Modification of some of these oligonucleotides with a barcode system created divalent antigen sites on the DNA allowing detection of the corresponding antibodies.[29-31] The disadvantage of this system is the requirement to incubate the whole modified barcode library onto different ssDNA carrier in order to detect multiple antibodies; consequently in order to test more than 10 proteins at a time, extensive engineering and extremely high protein concentrations (>μM) are required to incubate the DNA carrier. Furthermore, only a limited range of proteins could be detected due to the availability of immobilisation or conjugation steps for the antigen to be attached to the sequence. Modification chemistry can lead to unfavourable detection specificity at single molecule level. Their method also utilizes high salt concentrations such as 4 M LiCl to slow down the translocation rate inside the nanopore which hinders most of the protein-target binding.

SUMMARY OF INVENTION

In a first aspect, the present invention provides a method of detecting one or more analytes in a sample, the method comprising:
a. providing a carrier nucleic acid molecule with at least one single-stranded region;
b. providing one or more aptamers specific for the analyte, wherein the aptamers additionally comprise a single-stranded portion complementary to at least one single-stranded region on the carrier nucleic acid;
c. contacting the carrier nucleic acid and one or more aptamers with the sample, forming a carrier nucleic acid/aptamer/analyte complex;
d. detecting the presence of the carrier nucleic acid/aptamer/analyte complex.

Preferably, multiple aptamers specific for different analytes are provided, each analyte-specific aptamer having a single-stranded portion complementary to a different single-stranded region on the same carrier nucleic acid.

In another preferred embodiment, multiple aptamers specific for the same analyte are provided, but with each analyte-specific aptamer having a single-stranded portion complementary to a different single-stranded region on the same carrier nucleic acid. In this embodiment, the aptamers may all have the same analyte-binding portion, differing only in their single-stranded portions. Alternatively, the aptamers may bind the same analyte but have different analyte-binding portions and different single-stranded portions.

In certain preferred embodiments the carrier molecule is either DNA or RNA. In other preferred embodiments, the carrier nucleic acid molecule is either single or double-stranded. Where the carrier nucleic acid molecule is double-stranded, it will have at least one single-stranded region. Typically, the single-stranded regions of a double-stranded nucleic acid molecule take the form of 3' or 5' overhangs, but single stranded sections can be created at any point along the double-stranded molecule.

In yet further preferred embodiments, the at least one aptamer (the first aptamer) comprises a single-stranded portion at least partially complementary to a single-stranded portion of the carrier nucleic acid and partially complementary to the single-stranded portion of an additional aptamer (the second aptamer). In this way, new binding sites are created for aptamers having single-stranded portions that are not complementary to the carrier molecule. In this situation, the second aptamer will have a single-stranded portion complementary to a portion of the single-stranded portion of first aptamer. When both aptamers are present, the second aptamer forms a complex with the carrier nucleic acid via the first aptamer.

The detection of the carrier nucleic acid/aptamer/analyte complex may be by any suitable means. In particularly preferred embodiments, the detection of the carrier nucleic acid/aptamer/analyte complex is by voltage-driven translocation through a nanopore.

Preferably, when detection is achieved by voltage-driven translocation through a nanopore, a change in nanopore conductance versus control indicates the presence of an analyte. More preferably, the location of the change in nanopore conductance versus control in the time frame of translocation is indicative of the position of the aptamer along the carrier nucleic acid. In preferred embodiments, the change in nanopore conductance is an increase in nanopore conductance.

In preferred embodiments when detection is achieved by voltage-driven translocation through a nanopore, the nanopore may be located at the tip of a nanopipette.

In other preferred embodiments detection is achieved by fluorescence detection. In still further preferred embodiments, detection is achieved by confocal microscopy, preferably fluorescence confocal microscopy.

In other preferred embodiments, an additional analyte-specific binding molecule is contacted with the sample, forming a carrier nucleic acid/aptamer/analyte/analyte-specific binding molecule complex. Such an arrangement is sometimes termed a sandwich assay and may be useful where the analyte has a high molecular weight.

In still further embodiments, the detection of particularly low molecular weight analytes is achieved by adding to the sample a known quantity of the analyte conjugated to a high molecular weight label. In the presence of the unlabelled analyte in the sample will cause a change in signal compared to the sample containing only the labelled analyte. In these embodiments the presence of the analyte is therefore indicated by a change in the signal. Such an arrangement is sometimes termed a competitive assay.

Accordingly, in a further aspect of the invention there is provided a method of detecting one or more analytes in a sample, the method comprising:
a. providing a carrier nucleic acid molecule with at least one single-stranded region;
b. providing one or more aptamers specific for the analyte, wherein the aptamers additionally comprise a single-stranded portion complementary to at least one single-stranded region on the carrier nucleic acid;
c. providing a known quantity of the analyte conjugated to a high molecular weight label, forming a known quantity of carrier nucleic acid/aptamer/labelled-analyte complex;
d. contacting the carrier nucleic acid/aptamer/labelled-analyte complex with the sample; and
e. detecting the change of the presence of the carrier nucleic acid/aptamer/labelled-analyte complex.

Preferred embodiments described in respect of the first aspect are also contemplated in respect of the above-described further aspect.

129.7×195.4 Å) (b) Typical current trace (re-filtered to 5 kHz) and individual signatures clearly showing two distinct sub-peaks at (~21-24 pA) and at (~35-57 pA) associated with thrombin and AChE binding respectively. (c) Only the translocation events exhibiting two distinct sub-peak were used for further analysis which is consistent with the fractional position of thrombin (0.2) and AChE (0.8) on the DNA carrier. (d) Current amplitude and dwell time statistics are shown for the total translocation events (contour plot) and the individual sub-peaks obtained at voltages ranging from −180 to −300 mV using a 100 pM analyte in buffer containing 100 mM KCl. The mean peak current was determined via Gaussian fitting and plotted in (e). Importantly both proteins are distinguishable not only by location but also by the current amplitude making it possible to multiplex further and would be extremely useful for further data analysis.

Figure 3C:
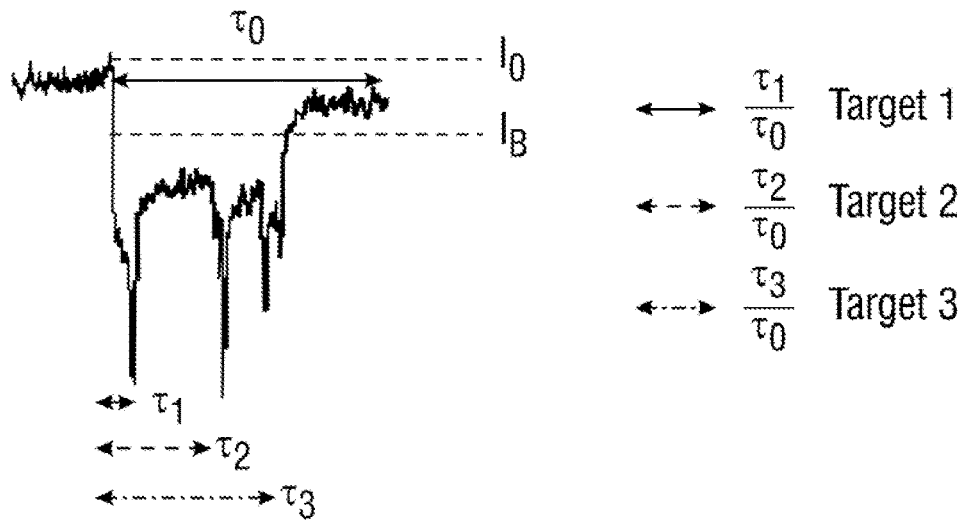
FIG. 3 Statistics on the translocation of a DNA carrier with 3 aptamer targets. In all cases concentration of 100 pM in 100 mM KCl was used and applied voltage was varied between −100 to −200 mV. (a) Typical voltage dependant current-time traces, re-filtered to 5 kHz, are shown. (b) Voltage-dependent relationship between the dwell time and peak current: increasing voltage lead to electrophoretic force exerted on the dsDNA backbone leading to small decrease in dwell time and higher peak currents. (c) A typical translocation event with three distinct spikes highlighting how the ratio of the fractional position calculated. (d) As can be clearly seen, it is possible to differentiate between DNA carriers with 1, 2, and 3 protein targets attached. (N=total no. of events) Population 1, 2 and 3 shows one target with N=611, 44%, two targets with N=505, 36% and three targets with N=274, 20% respectively. Furthermore, the relative location (or fractional position) can be determined for each sub-peak.

FIG. 5 (a) Typical current-time traces are shown for a serial dilution of human serum spiked with 0.1 M KCl at voltages of −250, 0, and +250 mV. A dilution of 1:20 consists of a sufficiently stable baseline to be used in nanopore sensing and was used for further studies (b) DNA carrier with 3 TBA probes were incubated in HS with the current-time traces clearly showing sub-peaks associated with thrombin binding at −250 mV. (c) Similar to FIG. 3, the sub-peaks could easily be distinguished based on location. (d) The current amplitude for all three sub-peaks, obtained at an applied voltage of ~250 mV, −400 mV and −450 mV was determined via Gaussian fitting and were all showing similar trend among the three targets at each voltage dependence.

Figure 2A:
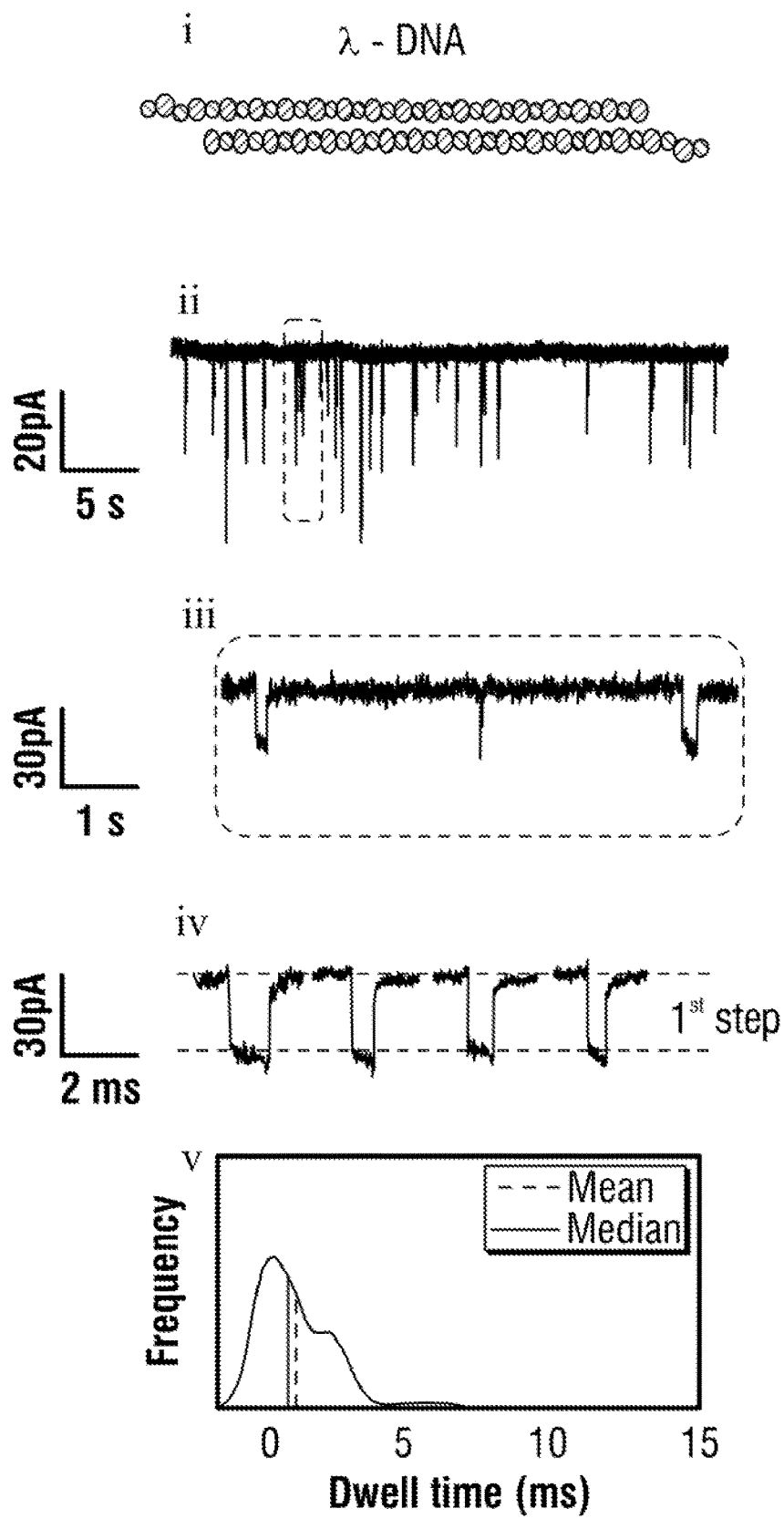
FIG. 2 Schematic of (a) bare λ-DNA, (b) λ-DNA with two aptamer probes and associated thrombin targets, (c) λ-DNA with three aptamer probes and associated thrombin targets. In all cases concentration of 100 μM in 100 mM KCl was used and the voltage was set to −200 mV. All current-time traces were re-filtered to 5 kHz. Typical individual translocation events are shown with the sub-peaks labelled $1^{st}$ step associated to the DNA carrier and $2^{nd}$ step, due to protein binding, superimposed on the signal attributed to the DNA carrier. In all cases the amplitudes from the sub-peaks on average ranged between 45-62 pA depending on nanopore used. (v) Histograms of the representative dwell times are shown for the three conditions with the mean and median represented by a solid and dashed line respectively.
Figure 2B:
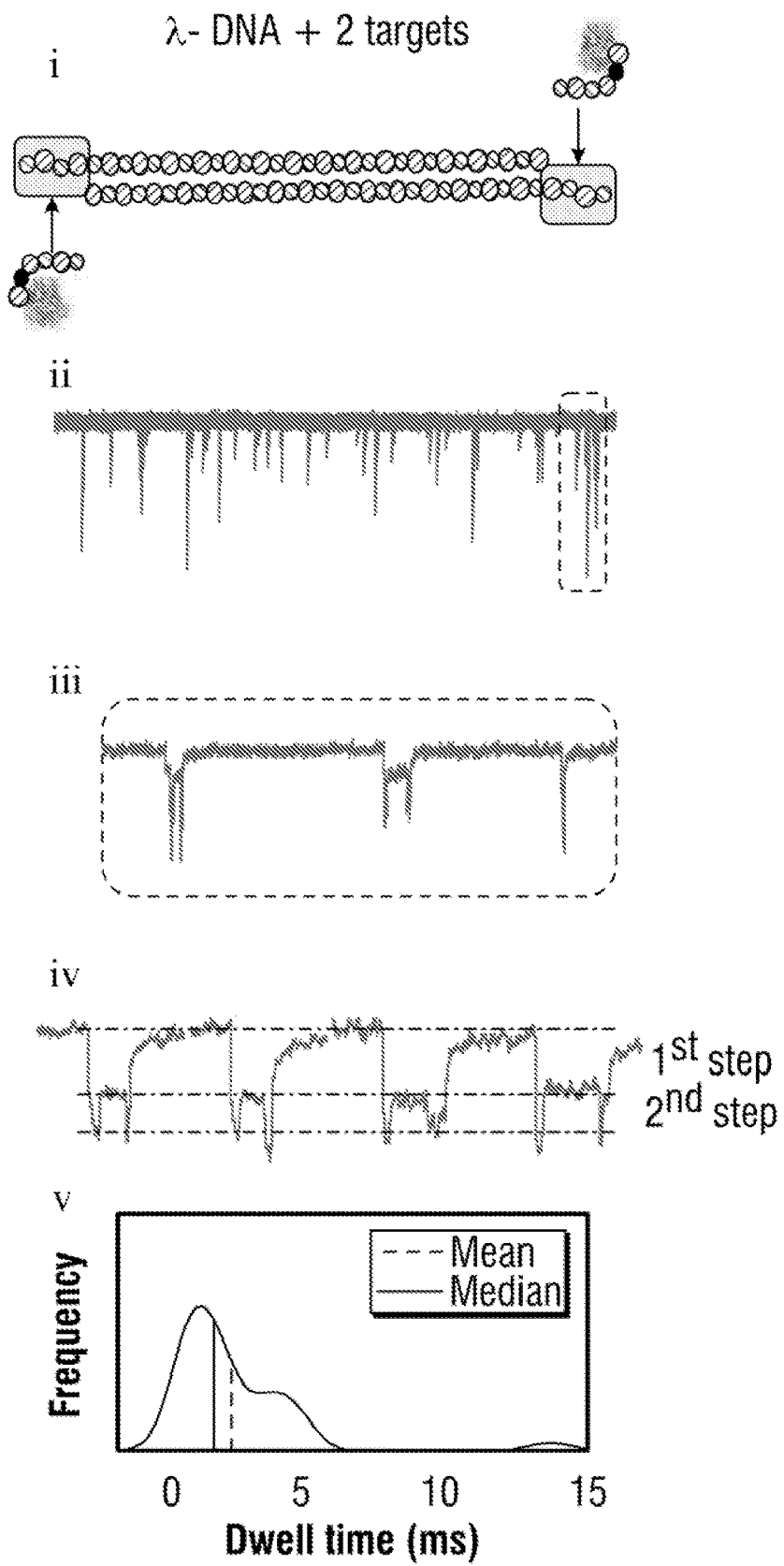
Figure 2C:
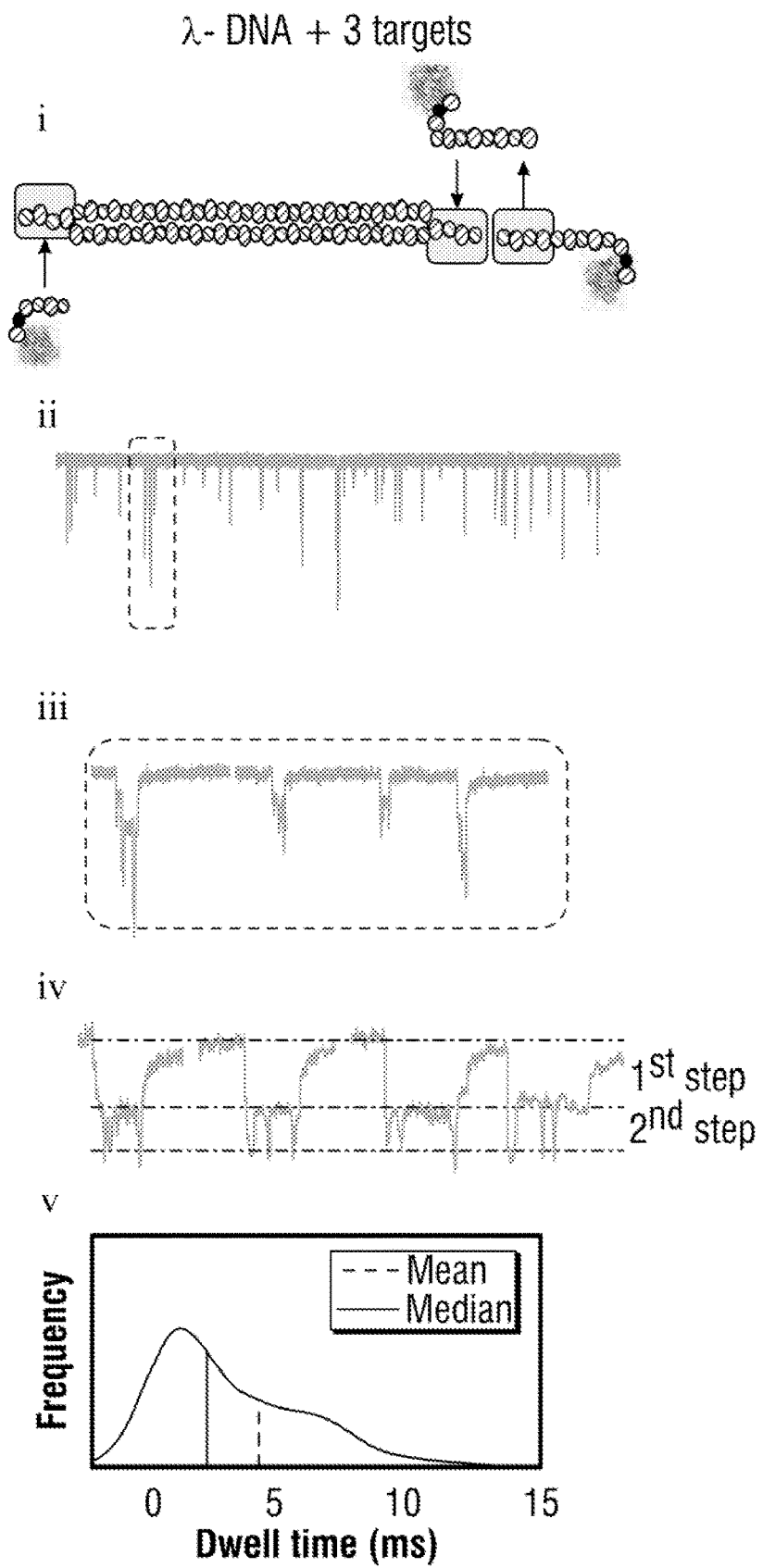
Figure 6A:
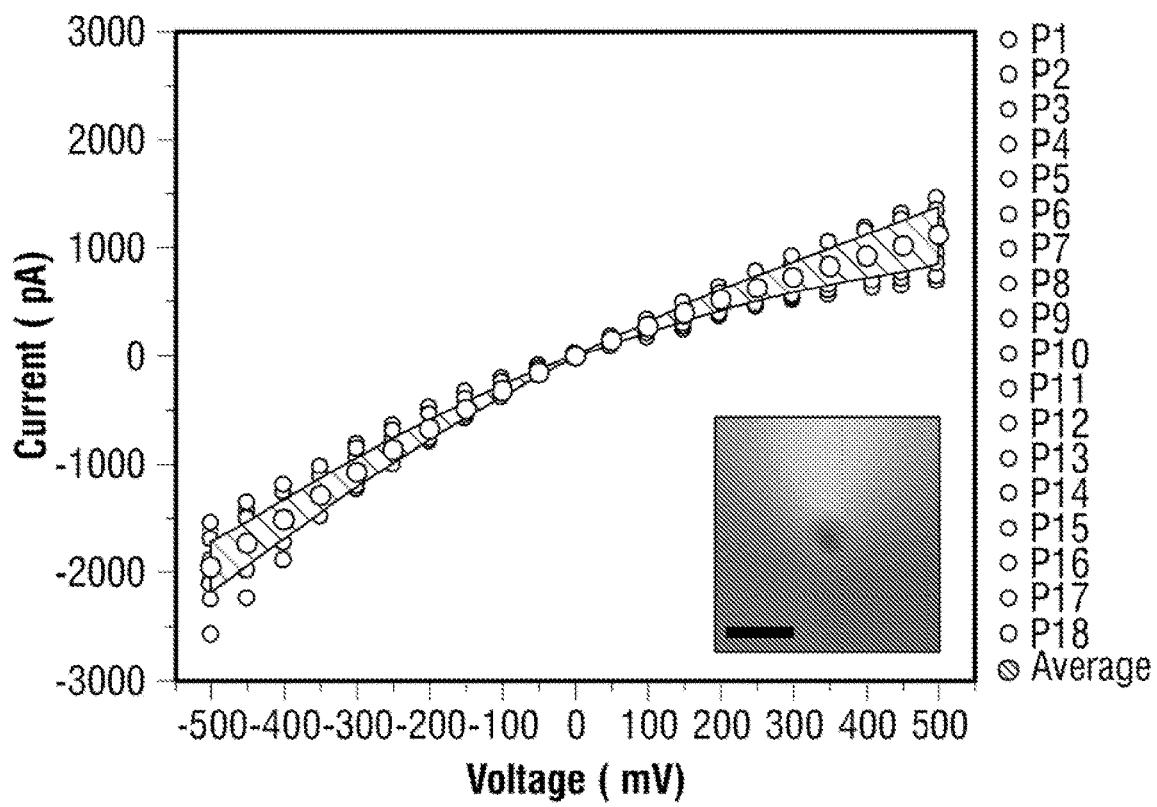
Figure 6B:
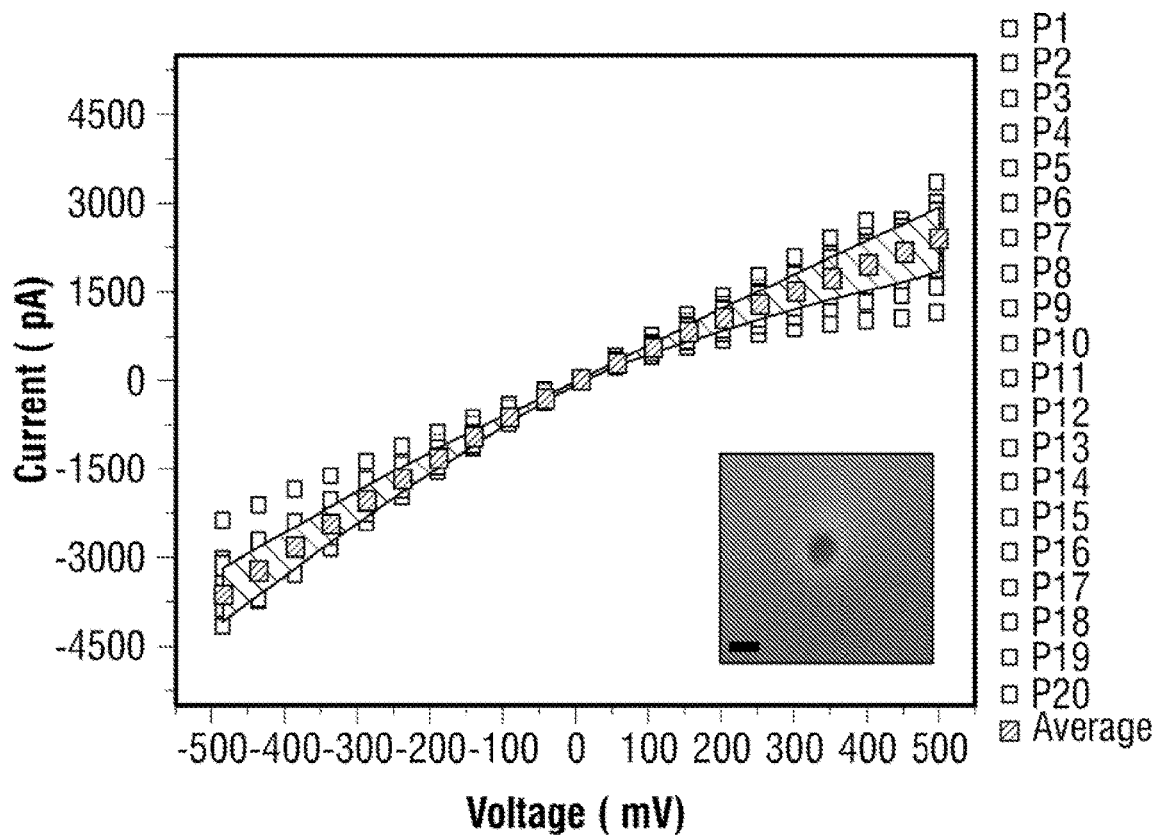

FIG. 6 Electrical characterisation of (a) 18 quartz nanopores with conductance 2.8±0.5 nS and inset show the SEM image of the intended pore diameter~20 nm (with scale bar 50 nm) for experimental performed in FIGS. 2, 3 and 5 (b) 20 quartz nanopore with conductance of 5.8±0.8 nS and inset show the SEM image of the intended pore diameter~42 nm (with scale bar 50 nm) for experimental in FIG. 4 with 0.1 M KCl Tris-EDTA buffer.

Figure 7A:
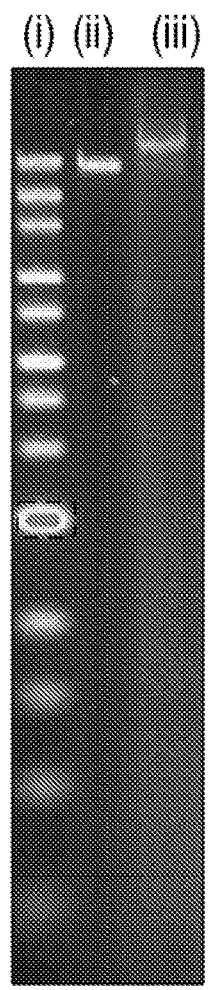
Figure 7B:
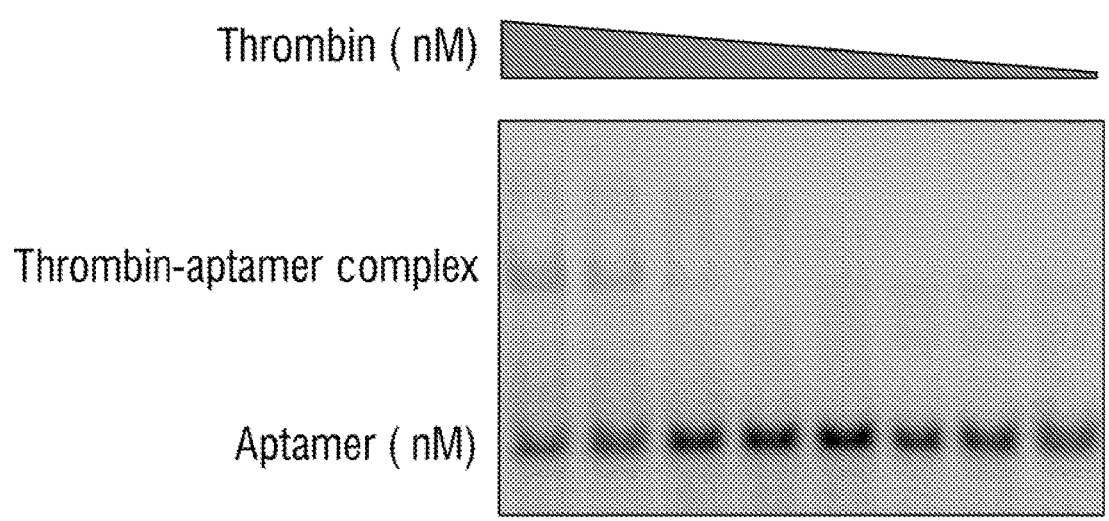

FIG. 7 A 0.65% agarose gel electrophoresis image confirming the detection probes were hybridized to the λ-DNA carrier. Analyte from left to right (i) Extended DNA ladder (ii) bare λ-DNA (iii) λ-DNA with detection probes at 5.7V/cm for 1 hr. The gel was then stained with Sybr Gold and imaged under UV. B Electrophoretic mobility shift assay to show the binding of Thrombin to TBA with binding buffer: 50 mM Tris, 140 mM NaCl, 1 mM $MgCl_2$ Tris-EDTA buffer at pH 7.4 and incubate for 45 minutes. The thrombin concentration used was 500, 250, 150, 100, 75, 50, 20 and 0 nM (from left to right) was incubated with 200 nM of TBA. The sample were then run on a native polyacrylamide gel for 85 minutes at 85V and stained with Sybr Gold and imaged. A shift by the thrombin binding, only observed when correct combination of aptamer and thrombin binds.

Figure 8A:
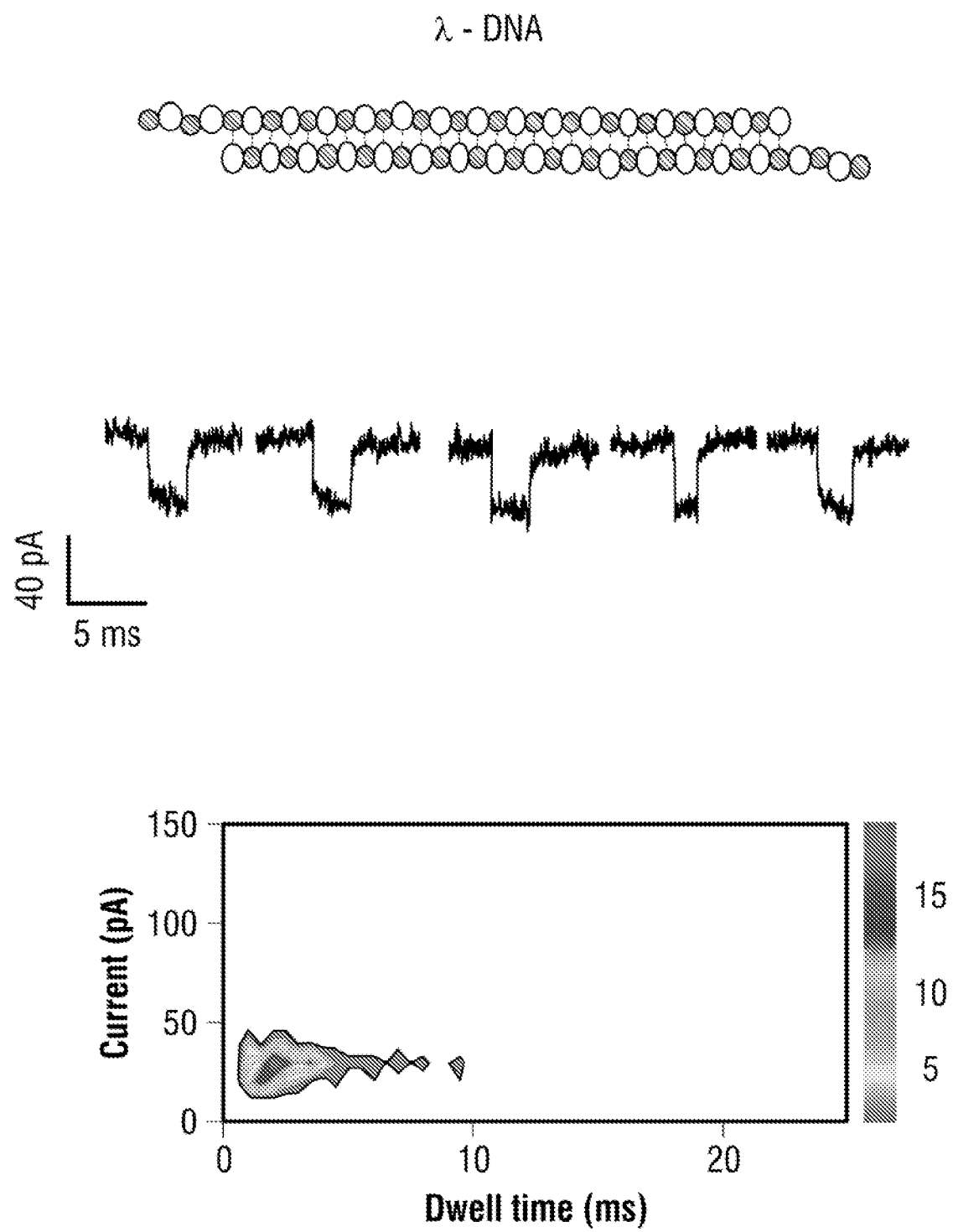
Figure 8B:
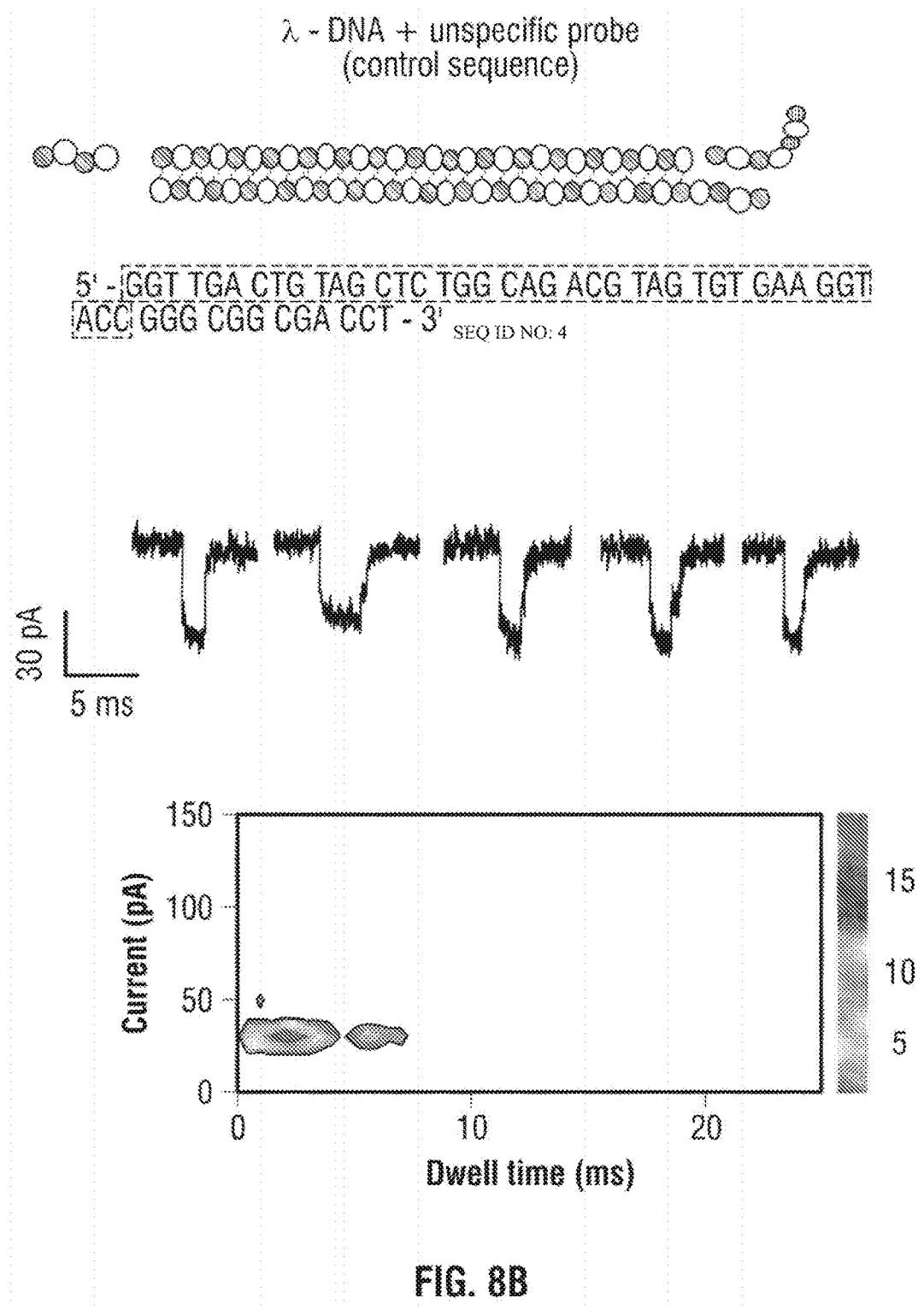
Figure 8C:
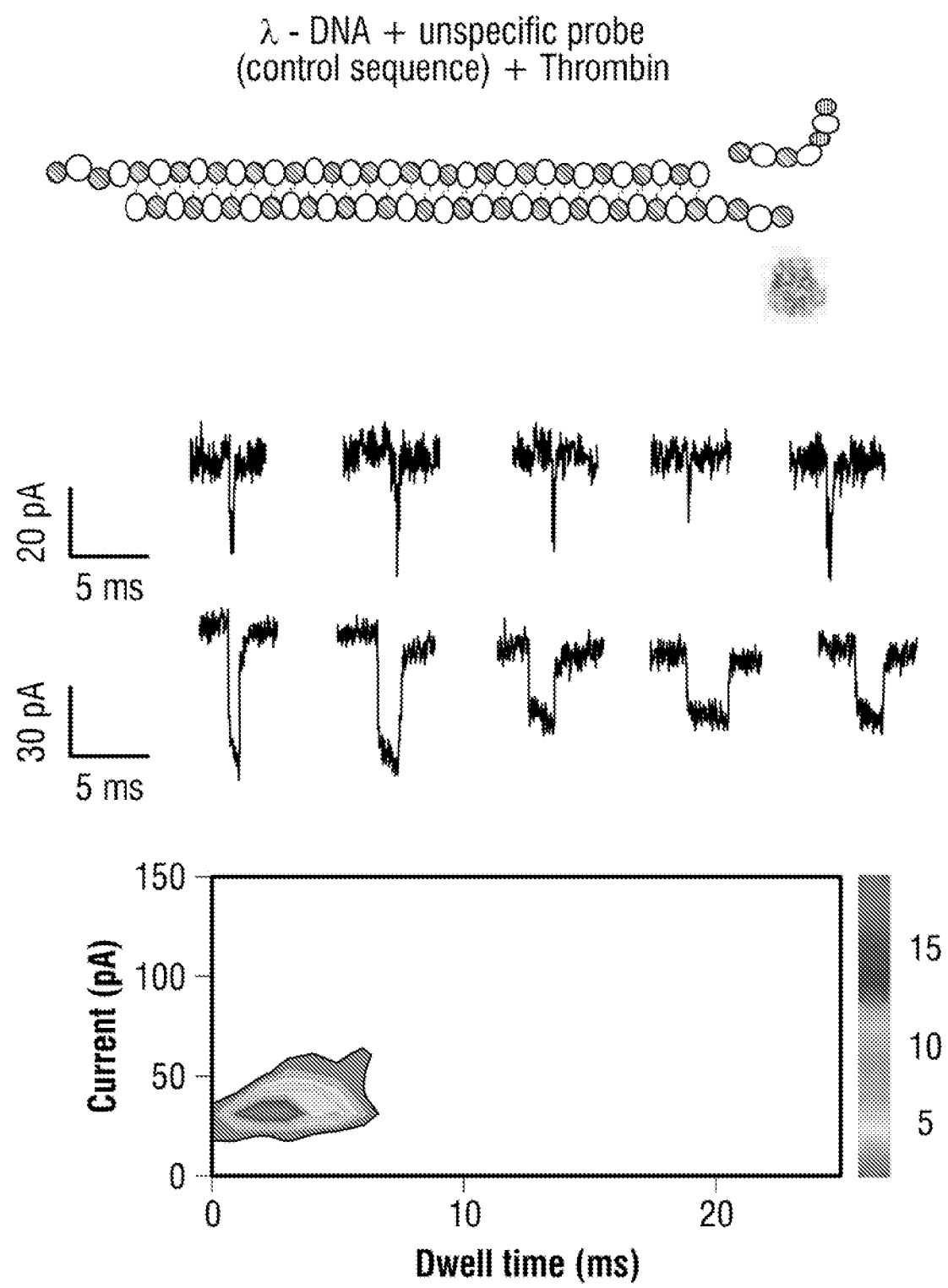

FIG. 8: Table 1 Control experiments using non-specific aptamers bound to the DNA carrier. (a) unmodified λ-DNA, (b) aptamer modified λ-DNA and (c) λ-DNA+non-specific probe+thrombin. In all cases the DNA carrier concentration was 100 pM and no sub-peaks were observed (as shown in FIG. 2) with exception of folded DNA.

FIG. 9: (a) Optical detection of the carrier/aptamer/analyte complex. i) Carrier only; due to no fluorophore on the carrier/aptamer complex, only electrical signal was observed. ii) Protein only, streptavidin labeled with Atto 488; due to the small and fast streptavidin translocation, only optical signal was observed. iii) Carrier-protein complex; both electrical and optical observed when streptavidin is binding to the aptamer/DNA carrier forming DNA-protein complexes. (b) Typical traces from both optical and electrical signals, with synchronized detection was highlighted in pale pink.

FIG. 10: Current-time trace and statistics for sensing proteins bound to a modified carrier. Translocation and statistics for (a) 100 pM of unmodified λ-DNA, (b) 100 pM aptamer modified λ-DNA (1:1 ratio after filtration), (c) 100 pM aptamer modified λ-DNA with two probes for the detection of thrombin (1.6 nM each), (d) 100 pM aptamer modified λ-DNA with three probes for the detection of three thrombin targets (1.6 nM each). All experiments were performed in 100 mM KCl and at a voltage of −200 mV, taken using 4 different nanopipettes for each sample and re-filtered to 5 kHz. Typical individual translocation events are shown with the contribution due to the DNA carrier labelled as "1st step" and the protein contribution labelled as "2nd step". Scatter plots shown in (iv) clearly indicate binding of protein due to the substantial increase in translocation times and current blockades and corresponding sub-peaks as shown in (iii).

FIG. 11: DNA carrier with 3 aptamer targets. In all cases a concentration of 100 pM in 100 mM KCl was used at an applied voltage ranging between −100 to −200 mV. (a) Typical voltage dependant current-time trace, re-filtered to 5 kHz, is shown. (b) Voltage-dependent relationship between the dwell time and peak current: increasing voltage lead to electrophoretic force exerted on the dsDNA backbone leading to small decrease in dwell time and higher peak currents. (c) A typical translocation event with three distinct sub-peaks is shown with a description of how the fraction position (i.e., relative location) of the bound protein is determined. (d) As can be clearly seen, it is possible to differentiate between DNA carriers with 1, 2 and 3 protein targets attached. N=total number of protein events within the same carrier.

FIG. 12: Nanopore sensing of multiple protein targets on a single DNA carrier. (a) 2D schematic of the λ-DNA carrier with two independent aptamer probes specific to thrombin (dimensions: 87.7×67.8×61.1 Å) and AChE (dimensions: 211.6×129.7×195.4 Å). (b) Typical current-time trace recorded at −200 mV and re-filtered at 5 kHz clearly showing three levels. The 1st associated with the DNA carrier, 2nd with thrombin (~16-34 pA) and 3rd from AChE (~22-57 pA). (c) Only the translocation events exhibiting two distinct sub-peak were used for further analysis. As can be seen the fractional position correlates well with the relative positions of thrombin (0.2) and AChE (0.8). (d) Individual sub-peak amplitude and dwell time statistics obtained at voltages ranging from −180 to −300 mV. Values after '±' represent one standard deviation. The mean peak current (n=397) was determined via Gaussian fitting and summarised in (e) (i). Importantly both proteins are easily distinguishable not only by location but also by the current amplitude and dwell time, as observed by the individual scatter plots of the sub-peaks as shown in (e) (ii) and (e) (iii) for thrombin and AChE, respectively.

FIG. 13: Sensing of protein targets in human serum. (a) Typical current-time traces are shown for a serial dilution of human serum spiked with 100 mM KCl at applied voltages of −250, 0 and +250 mV. In all cases the serum was inserted inside the nanopipette. As is shown a dilution of 1:20 consists of a sufficiently stable baseline to be used in nanopore sensing. (b) DNA carrier with 3 TBA probes were incubated in HS with the current-time traces clearly showing sub-peaks associated with thrombin binding at −250 mV. (c) Similar to FIG. 3, the sub-peaks could easily be distinguished based on location (0.2), (0.7) and (0.9) (N=94). (d) Individual current amplitudes for all three sub-peaks, obtained at an applied voltage of −250, −400 and −450 mV with the average current determined via Gaussian fitting. Values after "±" represent 1 standard deviation.

Figure 14A:
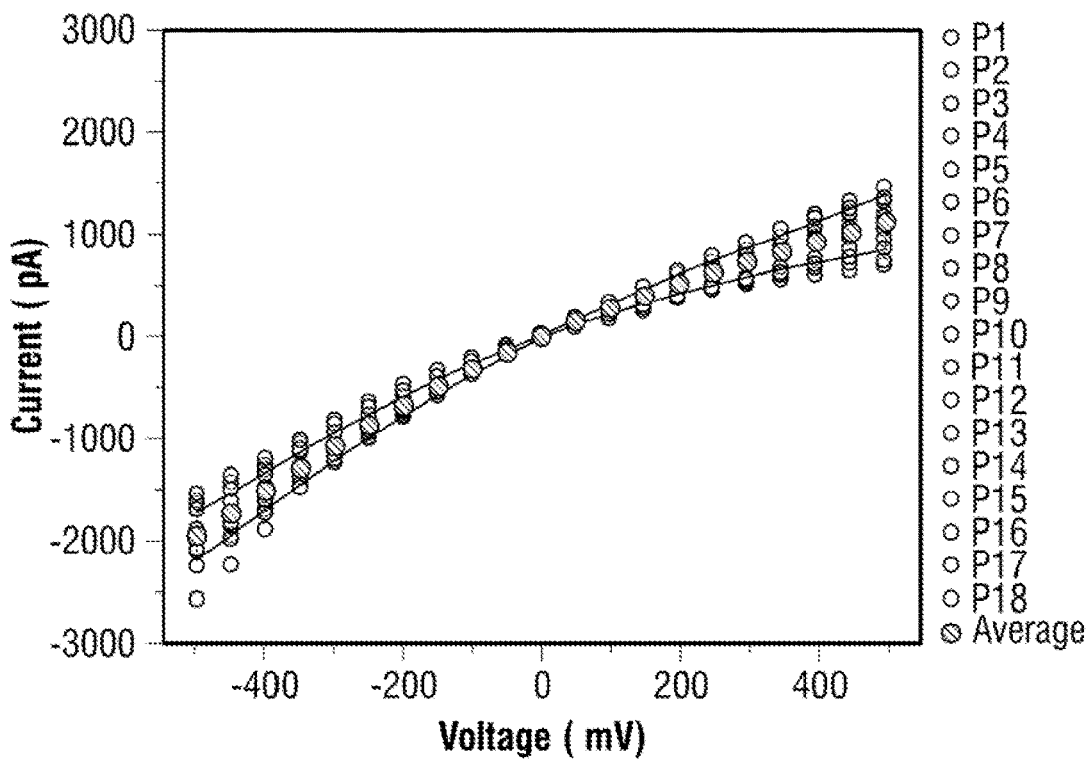
Figure 14B:
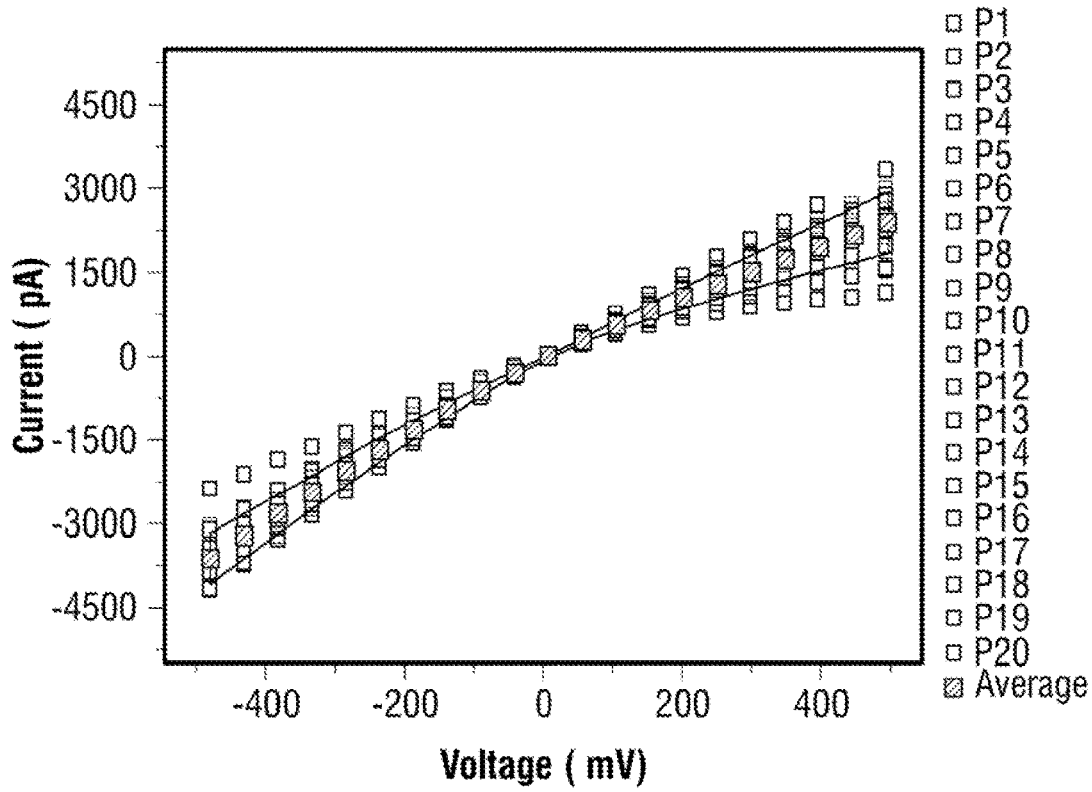

FIG. 14: Electrical nanopipette characterisation from a total of 38 Quartz nanopores. The quartz nanopores were fabricated with a quartz capillary inserted into a laser-based pipette puller yielding two asymmetric pores. The pores were then characterised electrically and optically. (a) Current-voltage curves from quartz nanopores with conductance 2.8±0.5 nS (n=18), used for experiments shown in FIGS. 10, 11, and 13. (b) Current-voltage curves from quartz nanopores with conductance of 5.8±0.8 nS (n=20) used for experiments shown in FIG. 12. All measurements were performed in 0.1 M KCL Tris-EDTA buffer.

Figure 15:
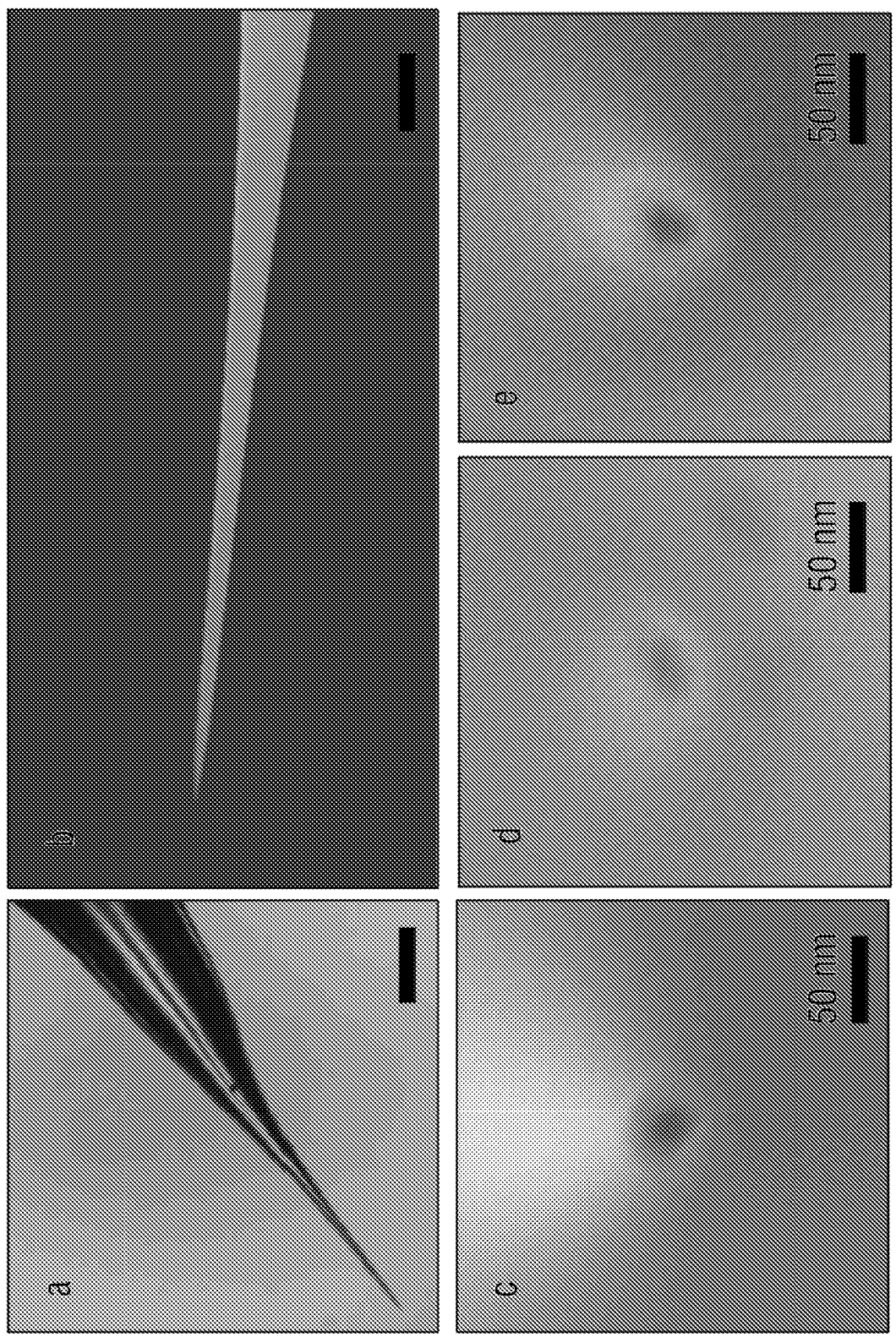

FIG. 15: Optical and SEM imaging of the nanopipette. (a) Bright field optical image (scale bar 500 µm) and (b) SEM showing the conical geometry and taper length of the quartz nanopipette, scale bar 50 µm. (c-e) Representative SEMs of nanopipettes used in experiments. The average diameters and 1 standard deviation as measured by SEM were 16±2, 19±2 nm, and 16±2 nm (in all cases n=4), respectively. Scale bars are 50 nm.

Figure 16:
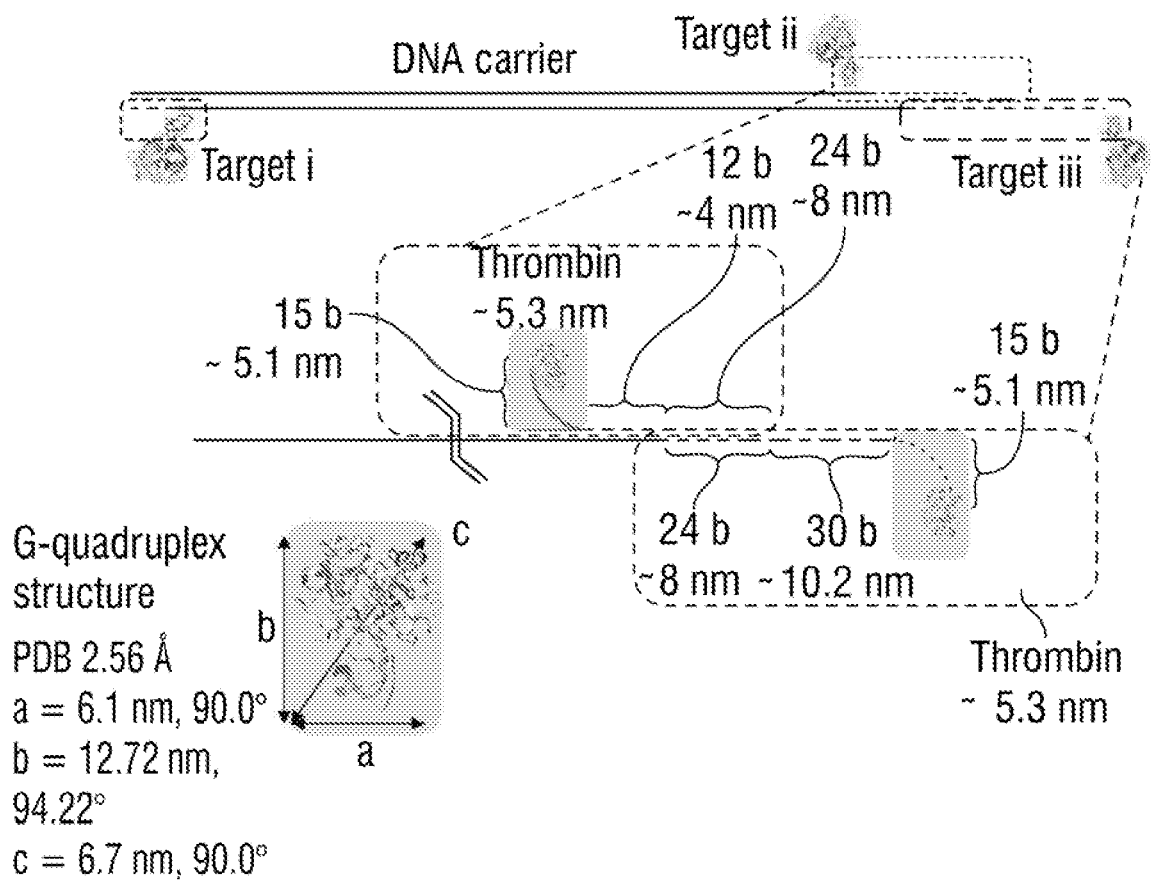

FIG. 16: Schematic and sequences used for detecting three thrombin protein targets. The sequences used for the modification of the DNA carrier with aptamer probes are as follows:

Target i (27 bases):
(SEQ ID NO: 5)
5'-<u>GGTTGG</u> TGTGGTTGGAGGTCGCCGCC-3',

Target ii (51 bases):
(SEQ ID NO: 6)
5'-<u>GGTTGGTGTGGTTGGGGGCGGC</u>GACCTAAGGTGTCGTGCGTAAGTTT

TTAA-3',

Target iii (69 bases):
(SEQ ID NO: 7)
5'-<u>GGTTGGTGTGGTTGG</u>TTTTTTTTTGTCTTTTTTTTTTTTCTGTTTTT

AAAAACTTACGCACGACACCTT-3'.

In all cases the aptamer sequences are shown is shown in black and underlined.

Figure 17:
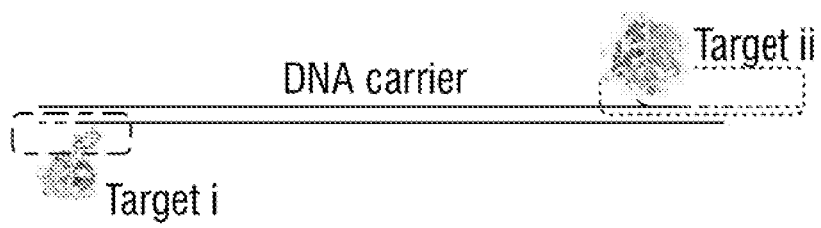

FIG. 17: Schematic of the designed aptamer detection probes used for thrombin and AChE. The sequences used for the modification of the DNA carrier with aptamer probes specific to thrombin and AChE are as follows:

Target i (27 bases, thrombin):
(SEQ ID NO: 9)
5'-<u>GGTTGGTGTGGTTGGAGGTCGCCGCCC</u>-3', Target ii (75 bases, AChE):
(SEQ ID NO: 8)
5'-<u>GGTTGACTGTAGCTCTGGCAGACGTAGTGTGAAGGTACCGGGCGGCG</u>

ACCTAAGGTGTCGTGCGTAAGTTTTTAA-3'.

In all cases the aptamer sequences are shown is shown in black and underlined.

Figure 18:
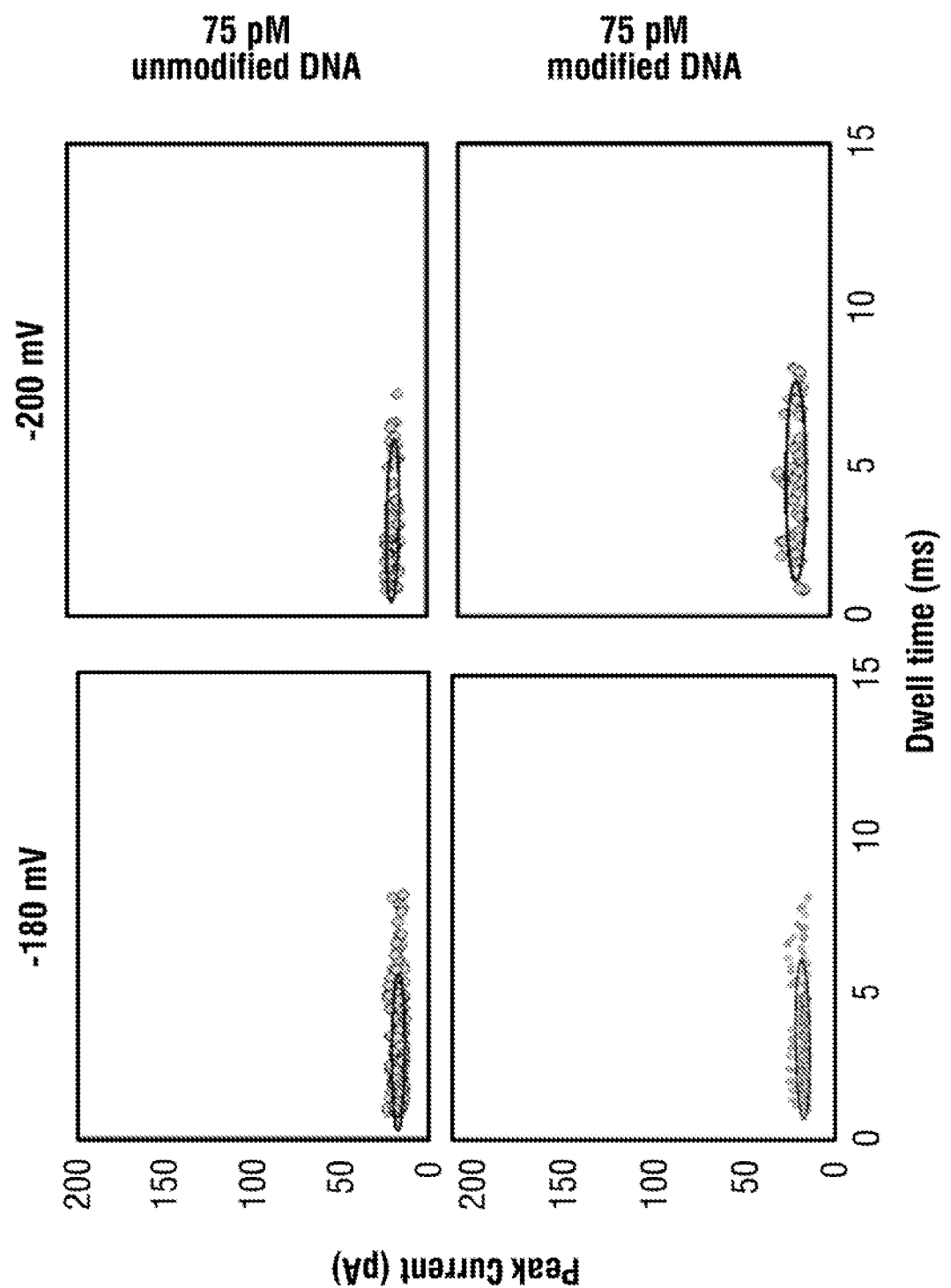

FIG. 18: Scatter plots for both aptamer modified and unmodified DNA carrier. Negligible change in the current and dwell time distributions were observed when comparing aptamer modified and unmodified DNA at −180 and −200 mV.

Figure 19:
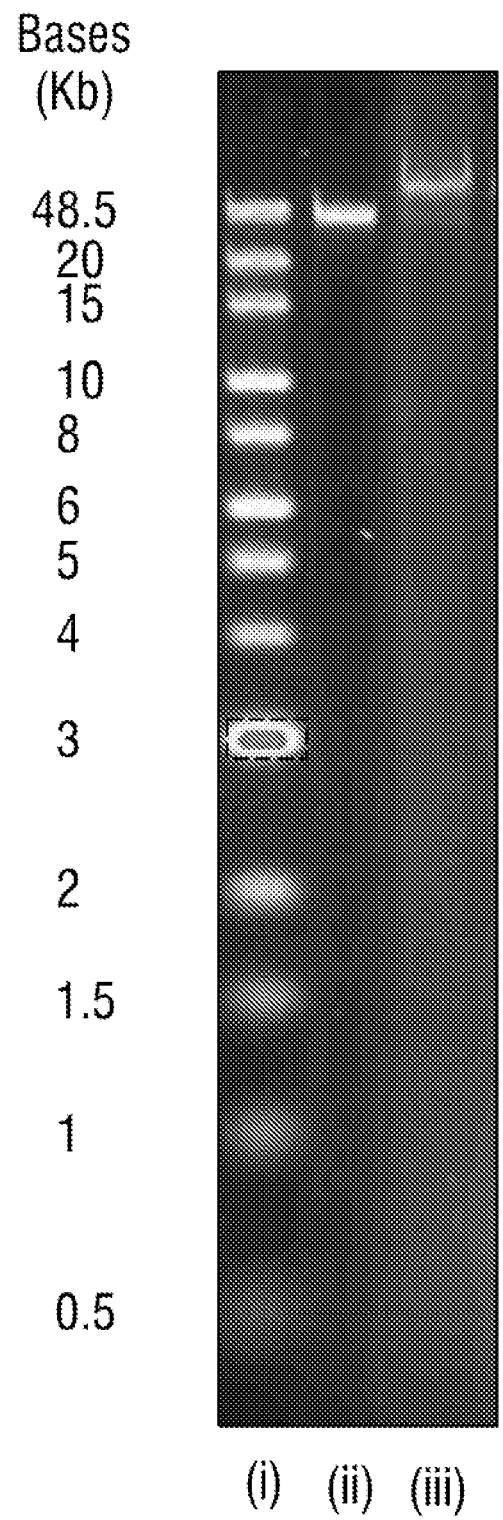

FIG. 19: Gel electrophoresis image for the unmodified and aptamer modified DNA carrier. From left to right (i) Extended 1 kb DNA ladder (ii) unmodified λ-DNA (iii) aptamer modified λ-DNA. A 0.65% agarose gel was used and separations were obtained at a voltage of 5.7V/cm for 1 hr in TBE buffer. The gel was then stained with SYBR Gold and imaged under UV light. The modified carrier shows that the majority of the aptamers are bound to the carrier causing a very small shift in the gel.

Figure 20A:
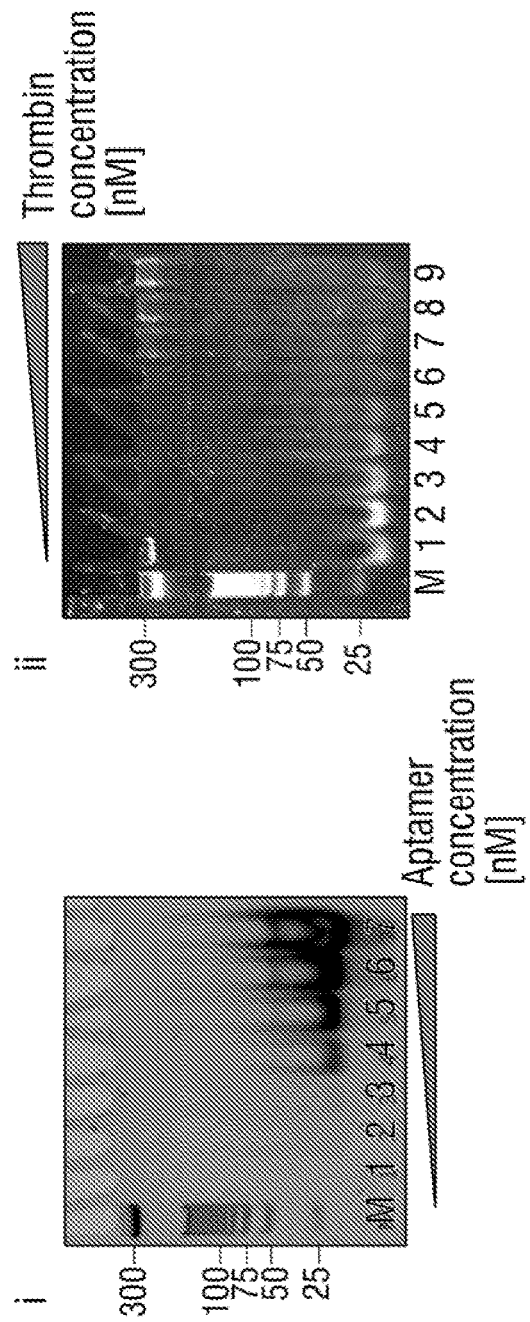
Figure 20B:
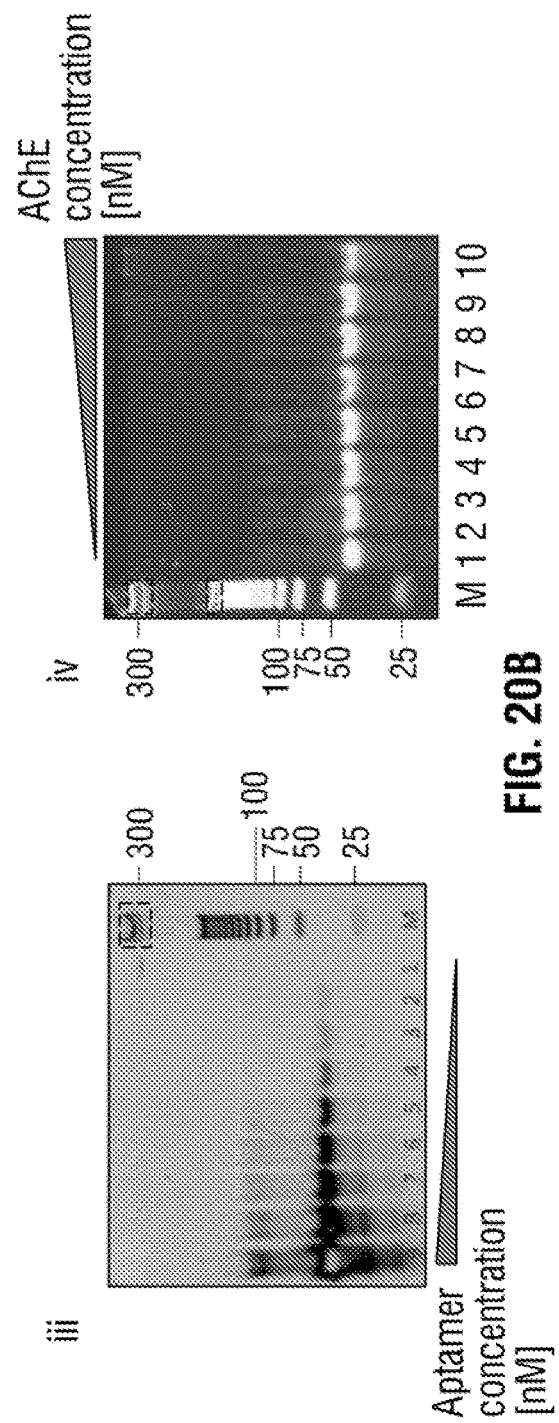

FIG. 20: Electrophoretic mobility shift assay (EMSA) to confirm the binding of the aptamers to thrombin and AChE targets. All gels shown above include a 25 bp ladder and indicated as M in the gel. (i) Thrombin (750 nM) was incubated with different concentration of modified TBA aptamer (top left) ranging from 0-5000 nM in 140 mM NaCl, 20 mM MgCl2, 20 mM PBS buffer pH 7.4 for 45 mins. The 7 lanes on the gel represent the following concentrations of aptamer (from left to right): 0, 50, 100, 250, 500, 1000 and 5000 nM. The samples were then loaded on a 10% native polyacrylamide cast gel and ran for 75 min at 80V and stained with SYBR gold and imaged under UV. The bottom band showed the unbound aptamer and as the aptamer concentration increases, a gradual shift showing the retardation of mobility by the thrombin binding to the modified aptamer. (ii) modified TBA (200 nM) was then incubated with different concentration of thrombin in the same binding buffer as (i) for 45 min. The 9 lanes consist of different thrombin concentration from left to right: 0, 250, 500, 1000, 1500, 2500, 5000 and 7500 nM. The samples were then loaded to a 10% native polyacrylamide cast gels and ran for 75 min at 80V and stained with SYBR gold and imaged. (iii) AChE (660 nM) was incubated with different concentration of modified AChE aptamer ranging from 0-5000 nM in 2.7 mM KCl, 4 mM MgCl2 PBS buffer pH 7.4 for 1 hour. The 9 lanes consist of different aptamer concentration from (left to right) 5000, 2500, 1000, 500, 250, 100, 50, 25 and 0 nM and placed in a 8% polyacrylamide cast gel and ran at 90 V for 75 min. The gel was then stained and imaged. A very clear band shift is observed as can be seen due to the sluggish moving of the protein-aptamer. (iv) Same format as (ii) however with AChE protein, AChE aptamer was fixed at 100 nM with a range of AChE concentration from left to right 0, 10, 50, 100, 250, 660, 1000, 2000 nM in the same binding buffer and placed in a 8% polyacrylamide gel and ran at 90V for 75 min. The gel was then stained with SYBR gold and imaged.

Figure 21:
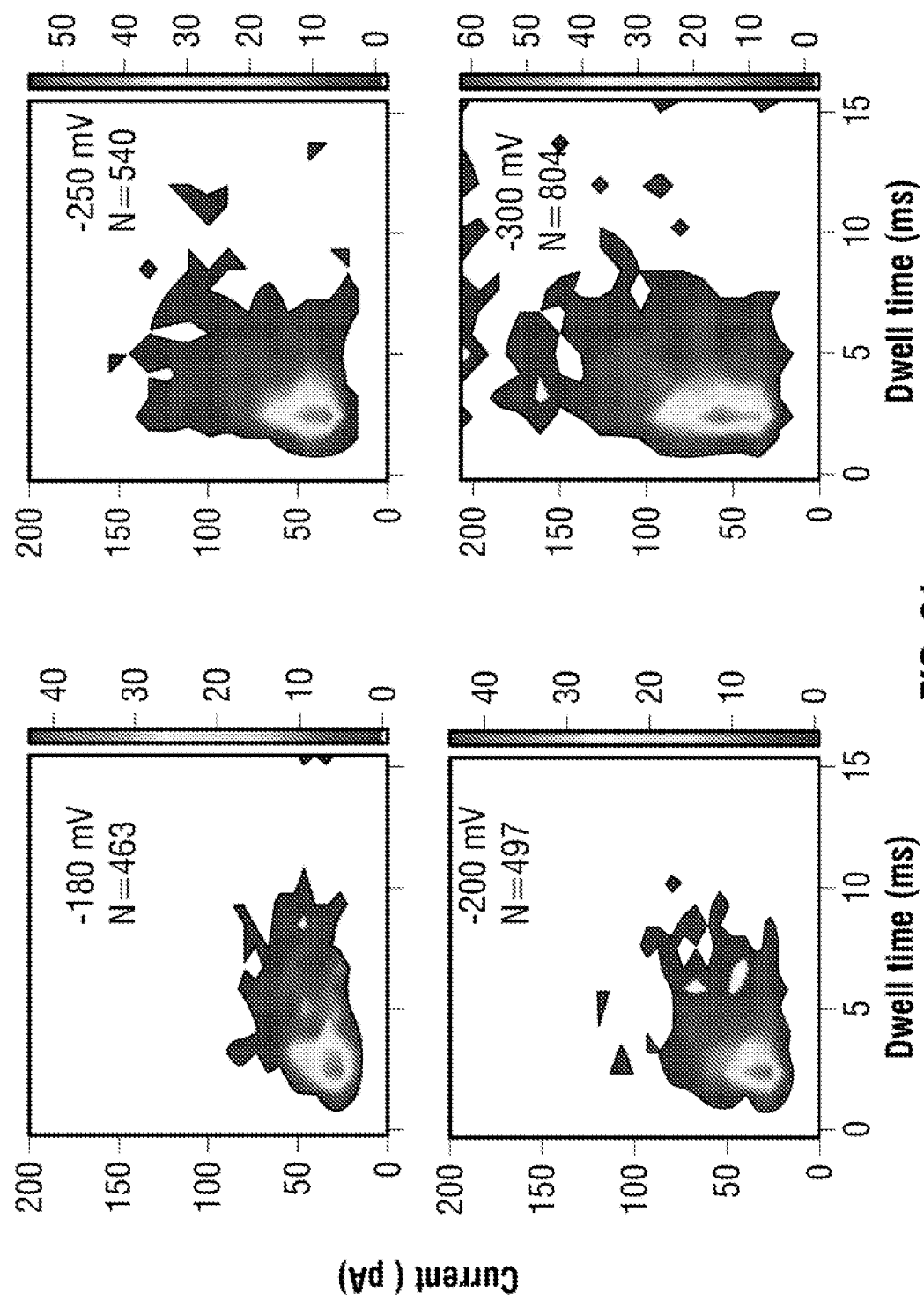

FIG. 21: Current and dwell time scatter plots for two proteins, thrombin and AChE bound to the same DNA carrier. This corresponding to the data shown in FIG. 12.

Figure 22A:
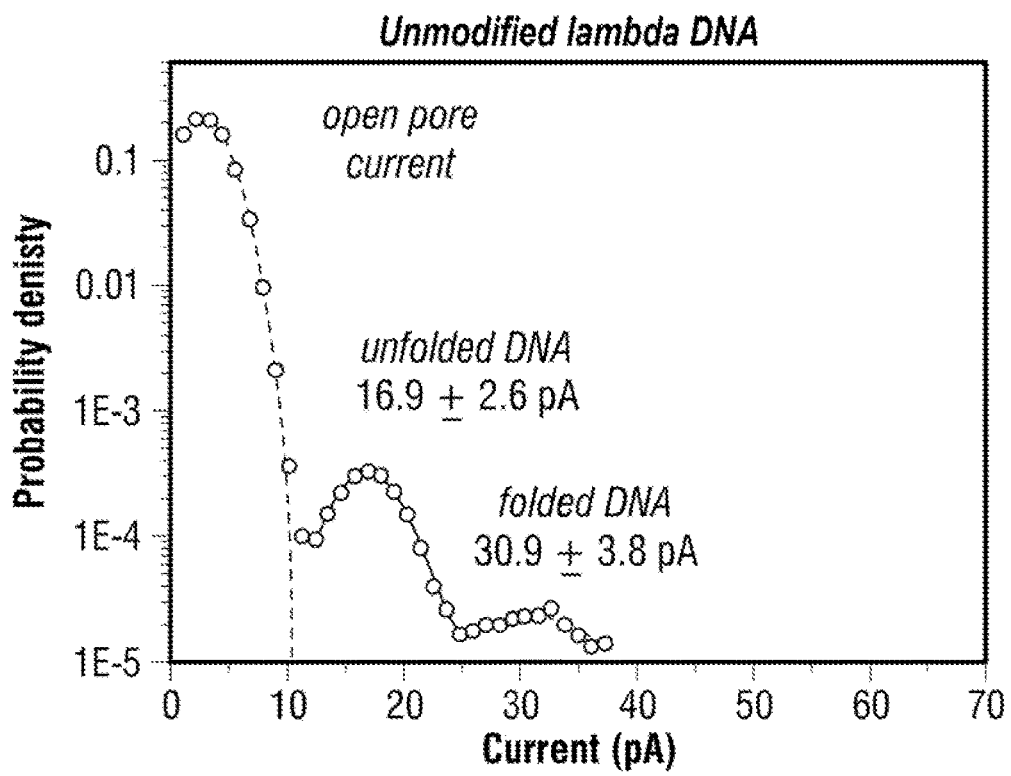
Figure 22B:
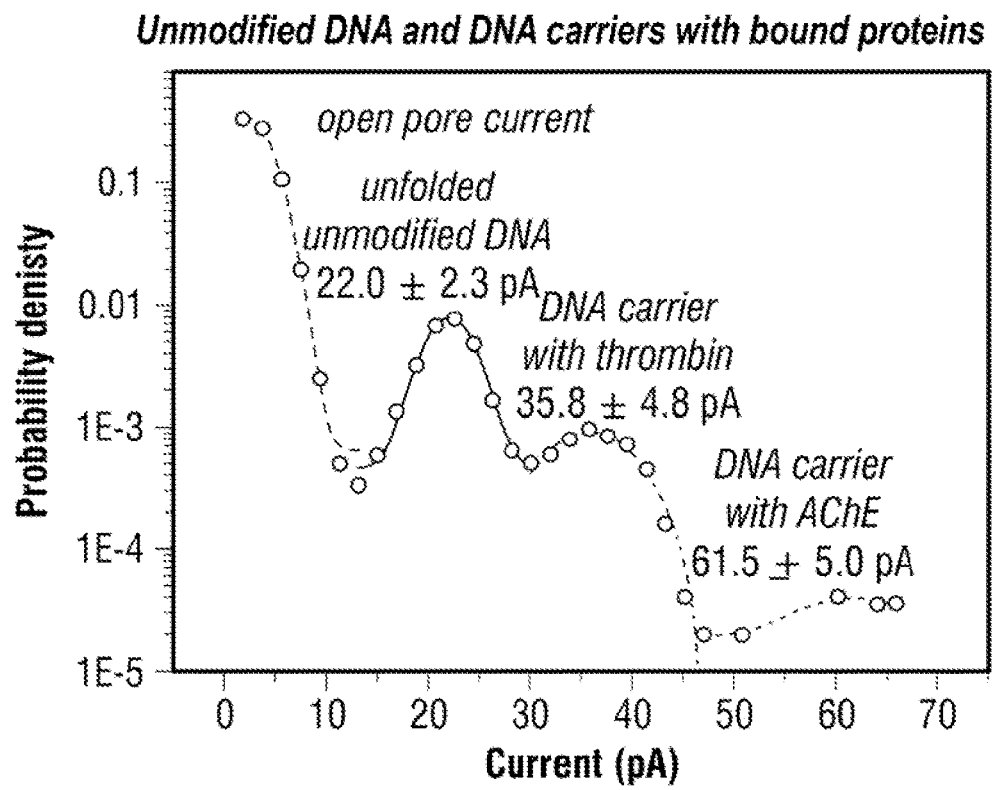

FIG. 22: Algorithm used for sub-peak thresholding. The method we use to differentiate between different molecular populations is as follows: 1) By using an all points current histogram we fit a Poisson distribution to define the background current. 2) The remaining peaks are fit to Gaussian distributions, and in the case of this data set we use a three-sigma confidence level to differentiate between free and protein bound DNA as shown below. 3) Each individuate translocation is assessed to confirm they exhibit multi-level behaviour. Only translocations with a minimum of 2 steps are defined as originating from a modified DNA carrier with bound protein. 4) Finally, the sub-peaks are analysed to remove the small underlying population due to folded DNA. Examples are shown for (a) unmodified λ DNA carrier and (b) λ DNA carrier bound to thrombin and AChE proteins. Note that in the example shown, different nanopipettes are used which results in a slight offset between peak amplitudes. As shown above this analysis is performed on a single data file.

Figure 23:
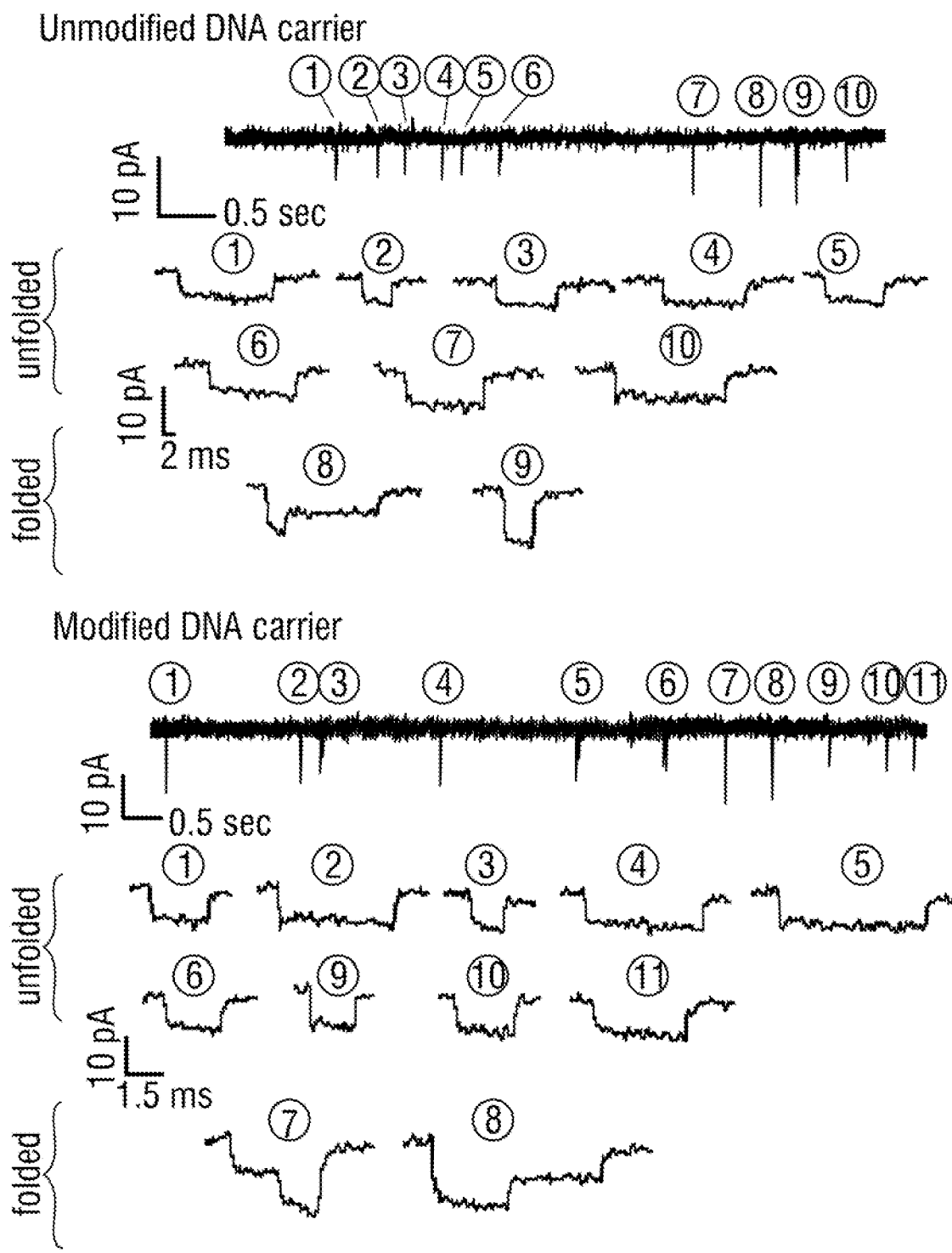

FIG. 23: Representative examples of unfolded and folded DNA for both the unmodified and aptamer modified DNA carrier. Continuous current-time trace and zoomed individual translocation events for both unmodified and aptamer modified DNA carrier. Events #8 and #9 in top trace #7 and #8 in the bottom show representative translocation events in folded configuration. On average 10% of all translocation events were observed to have a folded component. The applied voltage was −150 mV. The traces were filtered with a low pass filter with a cut-off frequency of 5 kHz for visualisation.

Figure 24:
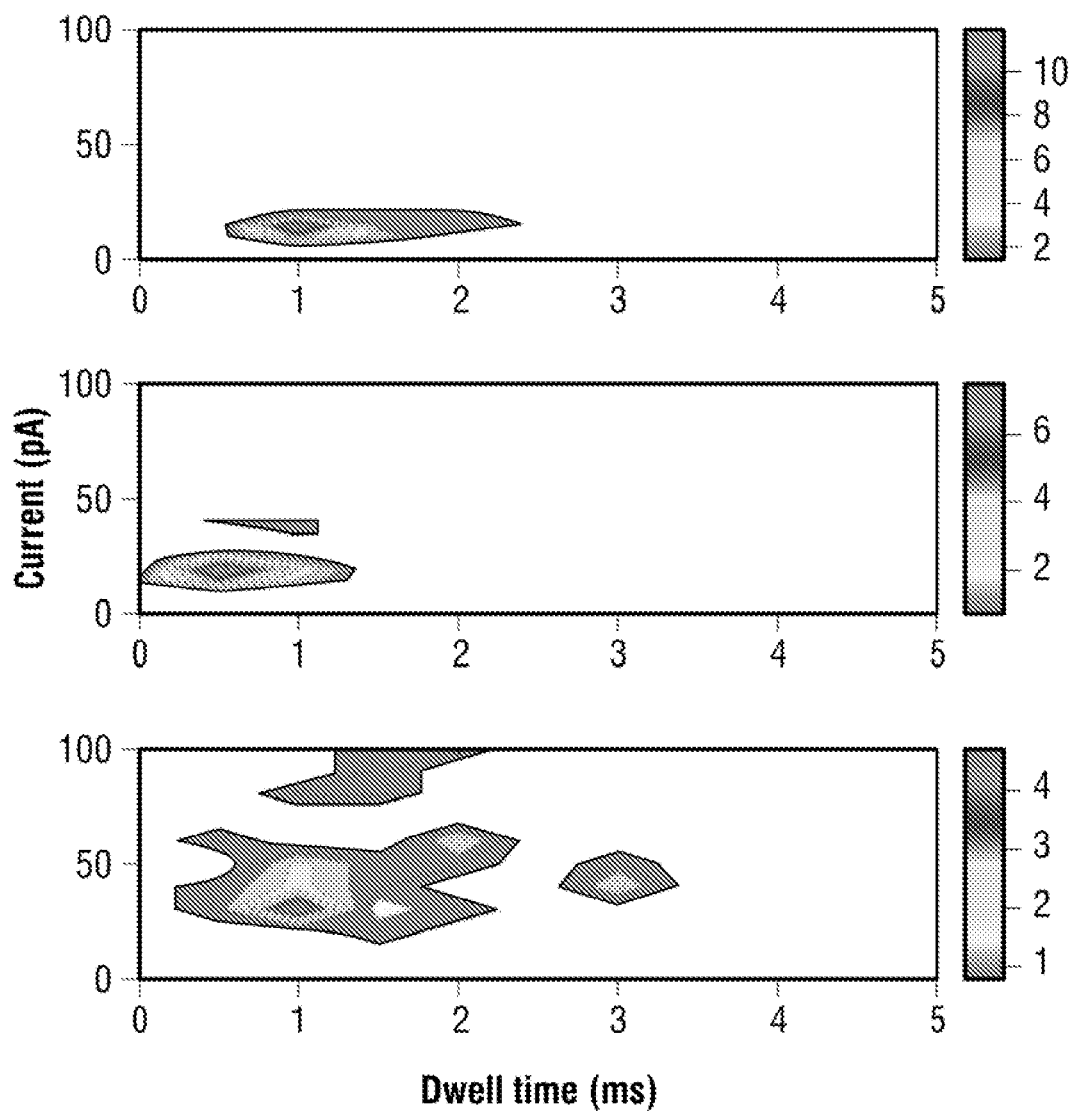

FIG. 24: Sub-peak comparison for thrombin and AChE bound to a DNA carrier. Scatter plots are shown for thrombin, AChE, and and the sub-peak associated with folded DNA for reference. All measurements were taken at −200 mV. There is less than 1% overlap between AChE and folded DNA based on the sub-peak amplitude and dwell time and less than 10% overlap between thrombin and folded DNA.

Figure 25:
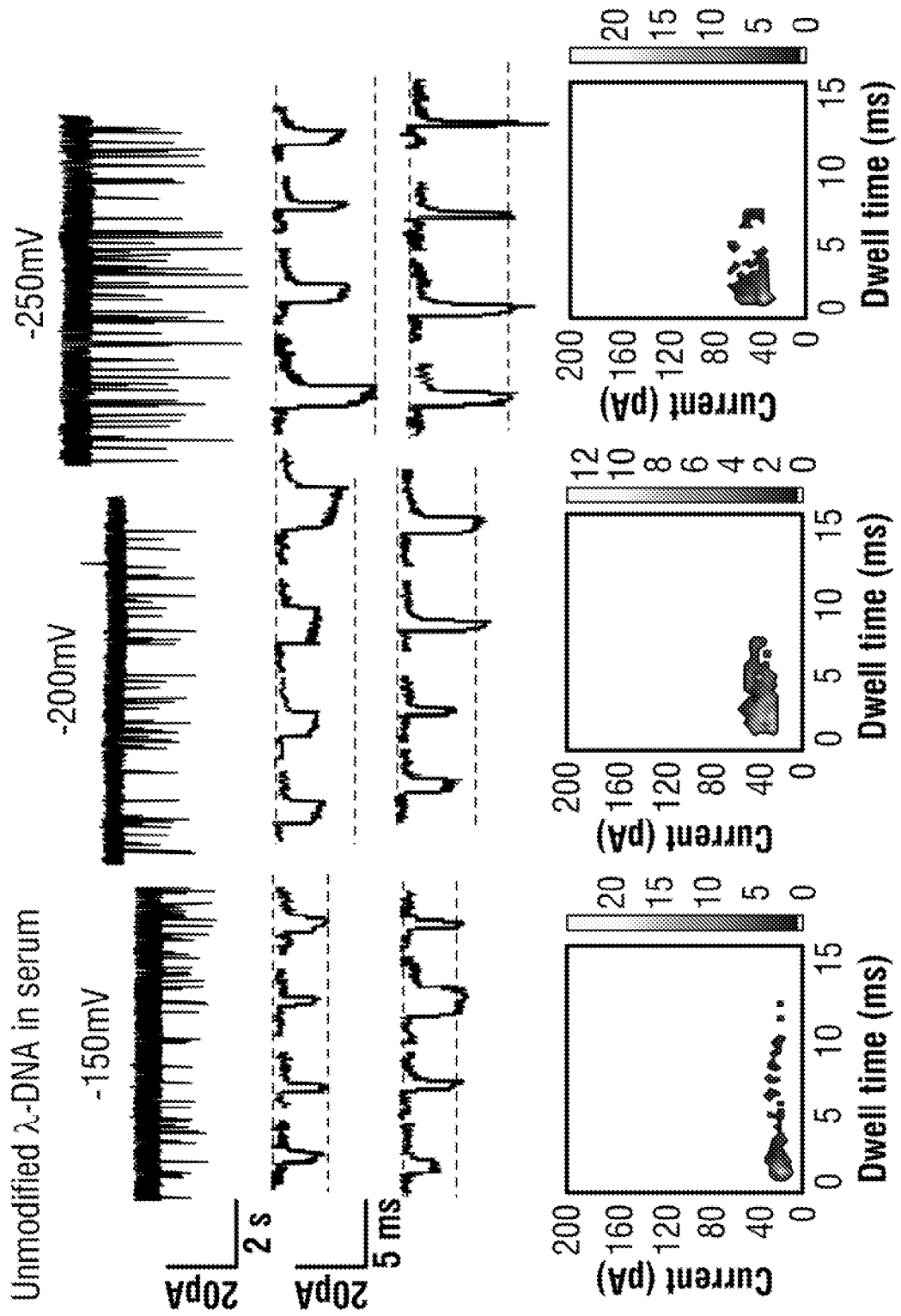

FIG. 25: Control experiments for unmodified DNA carrier in serum. Examples of typical current-voltage traces along with voltage dependant scatter plots are shown for −150, −200 and −250 mV respectively. In all cases statistics are similar to detection of unmodified DNA in buffer alone.

Figure 26:
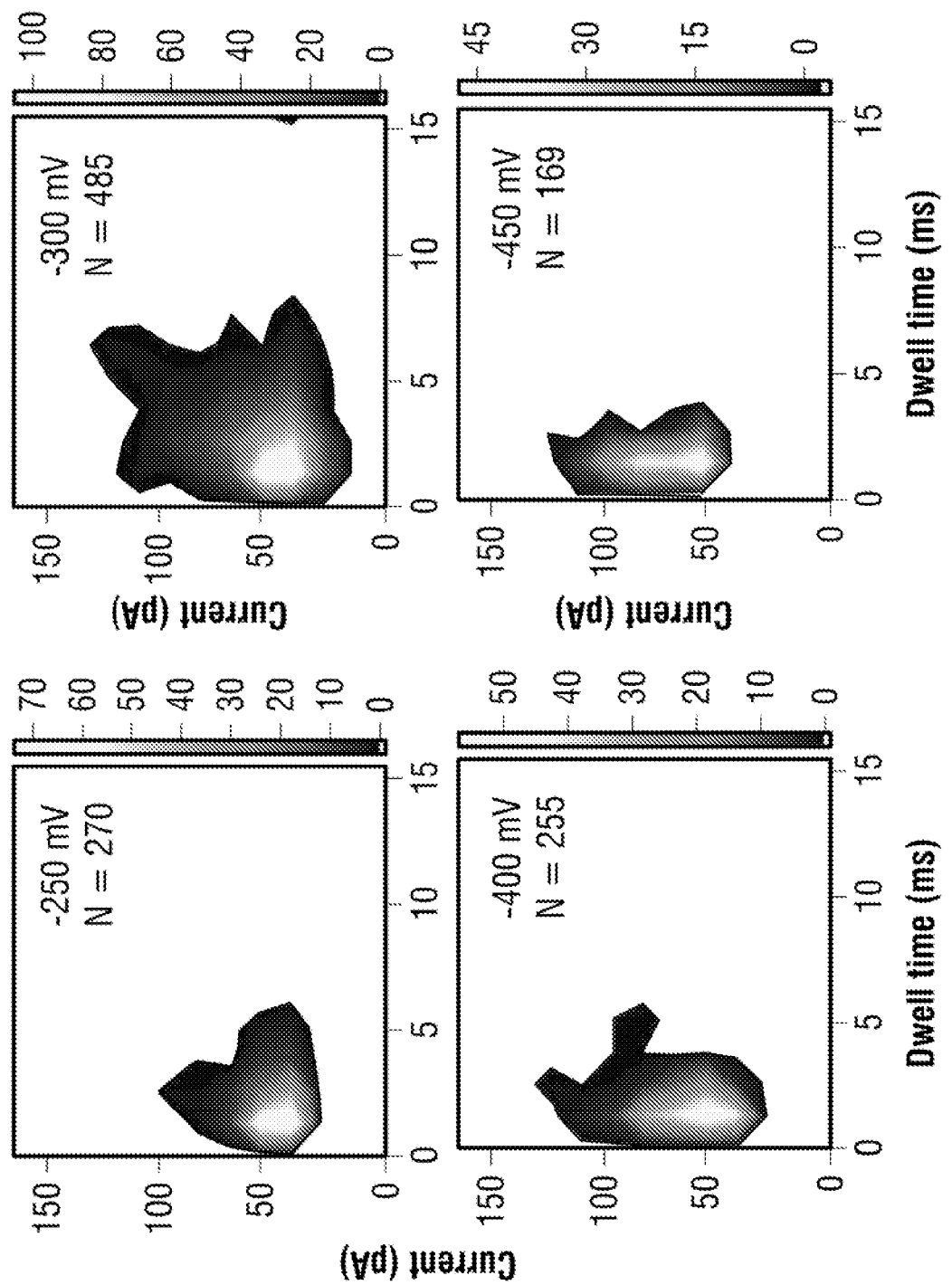

FIG. 26: Current and dwell time scatter plots corresponding to the data shown in FIG. 13. DNA concentration was 100 pM and voltage was varied between −250 to 450 mV.

DETAILED DESCRIPTION

The present inventors have developed a fully flexible and selective approach allowing the accurate detection of multiple proteins utilising aptamers. Advantageously, the method can be used in complex samples such as human serum.

Aptamers are ssDNA or ssRNA oligonucleotides that have the ability to non-covalently bind to a target molecule with high affinity and selectivity. Aptamers sequences can be selected in vitro by SELEX (systematic evolution of ligands by exponential enrichment)[32-33] and their subsequent synthesis is less expensive with little to no inconsistency between batches compared with antibodies.[34] They have been widely use in diagnostics and as therapeutics agents in the last few years.

The present inventors have utilised aptamers as small recognition sequences that can be hybridised to complementary sequences of a larger carrier nucleic acid via single-stranded sections engineered into the aptamer sequence, leading to the formation of specific detection probes. The engineered aptamers may herein be described as single-strand tagged aptamers, thought should also be noted that the use of the term "aptamer" herein is intended to include a single-stranded tag region unless otherwise specified.

The presence or absence of a specific target in solution can then be identified by detecting the presence of the aptamer in complex with the carrier nucleic acid and the analyte. In the present disclosure, the complex of these components is sometimes described as the carrier nucleic acid/aptamer/analyte complex.

The physical properties of the carrier nucleic acid can be utilised to allow for the detection of the carrier nucleic acid/aptamer/analyte complex. Such physical properties include, but are not limited to, molecular weight and charge. The particular physical property of interest will depend in part on the detection method employed. For example, the presence of the carrier nucleic acid may allow the complex to be detected by voltage-driven translocation through a nanopore. In certain other embodiments the additional steric hindrance caused by a very large carrier nucleic acid molecule in the carrier nucleic acid/aptamer/analyte complex may assist in detection. The carrier nucleic acid may typically be a double-stranded nucleic acid molecule with single-stranded overhangs at its 3' and/or 5' ends. Alternatively or in addition to overhangs, the carrier molecule may have one or more a single-stranded regions elsewhere along its length. In particularly preferred embodiments, the carrier nucleic acid has multiple single-stranded regions to which multiple different single-strand tagged aptamers may bind. In this way the present method can be easily designed to detect multiple analytes simultaneously. The carrier molecule will typically be DNA or RNA.

Figure 1A:
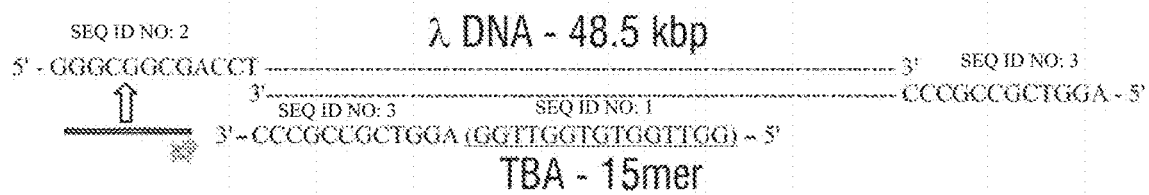
FIG. 1 A) A 2D Schematic of the λ-DNA (48.5 kbp) template with 12 base oligonucleotides overhangs on both the 5' and 3' termini. The specific detection probe (27 mer) was formulated through the addition of the complementary sequence [in green] of the 5' of the λ-DNA and the TBA sequence [in light blue]. B) 3D schematic of three detection probes on λ-DNA: the $1^{st}$ detection probe was formed by hybridisation to the 5' end of the molecule allowing the $1^{st}$ target recognition. The $2^{nd}$ detection probe was formed on the opposite strand to the λ-DNA template on the 3' end while the $3^{rd}$ detection probe was formed by complementary hybridisation to the $2^{nd}$ target probe sequence. The system was designed to allow spatial separation between the three probes i.e. long distance between the $1^{st}$ and $3^{rd}$ target while the $2^{nd}$ and $3^{rd}$ probes are on the opposite strands upon binding to the target. C) Schematic of the three targets binding selectively and specifically to the detection probe in human serum through the nanopore. D) Also shown are example translocations for the detection of 3 and 2 proteins bound to the aptamers on the DNA carrier. Importantly, the sub-levels can be used to differentiate between proteins both in terms of location and magnitude.
Figure 1B:
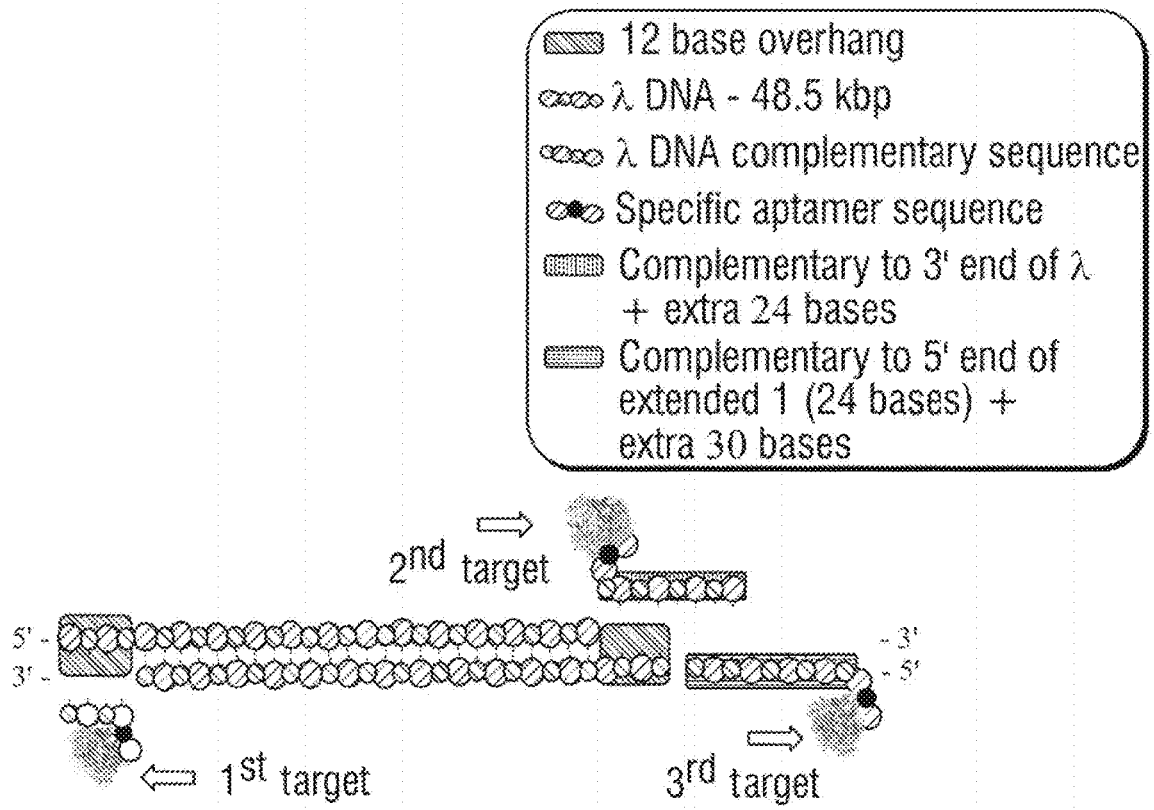
Figure 1C:
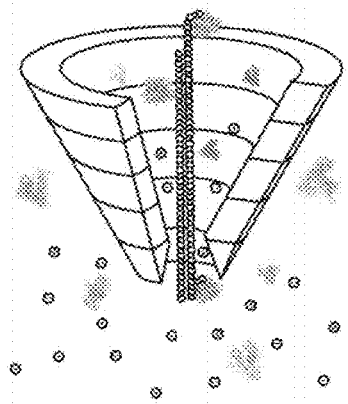
Figure 1D:
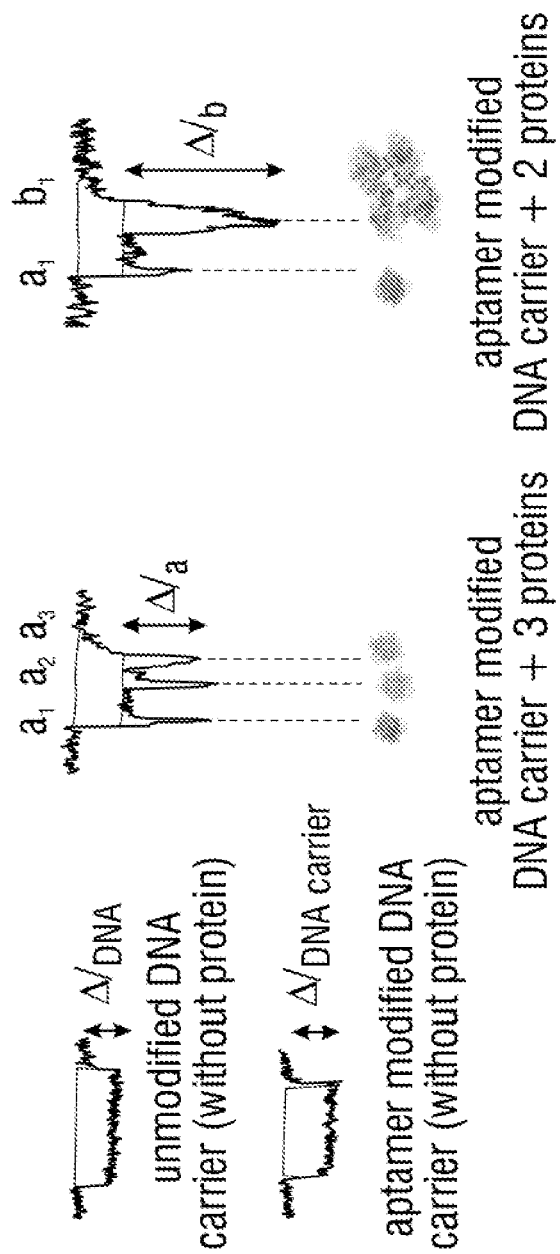

Any detection method that can differentiate between the carrier nucleic acid/aptamer complex and the carrier nucleic acid/aptamer/analyte complex may be used with the present method. One method of detection involves studying the characteristic transient change in current during the dsDNA level translocation, see FIG. 1D. Alternative detection methods are also contemplated, including but not limited to fluorescence detection and confocal microscopy. Advantageously, the present method is not dependent upon attaching antigens or detection moieties (such as antibodies) to the carrier nucleic acid via conjugation chemistry. Instead, hybridisation between the single-strand tagged aptamer and carrier molecule is utilised. This leads to several advantages, including but not limited to simplified manufacture and use.

Where nanopore detection is used, the simplified carrier nucleic acid and aptamer set up avoids the possibility of conjugated antigens becoming denatured, which would cause the detection precision and location to fail, as the translocation peak in the nanopore would still occur due to the relatively large size of antigens along the DNA occupying the pore leading to a sub-level peak current. It would also be hard to differentiate whether the translocation event was caused by specifically binding of antibodies or just the denatured antigen along the carrier nucleic acid.

A further advantage of the present method is that neither the analytes, carrier nucleic acids nor the aptamers need to be immobilised (such as to a surface) at any stage. Detection can instead be conducted in solution, greatly open up the detection capability and simplifying the procedure.

The simplified nature of the present method is also advantageous because aptamers can be generated for any analyte with relative ease. Certain prior art methods have relied upon the construction of aptamers that undergo conformational changes upon target binding. This, however, greatly complicates the development of aptamers for new targets. The methods described herein, no conformational changes in the aptamers is required, which leads to a more simplified system that can be applied to a wide range of target analytes.

EXAMPLES

Materials & Methods
Solutions & Reagents

All nanopore measurements were carried out at room temperature and were performed in 100 mM KCl, 10 mM Tris and 1 mM EDTA solution at pH 8 unless otherwise stated. λ-DNA which consisted of 12 base overhangs was purchased from (New England Biolabs, UK) and all designed aptamer probes were obtained from (Invitrogen custom oligonucleotides, UK). All the sequence information of detection probes used in this work are listed below. α-thrombin was obtained from (Cambridge Biosciences, UK). Acetylcholinesterase and human serum (from clotted human whole blood) were purchased from (Sigma-Aldrich, UK).

DNA/Aptamer Detection Probe Hybridization

5 µL of λ-DNA [500 µg/mL] and 1 µL related aptamer probes [5 µM] were mixed in a total volume of 20 µL of 150 mM NaCl, 10 mM $MgCl_2$ Tris-EDTA buffer at pH 7.4 followed by 5 mins heating to 95° C., 10 mins annealing to 65° C. and cooling to room temperature for 10 mins. The excess aptamer probes were then removed by 100 kDa MWCO Amicon Ultra filter (Millipore, UK) before incubating with targets allowing approximate 1:1 ratio of the DNA carrier to aptamer probe.

Target Detection 0.5 µL of [93.38 µg/mL] of α-thrombin or 1.3 µL of [1.1 mg/mL] of AChE or 12 µL of human serum was incubated with total 20 µL, of aptamer probes for 45 mins and diluting the incubated complex in a total 750 µL buffer or human serum (1:20) to yield a final concentration of ca.100 pM λ DNA-protein complex for translocation. Either in 100 mM KCl buffer or (1:20) human serum diluted with 100 mM KCl, 10 mM Tris and 1 mM EDTA solution was used at pH 8.

Nanopore Fabrication

Quartz capillaries (Intracel Ltd, UK) length 75 mm with 0.5 mm filament was placed inside a plasma cleaner to remove any organic contaminants. Nanopipettes were fabricated using a P-2000 laser-based pipette puller (Sutter Instrument, US). The pipettes used in FIGS. 2,3 and 5 were fabricated from previous protocol reported.[12-13] The pipettes used in FIG. 4 were fabricated using a two-line program: (1) HEAT: 775; FIL: 4; VEL: 30; DEL: 170; Pul: 80, (2) HEAT: 825; FIL: 3; VEL: 20; DEL: 165; Pul: 180 to yield a conductance of 5.8±0.8 nS. It should be noted that the above parameters are instrument specific and might have slight variations due to local temperature and humidity.

Ionic Current Measurement and Detection

The ionic current detection and translocation experiments were carried out with an Axopatch 200B patch clamp amplifier (Molecular Devices, USA). The analyte was placed inside the negative charged quartz nanopore and the headstage was connected via Ag/AgCl electrodes and applied with negative potential for translocation studies. Quartz nanopore dimensions were measured by SEM and by ionic conductance indicating nanopore diameters between ~15-40 nm. The signal was filtered using a low pass Bessel filter at 10 kHz and digitized with a Digidata 1440A at a sampling rate of 100 kHz. Data was processed using a custom written Matlab script.

Proof—of—Concept (with 2 Targets)

λ-DNA was chosen as a template due to its rigidity and well-defined current blockade behaviour as well as the presence of 12 base overhangs on both the 5' and 3' end termini enabling hybridisation of a complementary oligonucleotide. The complementary oligonucleotide was further extended with aptamer sequences leading to the formation of a specific detection probe. Thrombin binding aptamer (TBA), a 15-mer (GGTTGGTGTGGTTGG SEQ ID NO: 1) was selected for the model system as its structure has been extensively studied by solution NMR[35-36]. TBA interacts with human alpha thrombin (α-thrombin) selectively with a $K_d$~35-100 nM in solid phase assays. α-Thrombin (M.W. of 37.5 kDa; pI of 7.0-7.6), a trypsin like serine protease is the only enzyme capable of catalysing the conversion of soluble fibrinogen into insoluble fibrin. A high pM range of thrombin in blood is known to be associated with thrombotic diseases so that it is important to detect this protein at trace level with high sensitivity and so prevent thrombosis.

Nanopore experiments were performed using quartz nanopipettes with conductance of 2.8±0.5 and 5.8±0.8 nS at 0.1 M KCl. Electrical and optical characterisation (Scanning electron microscopy) of the pipettes can be found in FIG. 6. Nanopipettes were chosen due to their ease of fabrication, low capacitance and low levels of high frequency noise. The ionic current signals of unmodified λ-DNA can be seen in FIG. 2A with i) schematic of the molecule ii) representative and current-time trace, iii) expanded current blockades when 100 pM of linear DNA is added to the nanopore and iv) scatter plot of dwell time and current with an applied potential of −200 mV. The negatively charged DNA molecules inside the nanopipette migrate toward the end of the tip resulting in an overall increase in the conductance. Upon the addition of two targets, the highly negatively charged complex (negatively charged aptamer and presence of negatively charged residues on the surface of bound thrombin at pH 8) enhances further the ion flow in the pore resulting in two distinct current blockades within the dsDNA current blockade level, which we correspond to the thrombin, with magnitude up to 45-62 pA depending on the nanopore used and voltage applied see FIG. 2*c*. These events are caused by the individual thrombin molecules binding to the aptamer probe as they were not observed when performing translocation to unmodified λ-DNA. A few sub-level events of lower magnitude were also observed, with some wider (longer dwell time) and sharper (higher peak current). Without wishing to be bound to any one theory, the inventors hypothesise this is due to the conformation changes of the complex upon binding to different binding sites of thrombin in solution. TBA folds into two G-quartets connected by two TT loops upon interaction with the thrombin anion exosite I, while TGT loop is in close proximity to the heparin binding site of neighbouring thrombin molecules.[35, 37] Literature also reported presence of potassium ion gives more stable quadruplexes and enhances the formation of TBA-thrombin complexes.[38]

An agarose gel was used to confirm the hybridisation of the aptamer probe to λ-DNA while a gel shift assay clearly showed the expected shift trend upon thrombin binding to the aptamer probe, FIG. 7. Control translocation experiments were also performed to test the specificity and suitability of the probe. Experiments with aptamer modified λ-DNA, unmodified λ-DNA, λ-DNA with non-specific probe and λ-DNA with non-specific probe with thrombin can be found in FIG. 2*b* and Table 1 (FIG. 8) respectively.

Multiplexing with 3 Targets

The initial 27mer design (15 aptamer sequence+12 base overhang) allowed the rapid and distinct detection of two targets as seen by two peaks on either size of the translocation blockade. In order to accommodate an additional target, the $2^{nd}$ binding domain can be extended to 51 bases. Hybridisation of the second binding domain with an additional oligos (24 mers) allows formation of a third target region with a total length of 69 nucleotides. The $2^{nd}$ and $3^{rd}$ probes were designed to be on the opposite strands to provide spatial resolution and avoid steric hindrance clashes upon binding to two targets. Three aptamer probes were incubated with three fold excess of thrombin for 45 mins before electrophoretic translocation through a nanopore. Analysis of the current trace showed three independent current spikes within the dsDNA level: one closer to the tail of the molecule with the other two almost next to each other. The specific passage and location of the protein binding to the probe could be seen in FIG. 2C. The amplitude of the protein levels within the dsDNA were similar compared to the two targets studies suggesting the extended aptamer probe does not affect by the extra binding domain. Assuming a binding domain every 1000 bases (~300 nm), which definitely have sufficient spatial resolution for various size of targets to bind to in different conformation and this would allow for >40 proteins to be detected. The potential to extend the specific probes further on either 5' or 3' of λ-DNA could lead to even more binding domains, certainly provide an accurate and flexible route to detect of targets simultaneously.

Detecting 2 Different Targets

Figure 4A:
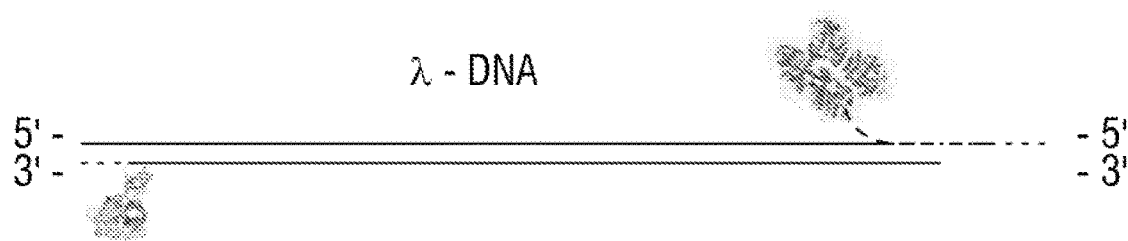
FIG. 4 (a) 2D Schematic of the λ-DNA carrier with two independent aptamer probes specific to thrombin (dimensions: 87.7×67.8×61.1 Å) and AChE (dimensions: ~211.6×
Figure 4B:
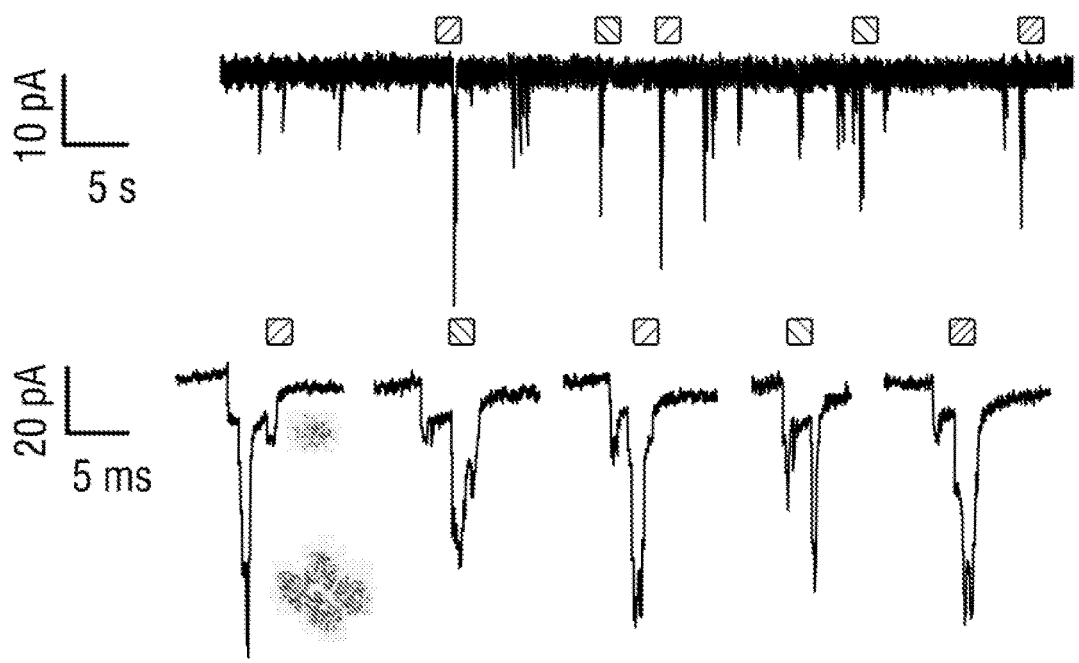
Figure 4C:
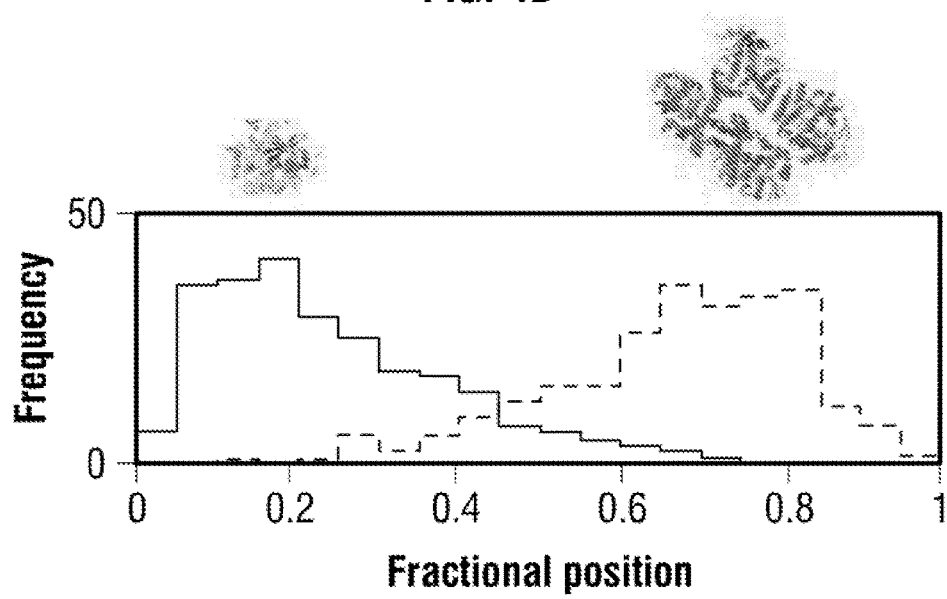
Figure 4D:
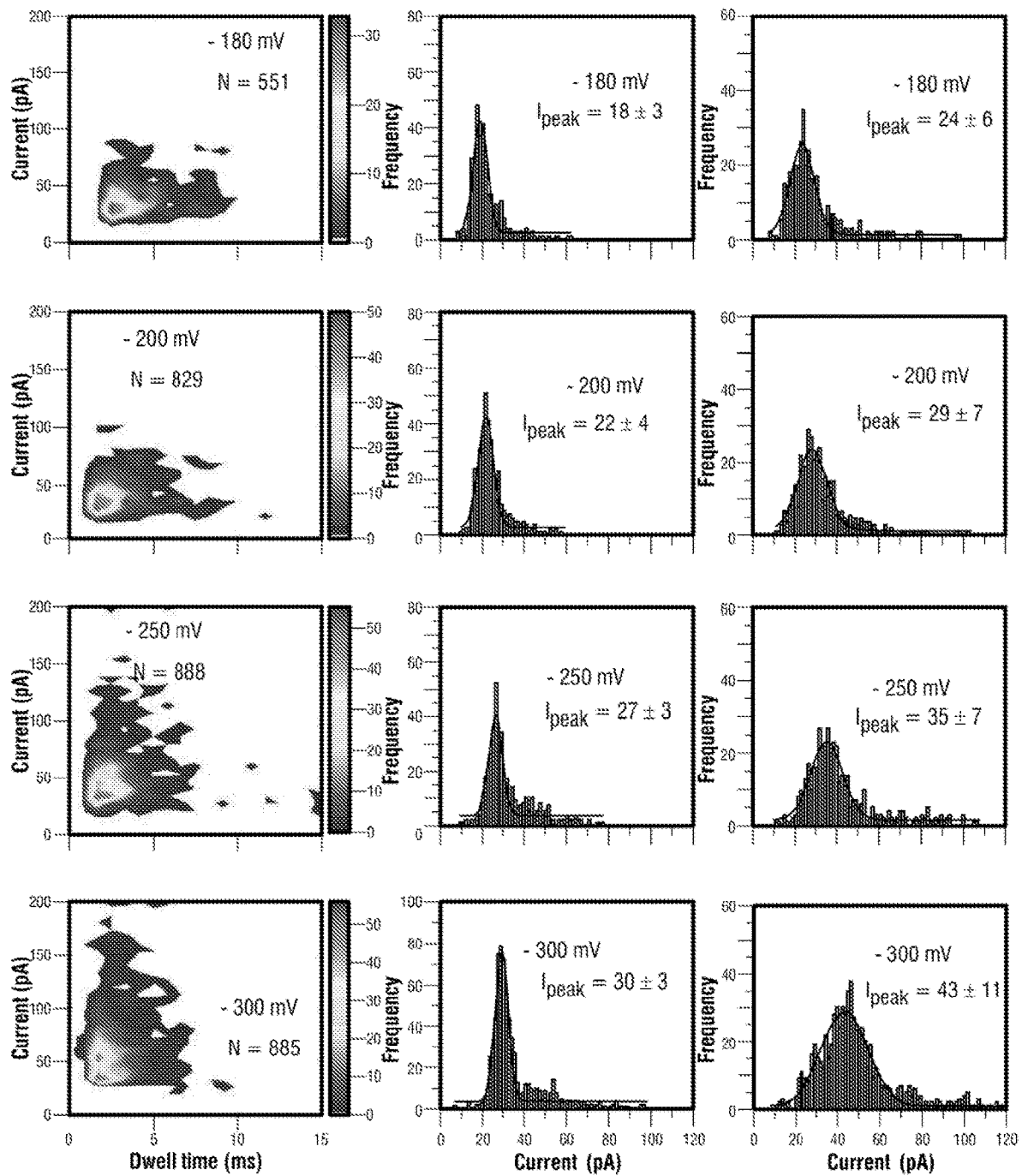
Figure 4E:
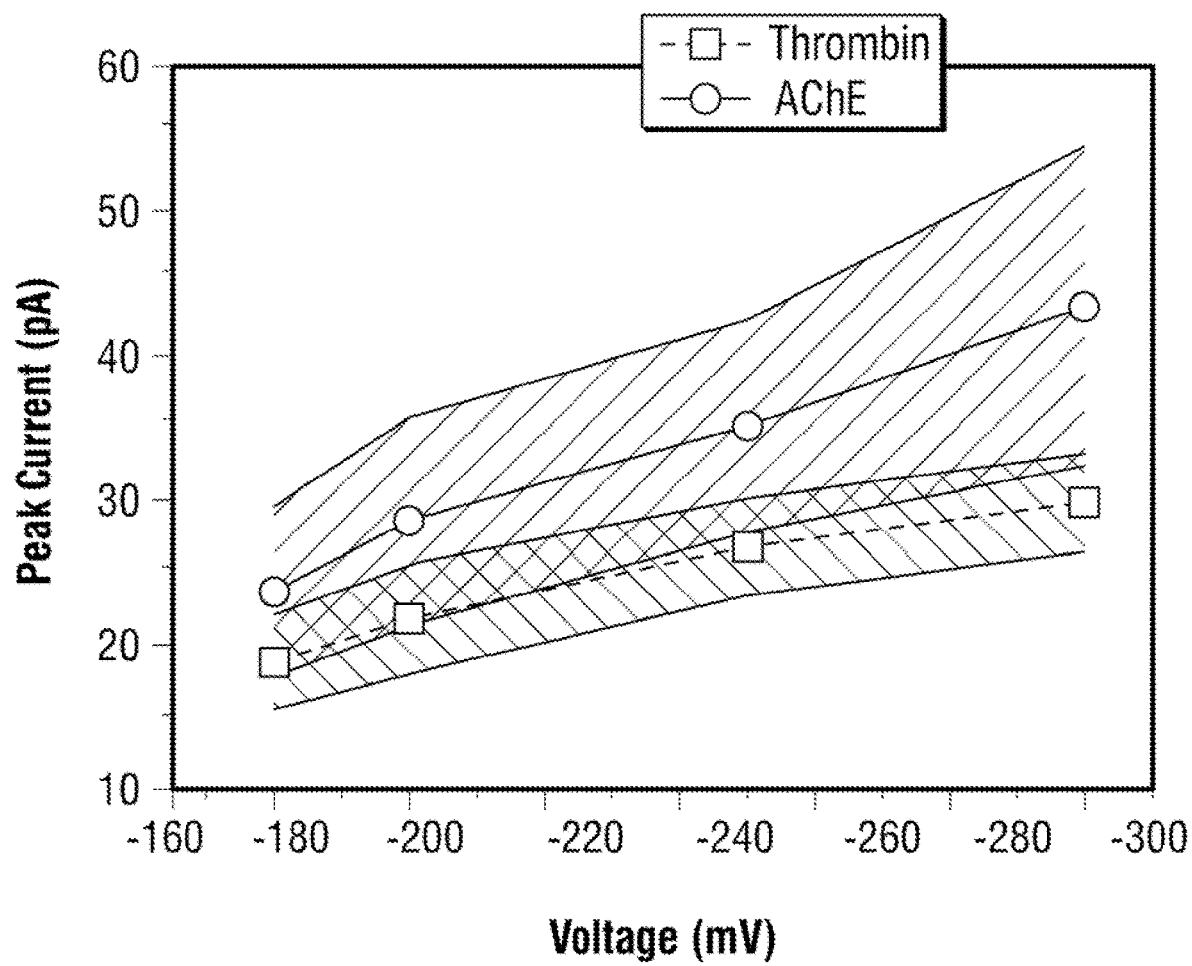
Figure 5A:
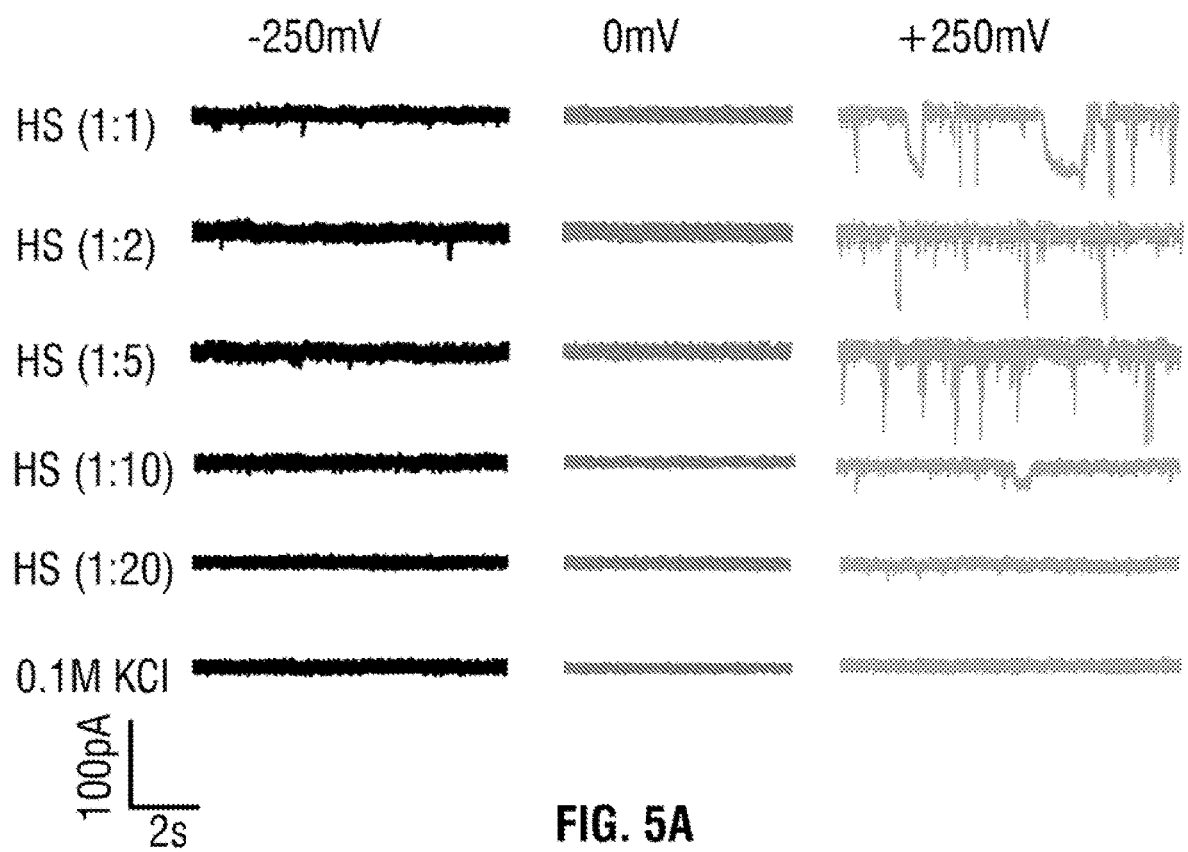
Figure 5B:
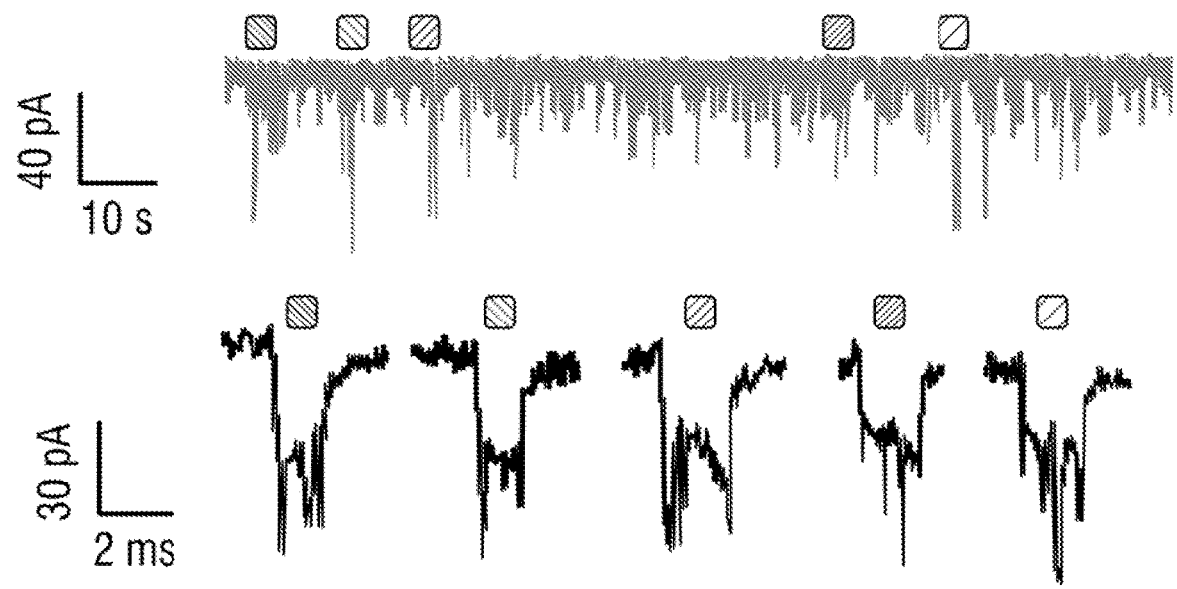
Figure 5C:
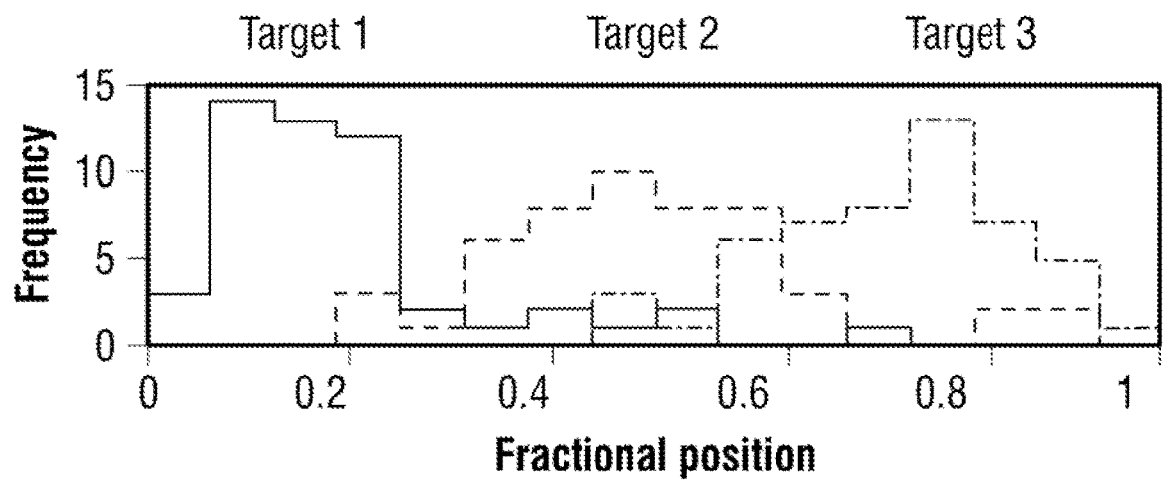
Figure 5D:
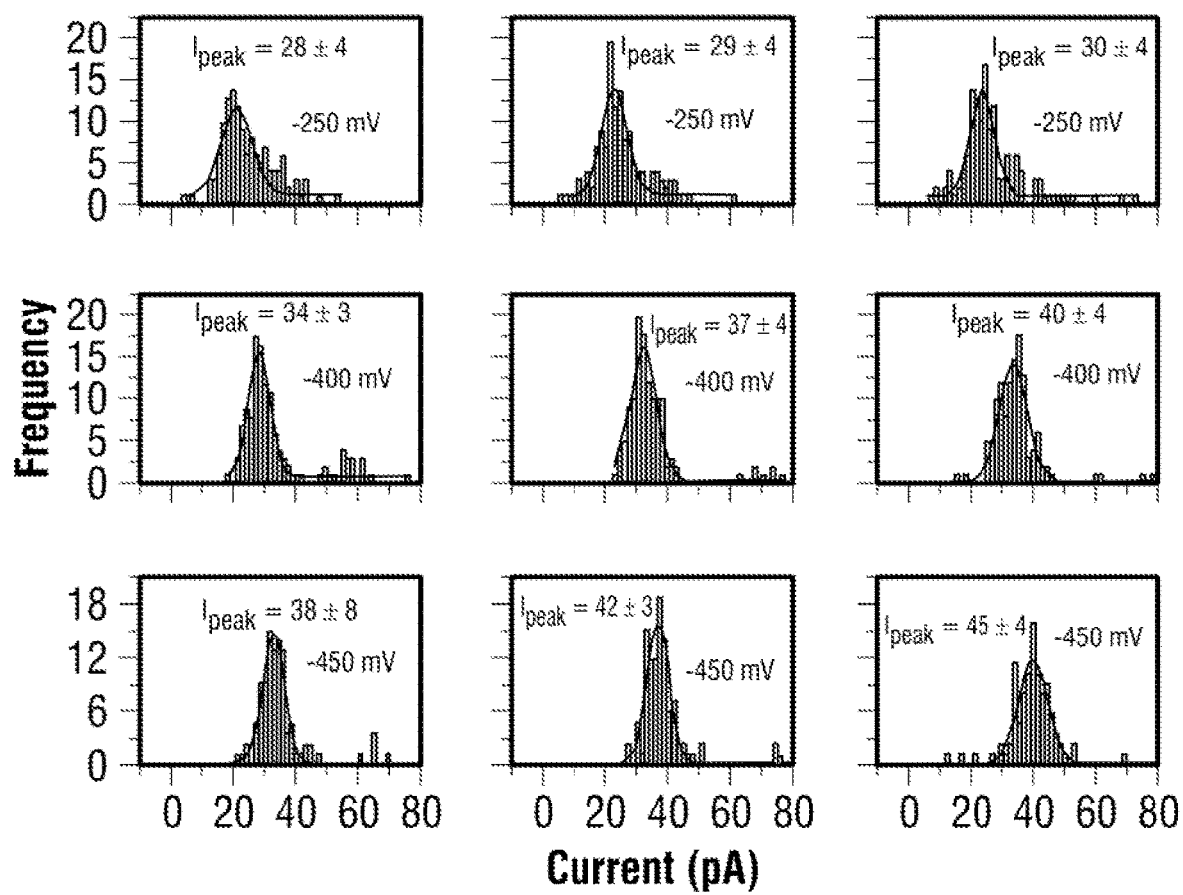

In order to show that the present approach can multiplex as well as differentiate different sizes of proteins within the dsDNA level, the following experiments were carried out. A larger protein target acetylcholinesterase (AchE) was chosen as it can easily differentiate the blockade level for ease of differentiating the blockade level. AchE (M.W. of 280 kDa and pI of 5) and TBA sequence were attached to the 3' and 5' termini of the DNA molecule, as shown in FIG. 4A. The DNA aptamer have a high binding affinity towards the AchE ($K_d$=14+1 pM)[39] and is not affected by low ionic strength (~20 mM)[40] in solution which makes it ideally suited for the nanopore experiment. A typical ionic current trace and expanded version of translocation events for thrombin binding to the TBA and acetylcholinesterase binding to the DNA aptamer at −200 mV were shown in FIG. 4B. The translocation events clearly show two distinct peaks within the dsDNA level, one with smaller peak current (~22+12 pA) and the other with larger peak current (~78±17 pA) corresponding to Thrombin and AchE respectively. The larger peak current can be explained by the massive AchE trying to get through to the confined geometry of the nanopipette in a linear fashion. It should also be noted there were no translocation observed at −100 mV indicating higher electrophoretic force would be required in order to allow the molecule pass through as there is a possibility of electroosmotic force pulling the complex. We also able to differentiate and locate the two population of binding events, visibly showing equal amount of events binding to the specific probe at normalised fractional position 0.2 and 0.8 in FIG. 4C. A voltage dependent contour plot of the complex (two targets on the dsDNA) and the individual sub-peak analsyis for the two proteins at a range of applied potential (−180, −200, −250 and −300 mV) can be seen in FIG. 4D showing the increasing the voltage leading to very small decrease in dwell time and larger peak current due to more charge carriers on the analytes (AchE) compared to thrombin). The individual sub-peak current were determined via Gaussian fitting and plotted in FIG. 4E.

Voltage Dependent with 3 Targets

To confirm the approach of DNA/Aptamer probe complex detection, a −100 mV potential was applied to the nanopipette and observed translocation events with dwell time (3.14±0.82 ms) indicating there is little or almost no energy barrier for the complex to pass through to the pore. Experiments with three protein targets along the long dsDNA translocation through the nanopore were performed for a range of applied voltage (−100, −150, −180 and −200 mV), as shown in FIG. 3A. The average dwell time and peak current of the bound targets to the detection probe were summarised in FIG. 3B; it indicated increasing applied voltage lead to higher translocation velocities but only minimal decrease in dwell times as the predominate electrophoretic force exerted on the negatively charged dsDNA rather than individual bound targets in the electrolyte. The changes in dwell time were almost negligible as λ-DNA is the dominant molecule passing through the pore due to the counter ions from the DNA backbone. The amplitude of the dsDNA level increases as the number of targets increases and this can be explained by consequence of additional charge carriers on the aptamer probe resulting in an increased ionic current.

Analysis of 3 Targets Bound to the dsDNA

Figure 3D:
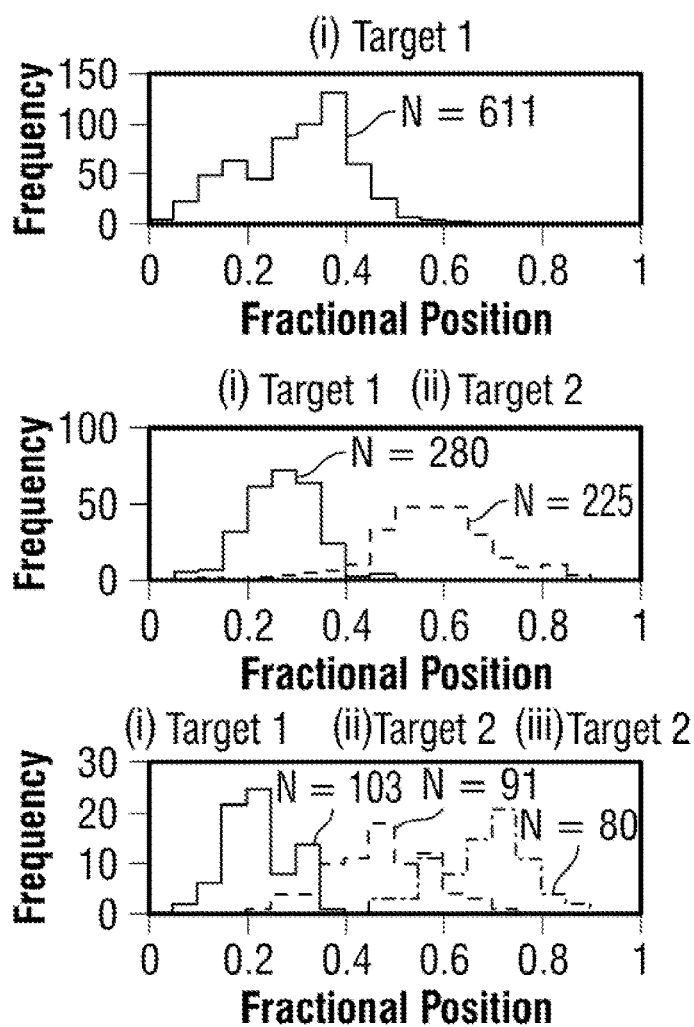

The present design allows easy and controlled positioning of any specific aptamer probe along the dsDNA. To demonstrate that nanopores can not only count the targets bound to its specific aptamer probes, but can also be used to accurately determine the location between different aptamer probes/targets along a DNA molecule the translocation times were normalized with 0 being defined as the translocation onset and 1 being defined as the end of the translocation. This is needed to take into account the differences in dwell time from translocation to translocation so that the fractional position of the bound protein to the DNA carrier can be determined, FIG. 3(c). This is carried out by dividing the times associated with the position of target 1, 2 and 3 ($\tau_1, \tau_2, \tau_3$) and dividing by the total translocation duration ($\tau_0$). As shown in FIG. 3(d), the translocations could be broken down into sub-populations consisting of 1, 2, and 3 proteins bound to the DNA carrier labelled target i, Different targets along the DNA carrier were able to identify, one of the binding domains is dependent on hybridising to the second domain and this could easily be overcome by ligation of the relevant sequences in future experiments. In all cases the fractional position corresponded well to the spacing between the different targets. Conversely, the same approach can in principle be used for the identification and positional mapping of specific sequence motifs in a carrier with unknown sequence.

Additional Data on Fluorescence Correlation Spectroscopy (FCS)

Overview

Data on FCS to support the method of detecting one or more analytes on the same DNA carrier. The carrier nucleic acid/aptamer/analyte complex was hereby detected by both electrical (nanopore) and/or optical (FCS).

Method

The aptamer sequences comprise a single stranded portion complementary to the DNA carrier via hybridization, with the other end of the aptamer sequence biotinylated. The complex was then incubated with protein target (in this case streptavidin), which has a fluorophore (Atto 488), enabling optical protein detection. Although the below example only showing single protein detection, the method enable multiplexing by implementing specific sequences along the DNA carrier.

Results

Figure 9A:
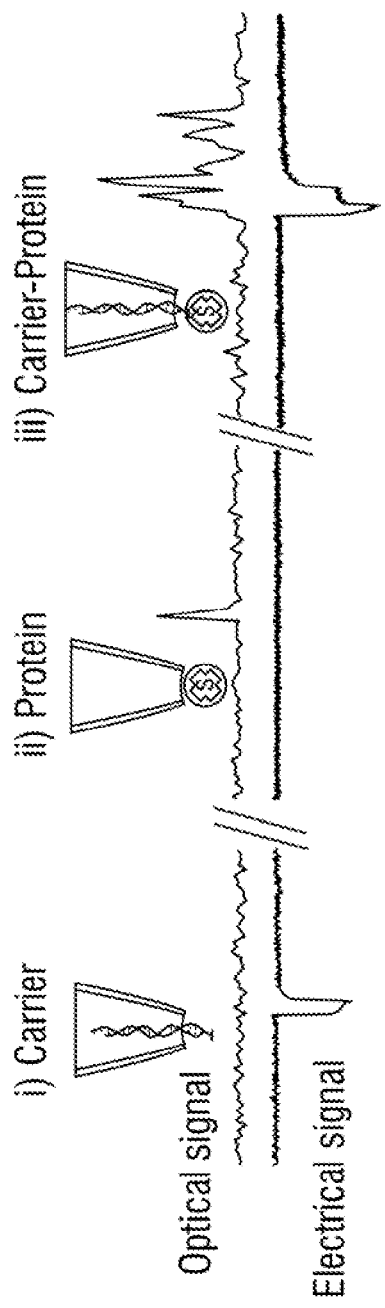
Figure 9B:
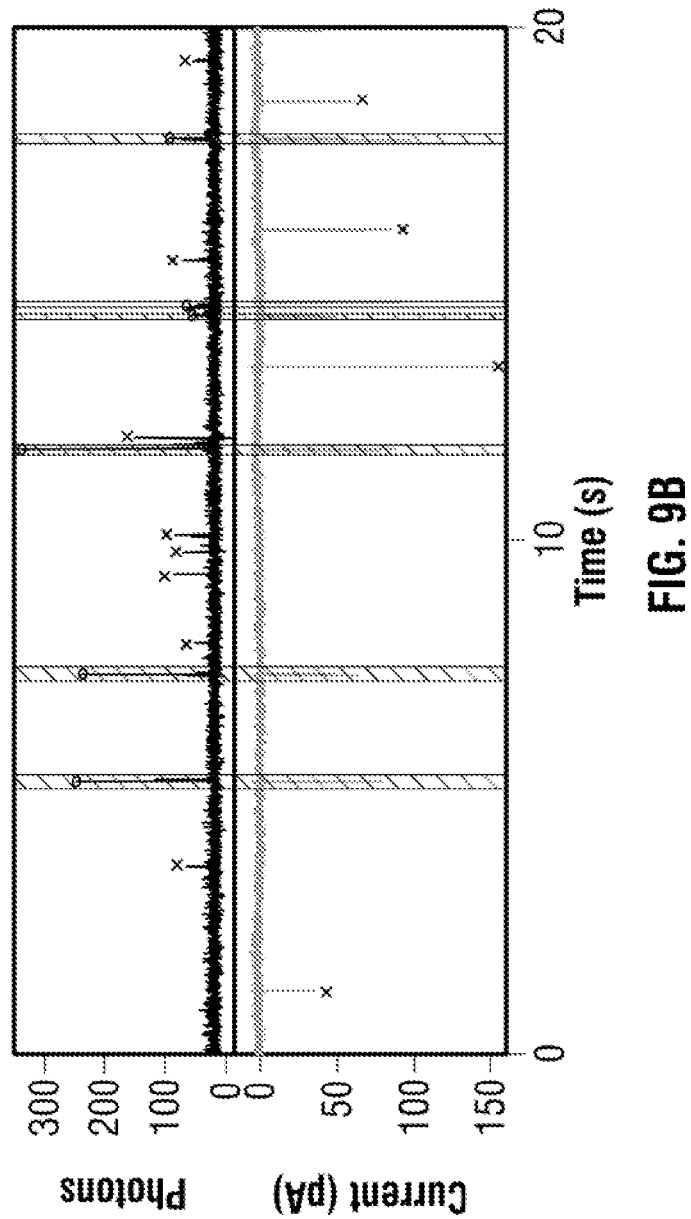
Figure 10A:
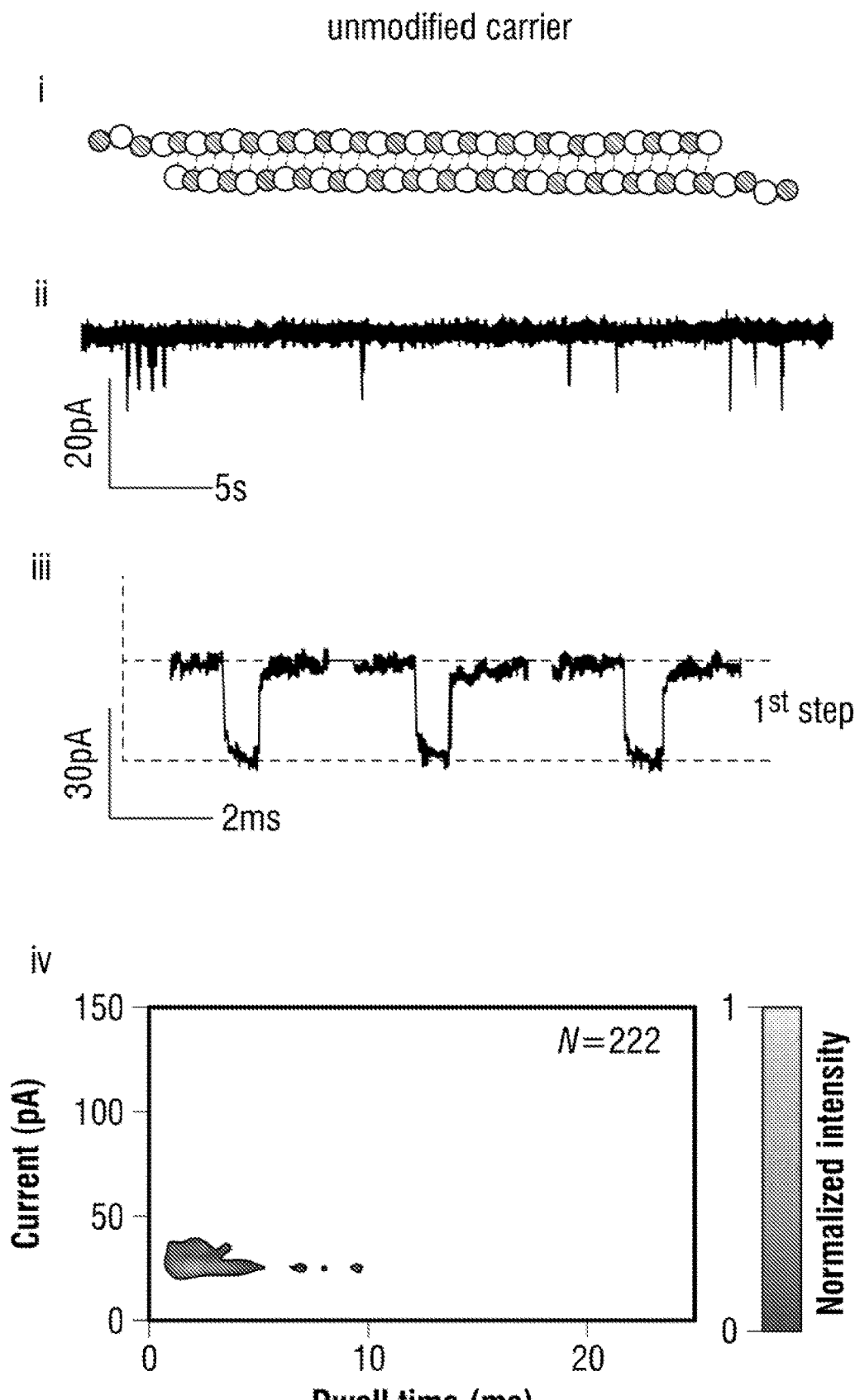
Figure 10B:
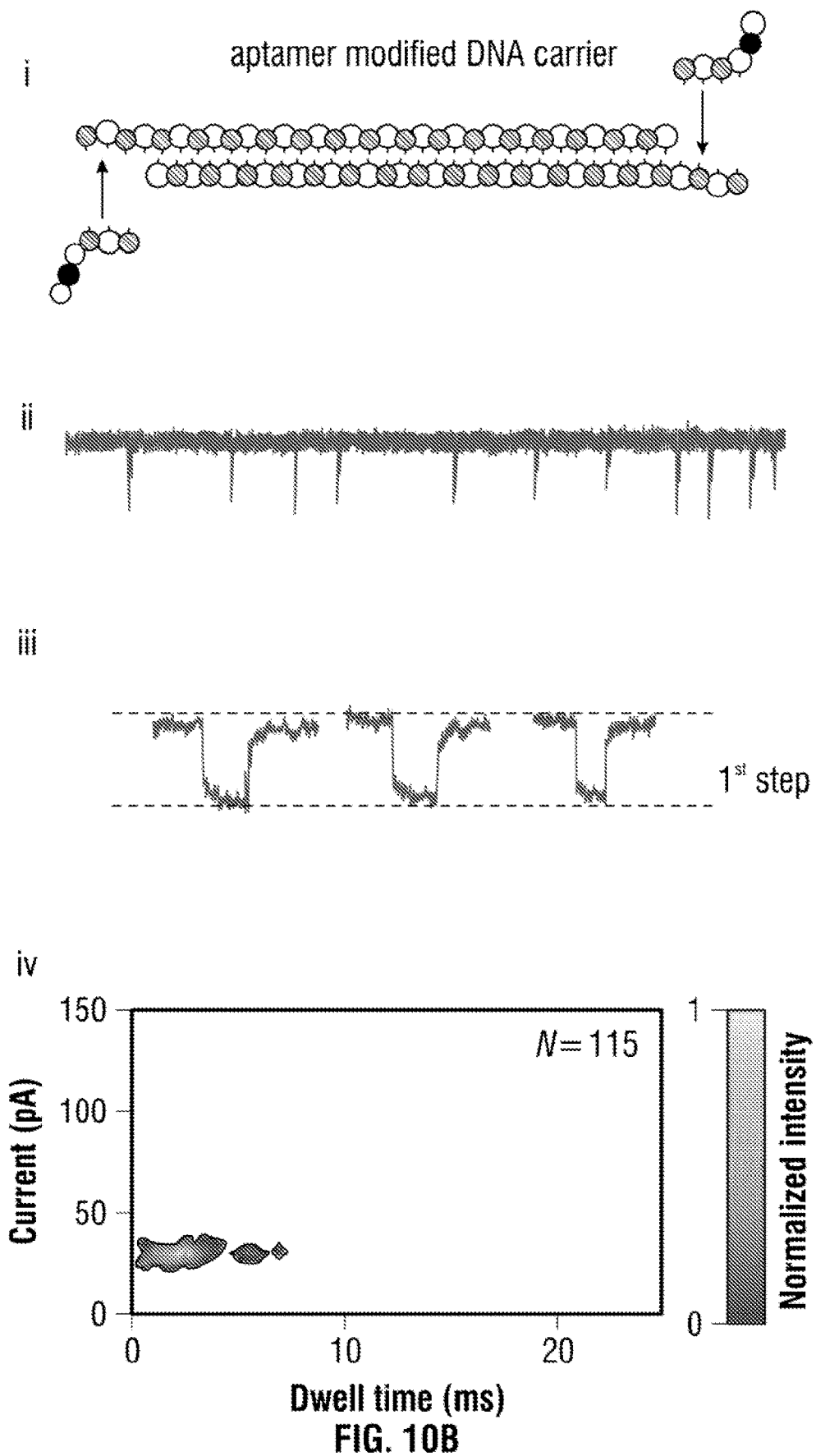
Figure 10C:
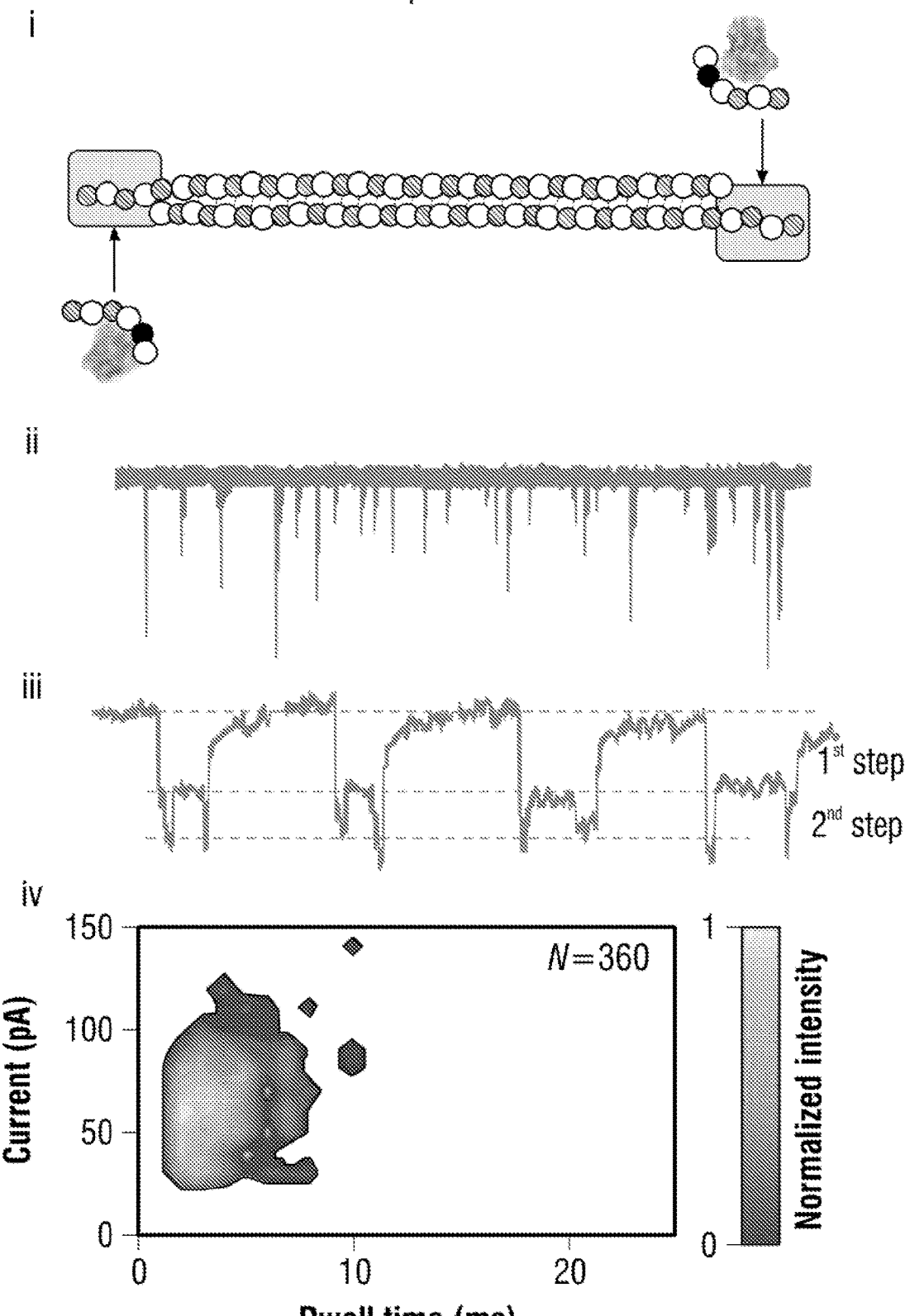
Figure 10D:
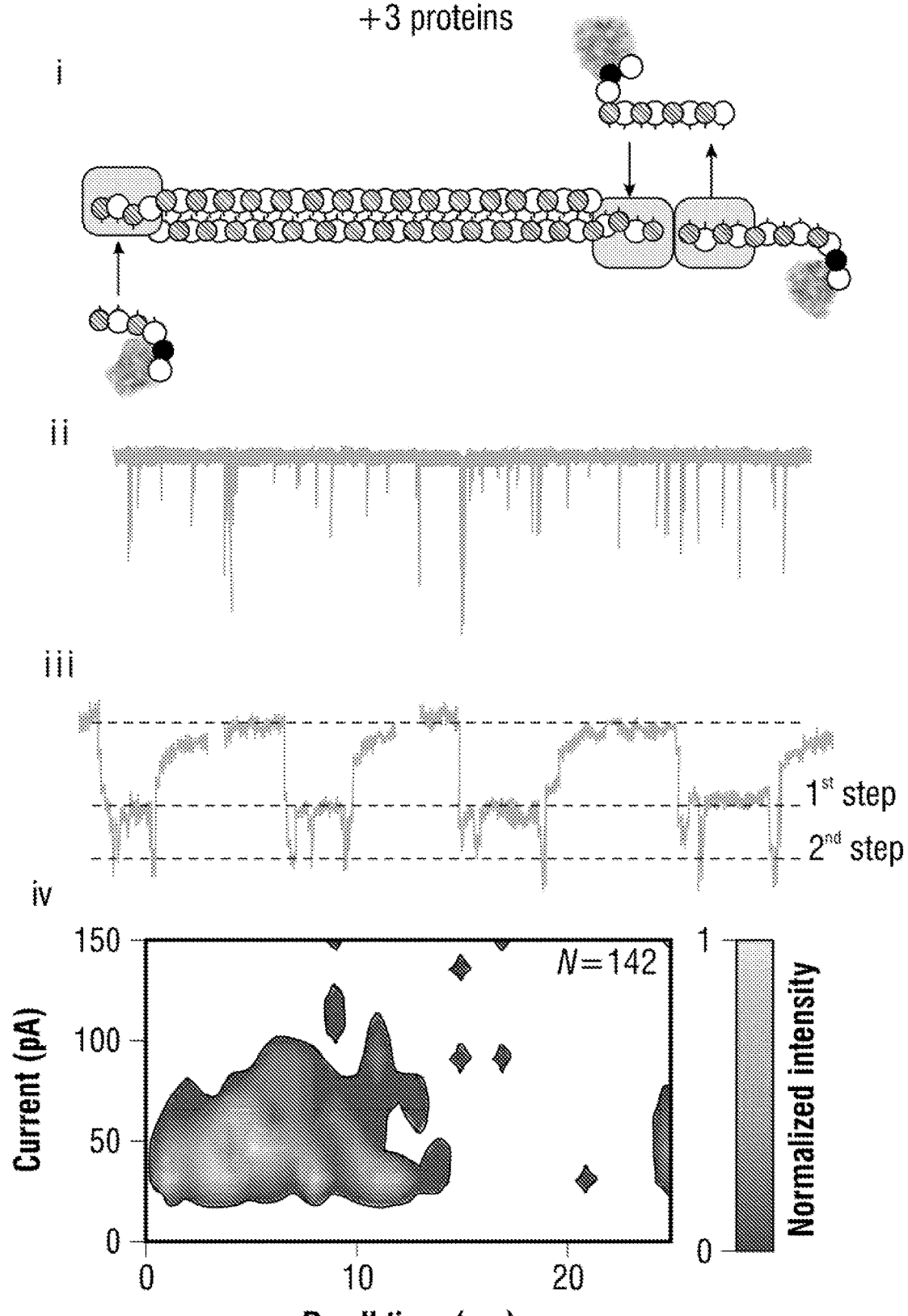
Figure 11A:
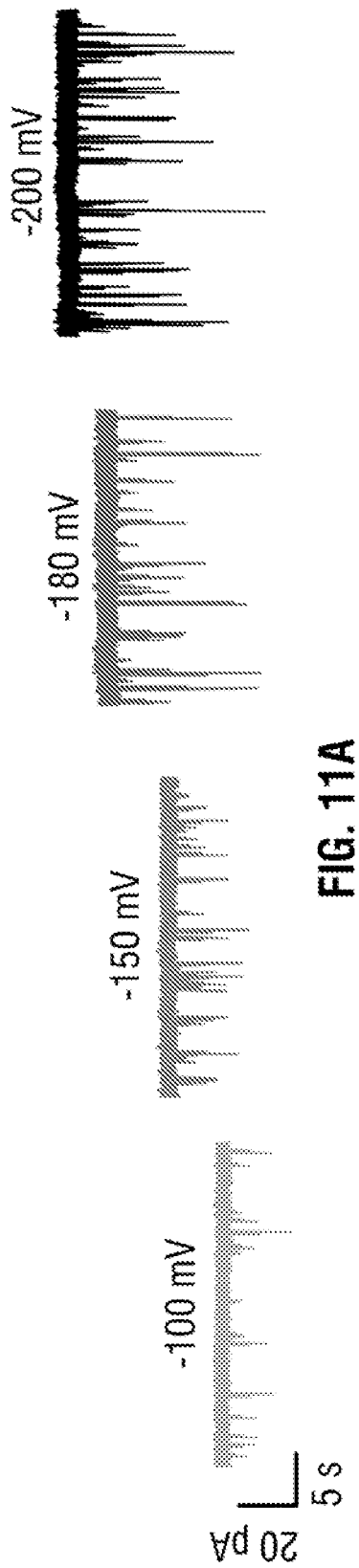
Figure 11B:
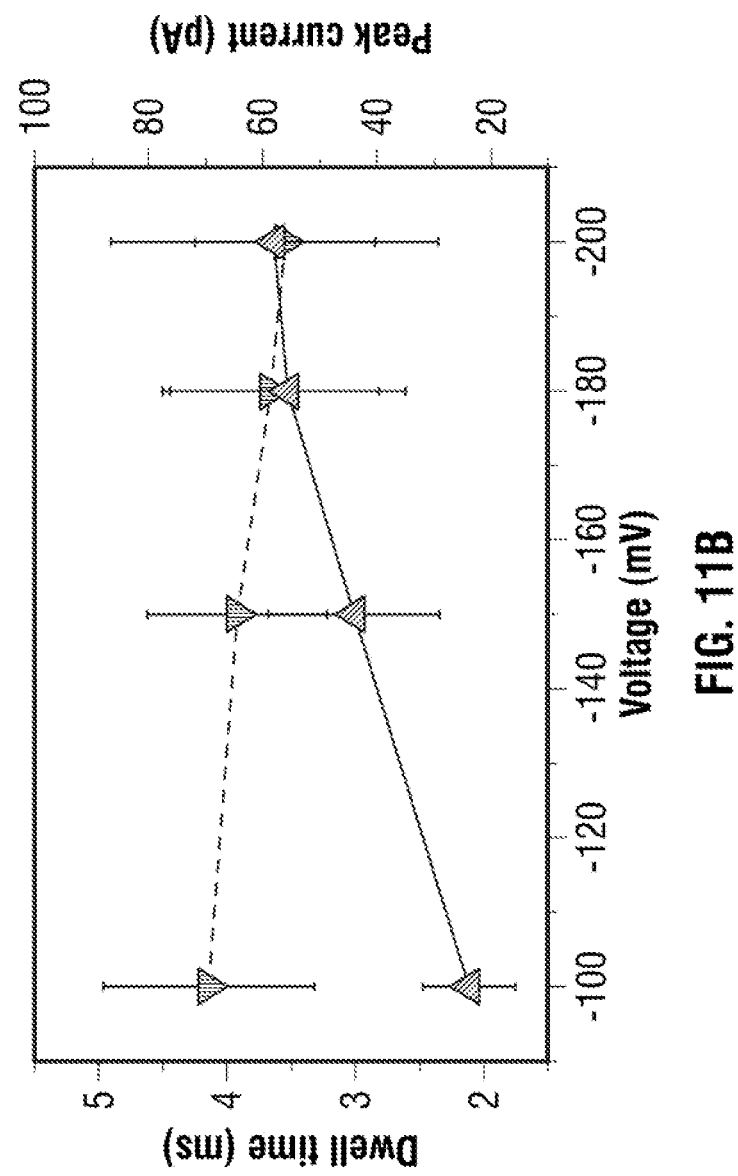
Figure 11C:
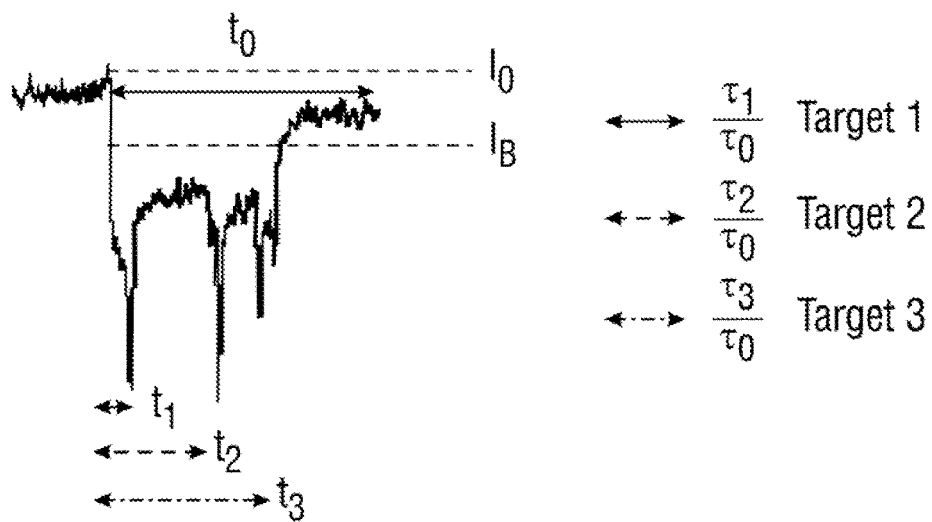
Figure 11D:
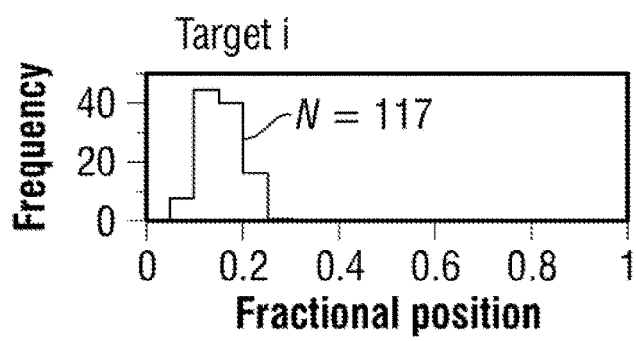
Figure 11D:
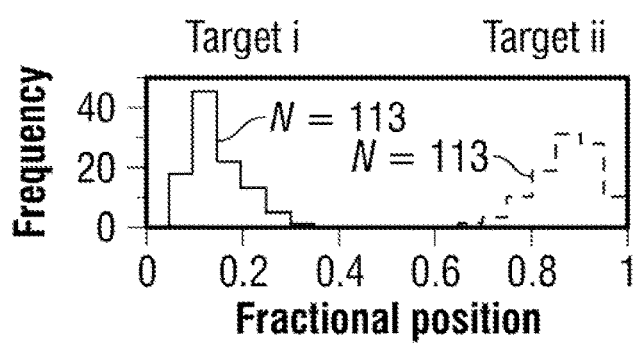
Figure 11D:
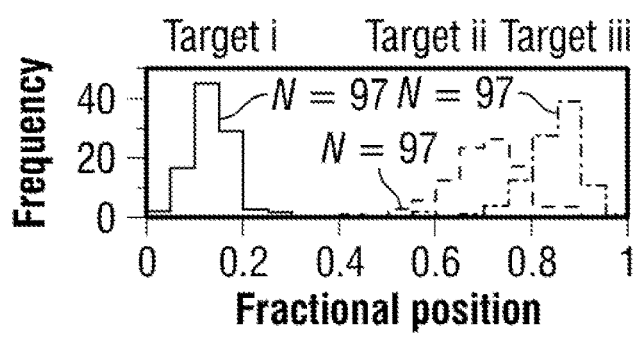
Figure 12A:
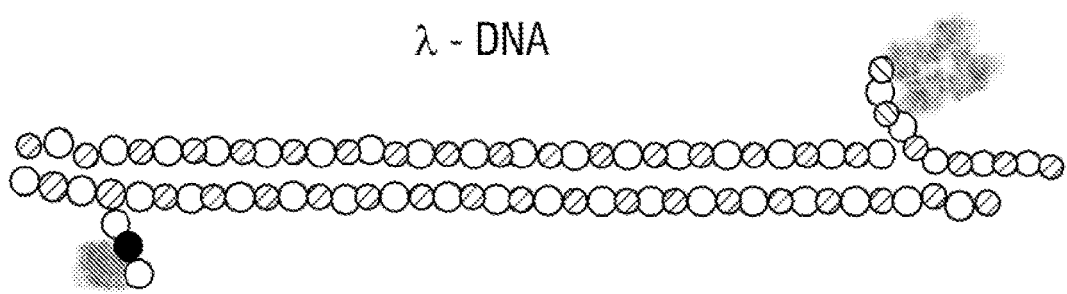
Figure 12B:
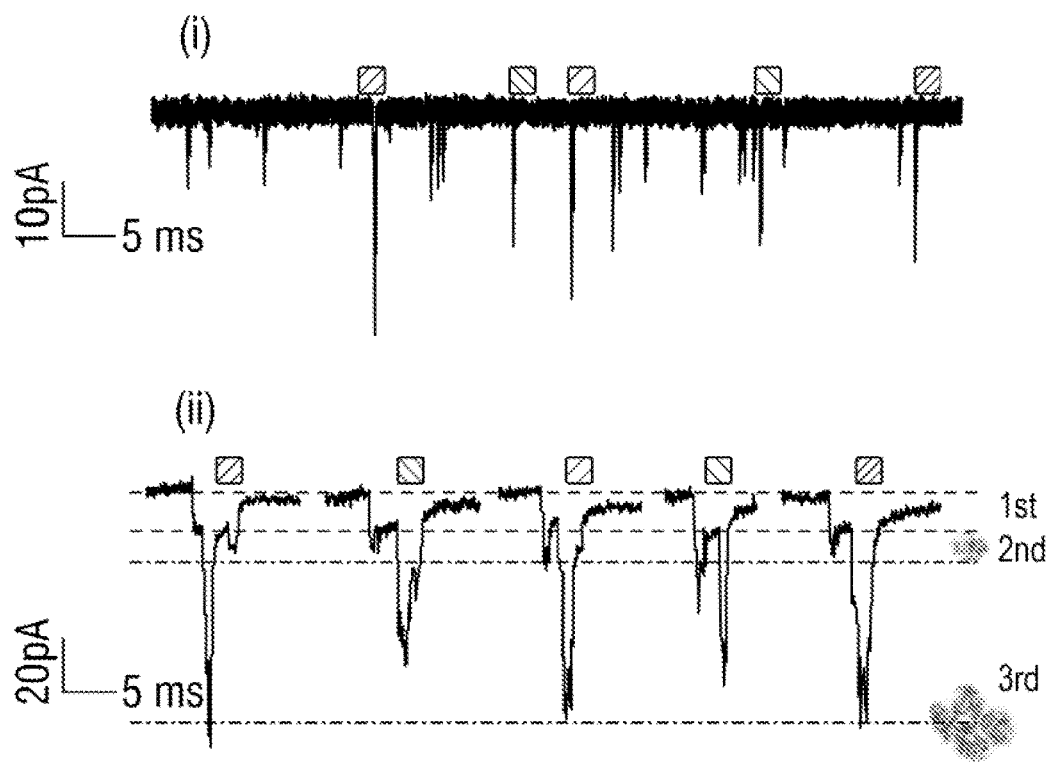
Figure 12C:
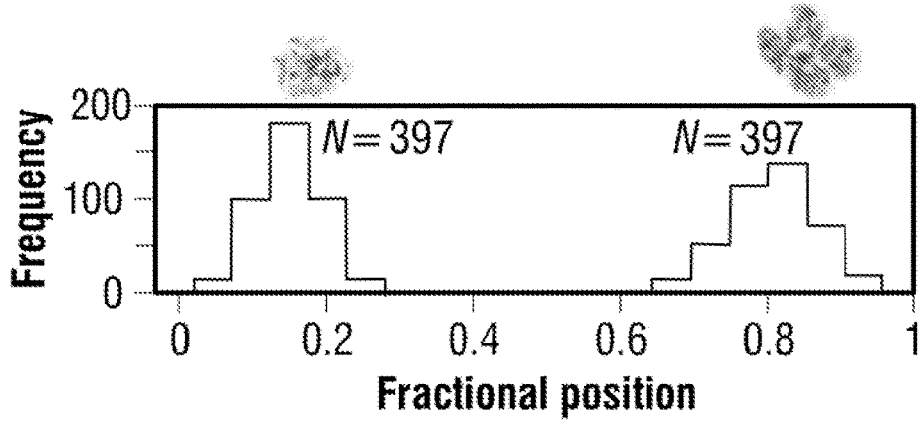
Figure 12D:
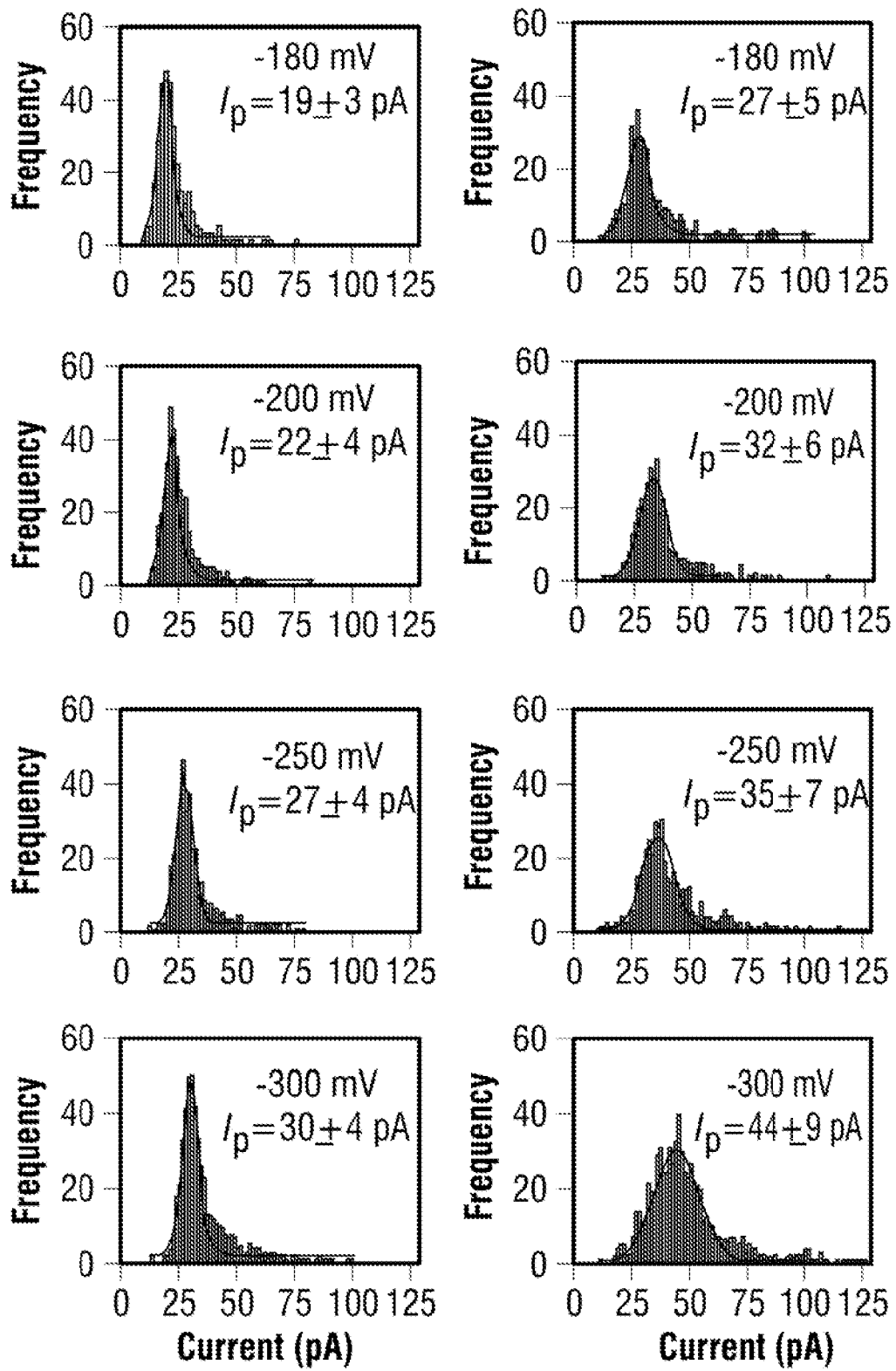
Figure 12E:
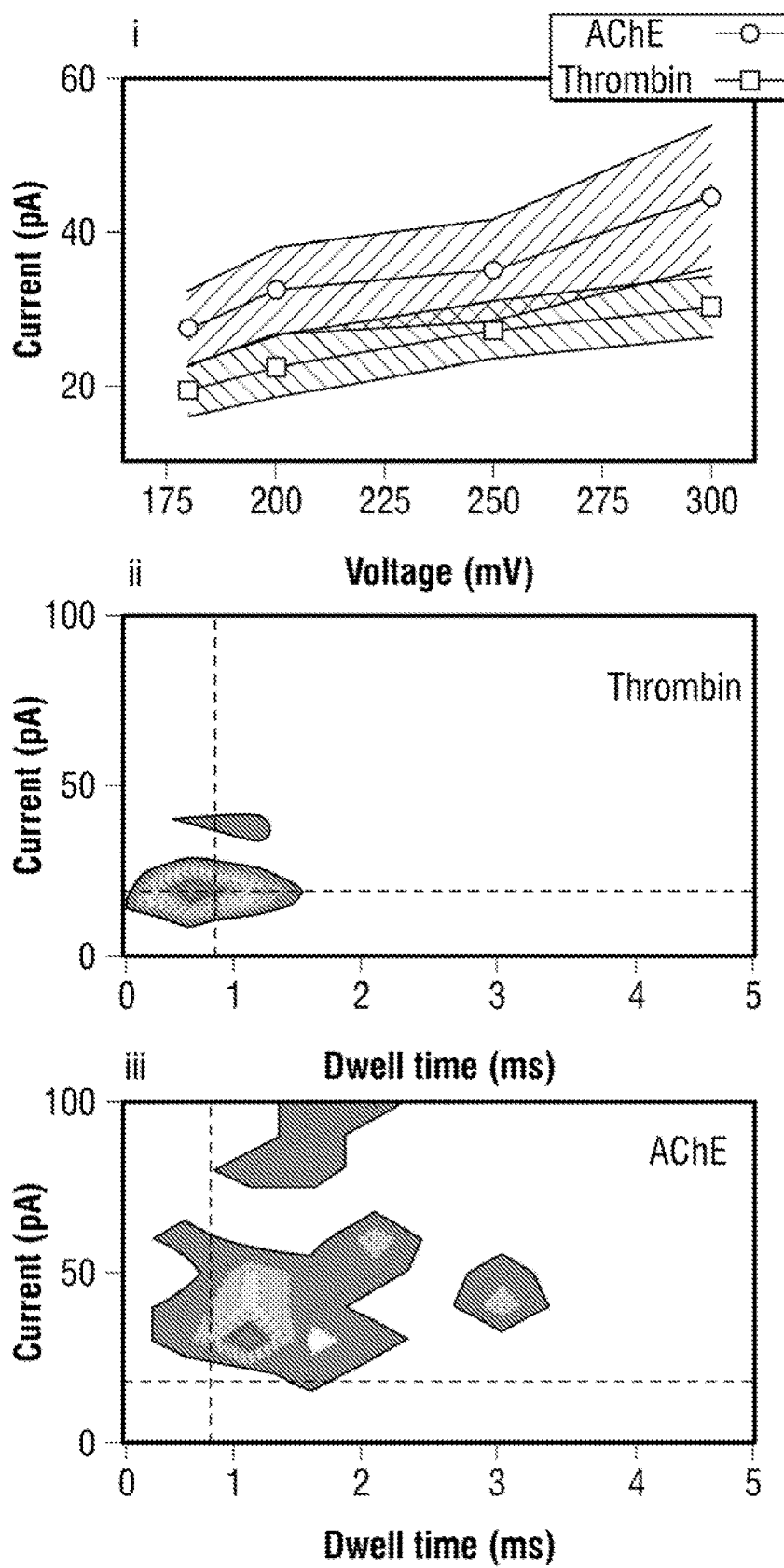
Figure 13A:
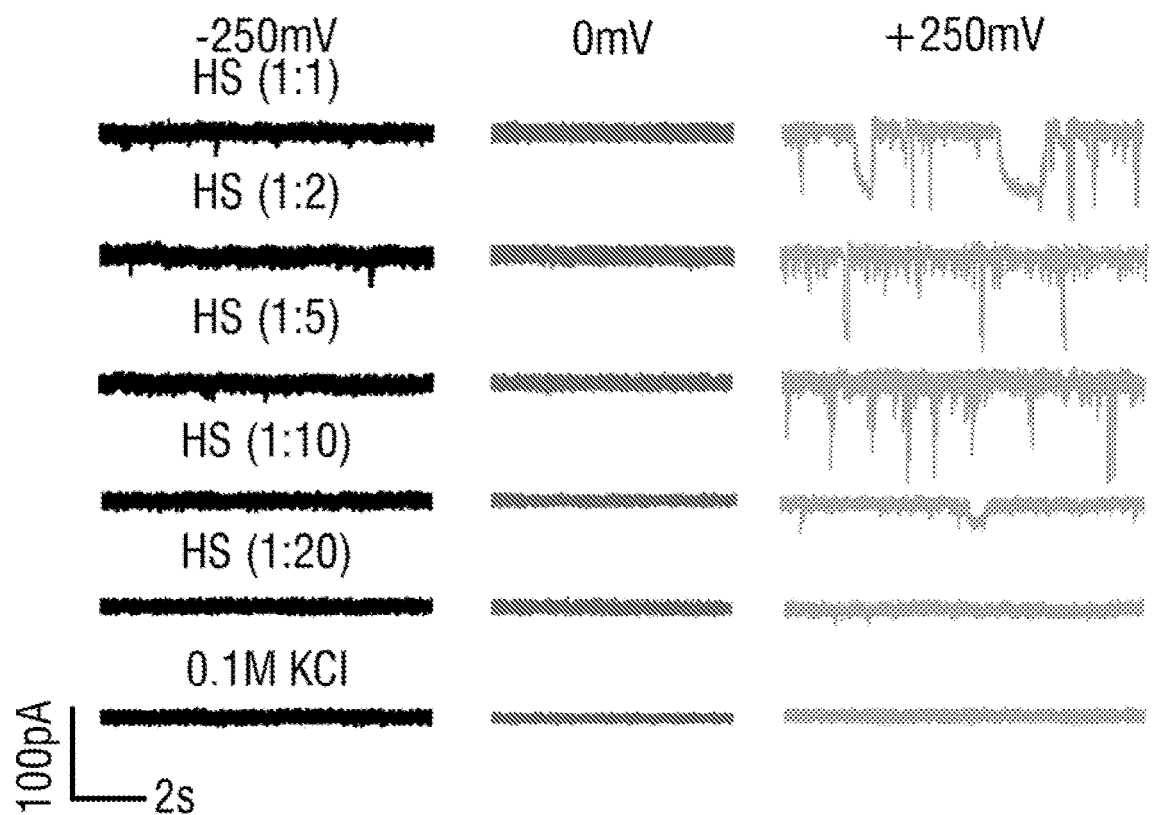
Figure 13B:
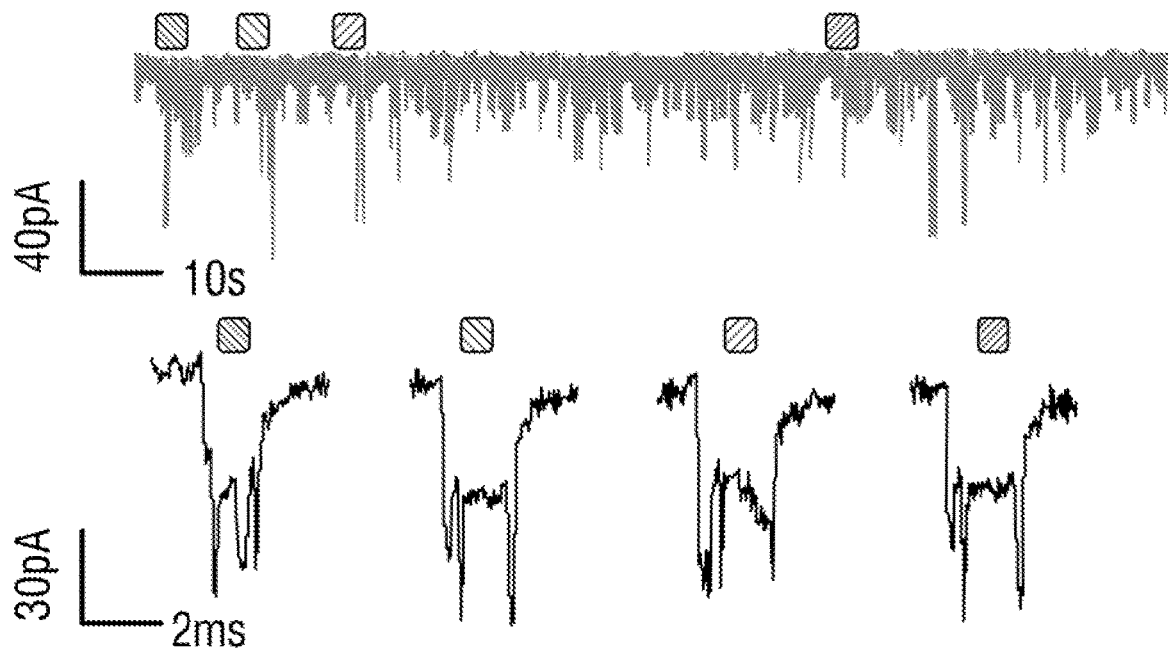
Figure 13C:
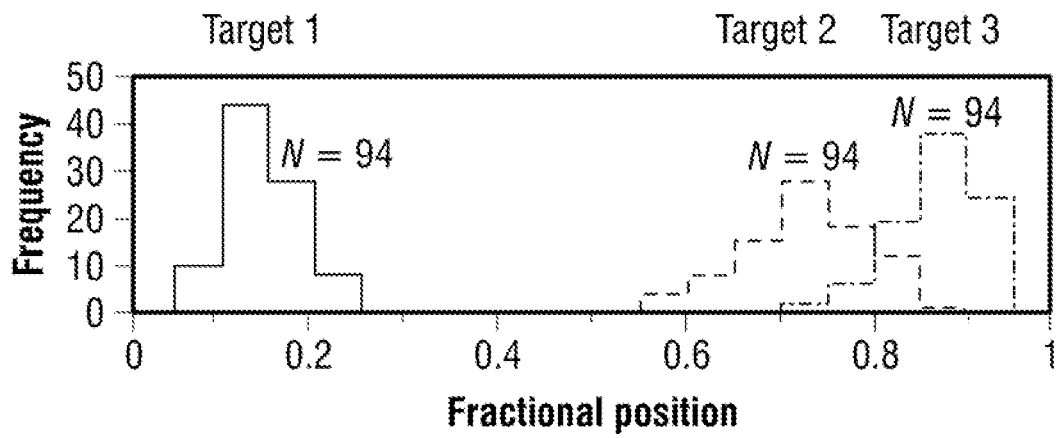
Figure 13D:
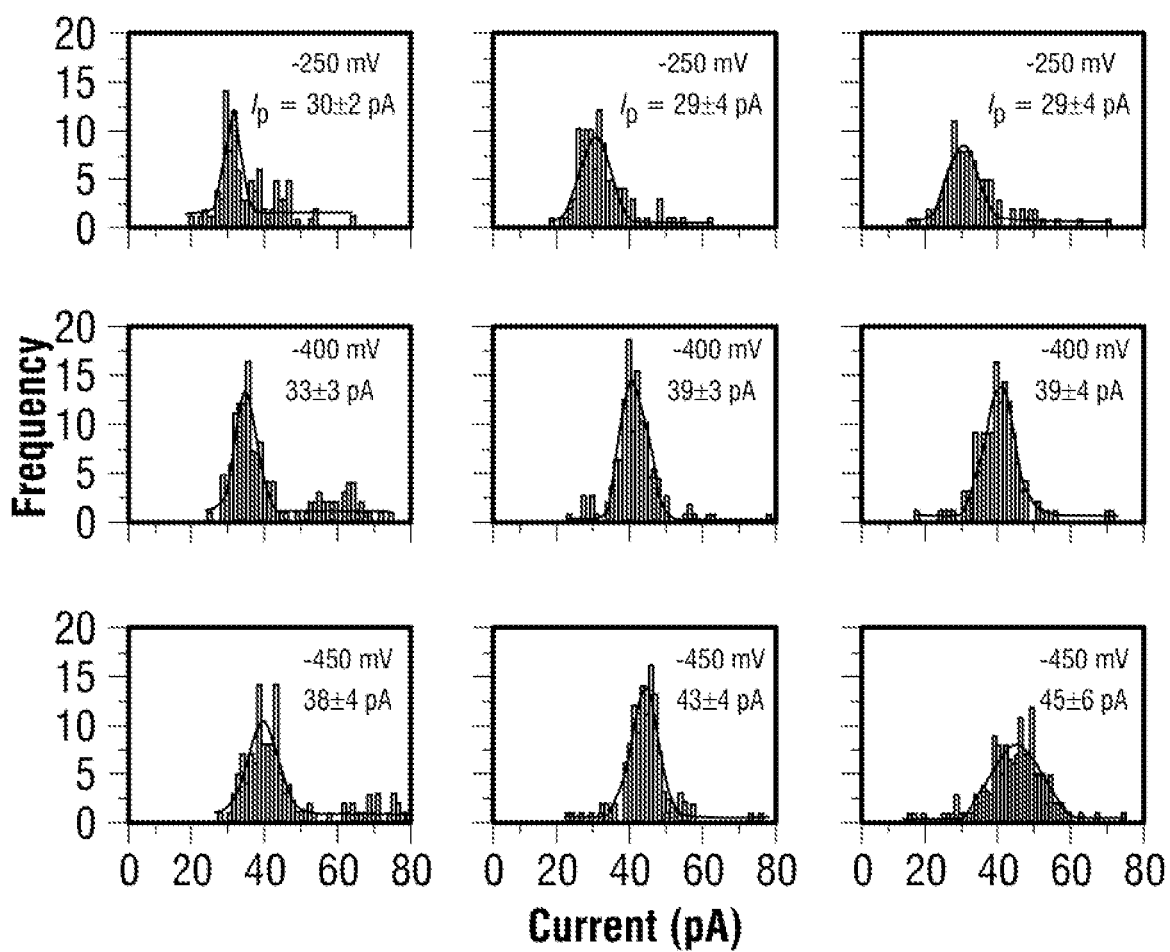

FIG. 9 shows the results of this validation work. Optical detection of the carrier/aptamer/analyte complex. In FIG. 9a, the three different signals observed due to carrier only, protein only and carrier-protein complex can be seen. In FIG. 9b typical traces from both optical and electrical signals are shown, with synchronized detection visible on several occasions. This work demonstrates that simultaneous electrical and optical detection is possible.

Additional Experimentation

Further control experiments were carried out as demonstrated in FIGS. 10, 15, 18, 20, 22 and 23. The data from FIGS. 10, 11, 12, 13 and 22 were further re-analysed, including in light of further control experiments carried out. Results are shown in FIGS. 14 to 26. The methods were carried out as set out above.

The results show that specific location of the protein bound to the corresponding aptamers produce unique ionic current signatures which facilitates accurate target recognition. This approach allows the differentiation of individual protein sizes via characteristic changes in the sub-peak current. Furthermore, it is shown that by using aptamer modified DNA carriers it is possible to perform multiplex single-molecule protein screening in human serum at ultra-low concentrations.

Conclusion

In summary, there is described herein a fully flexible yet efficient sensing method able to selectively detect multiple proteins via the grafting of the aptamer sequence recognition in solid-state nanopore system. The method has accurately demonstrate differentiation of different protein sizes and the precise location of targets binding to the detection probes as seen by the multiple sub-level signatures obtained within the DNA carrier. In comparison to conventional immunoassays or existing multiplexed nanopore method[29-31], the platform has been able to successfully isolate and identify targets without the need for repeated wash steps, expensive oligomers modification or using high reported concentration of incubated antibodies, hence significantly reducing the operation time and the cost. Aptamers are small, highly negatively charged and can be engineered to enhance their target selectivity and binding affinity (from low nM to pM), allowing further reduction in non-specific binding analyte interactions as well as the prevention of pore clogging which commonly reported. The excellent selectivity and affinity of biosensor is particularly vital in diagnostics detecting and identifying rare biomolecules/diseases in clinical sample or other biological fluids. To date, majority of the nanopore studies only work with specific proteins incubating with their specific counterpart in buffer based electrolyte. This contrasts with the real scenario of detecting proteins in actual samples such as non-specific binding to background proteins, environmental/reagent contamination from sample collections. With this in mind, we have illustrated that our detection probes are highly selective and sensitive in buffer as well as unprocessed human serum. We were able to detect three targets according to the detection probe locations. The potential to extend these specific detection probes further on either 5' or 3' of λ-DNA could lead to even more binding domains, certainly provide a powerful, accurate and sensitive biosensor to detect>40 targets simultaneously.

It should be understood by the skilled person that the features of the various aspects and embodiments described herein can be combined with the features of the other various aspects and embodiments.

REFERENCES

1. Dekker, C., Solid-state nanopores. *Nature nanotechnology* 2007, 2, 209-215.
2. Miles, B. N.; Ivanov, A. P.; Wilson, K. A.; Dogan, F.; Japrung, D.; Edel, J. B., Single molecule sensing with solid-state nanopores: novel materials, methods, and applications. *Chemical Society reviews* 2013, 42 (1), 15-28.
3. Shi, W.; Friedman, A. K.; Baker, L. A., Nanopore Sensing. *Analytical chemistry* 2017, 89 (1), 157-188.
4. Howorka, S.; Siwy, Z., Nanopore analytics: sensing of single molecules. *Chemical Society reviews* 2009, 38 (8), 2360-2384.
5. Meller, A.; Nivon, L.; Branton, D., Voltage-Driven DNA Translocations through a Nanopore. *Physical Review Letters* 2001, 86 (15), 3435-3438.
6. Li, J.; Gershow, M.; Stein, D.; Brandin, E.; Golovchenko, J. A., DNA molecules and configurations in a solid-state nanopore microscope. *Nature materials* 2003, 2 (9), 611-5.
7. Storm, A. J.; Storm, C.; Chen, J.; Zandbergen, H.; Joanny, J.-F.; Dekker, C., Fast DNA Translocation through a Solid-State Nanopore. *Nano letters* 2005, 5 (7), 1193-1197.
8. John. J. Kasianowicz, E. B., Daniel Branton, and David W. Deamer, Characterization of individual polynucleotide molecules using a membrane channel. *PNAS* 1996, 93.
9. Plesa, C.; Kowalczyk, S. W.; Zinsmeester, R.; Grosberg, A. Y.; Rabin, Y.; Dekker, C., Fast translocation of proteins through solid state nanopores. *Nano letters* 2013, 13 (2), 658-63.
10. Li, W.; Bell, N. A. W.; Hernandez-Ainsa, S.; Thacker, V. V.; Thackray, A. M.; Bujdoso, R.; Keyser, U. F., Single Protein Molecule Detection by Glass Nanopores. *ACS Nano* 2013, 7 (5), 4129-4134.
11. Wanunu, M.; Dadosh, T.; Ray, V.; Jin, J.; McReynolds, L.; Drndic, M., Rapid electronic detection of probe-specific microRNAs using thin nanopore sensors. *Nature nanotechnology* 2010, 5 (11), 807-14.
12. Gu, L.-Q.; Braha, O.; Conlan, S.; Cheley, S.; Bayley, H., Stochastic sensing of organic analytes by a pore-forming protein containing a molecular adapter. *Nature* 1999, 398 (6729), 686-690.
13. Maglia, G.; Henricus, M.; Wyss, R.; Li, Q.; Cheley, S.; Bayley, H., DNA Strands from Denatured Duplexes are Translocated through Engineered Protein Nanopores at Alkaline pH. *Nano letters* 2009, 9 (11), 3831-3836.
14. Oukhaled, G.; Mathé, J.; Biance, A. L.; Bacri, L.; Betton, J. M.; Lairez, D.; Pelta, J.; Auvray, L., Unfolding of Proteins and Long Transient Conformations Detected by Single Nanopore Recording. *Physical Review Letters* 2007, 98 (15), 158101.
15. Rodriguez-Larrea, D.; Bayley, H., Multistep protein unfolding during nanopore translocation. *Nat Nano* 2013, 8 (4), 288-295.
16. Rosen, C. B.; Rodriguez-Larrea, D.; Bayley, H., Single-molecule site-specific detection of protein phosphorylation with a nanopore. *Nat Biotech* 2014, 32 (2), 179-181.
17. Nivala, J.; Marks, D. B.; Akeson, M., Unfoldase-mediated protein translocation through an alpha-hemolysin nanopore. *Nature biotechnology* 2013, 31 (3), 247-50.
18. Nivala, J.; Mulroney, L.; Li, G.; Schreiber, J.; Akeson, M., Discrimination among Protein Variants Using an Unfoldase-Coupled Nanopore. *ACS Nano* 2014.
19. A. J. Storm, J. H. C., X. S. Ling, H. W. Zandbergen and C. Dekker Fabrication of solid-state nanopores with single-nanometre precision. *Nature Mat* 2003, 2, 537-540.
20. Ayub, M.; Ivanov, A.; Hong, J.; Kuhn, P.; Instuli, E.; Edel, J. B.; Albrecht, T., Precise electrochemical fabrication of sub-20 nm solid-state nanopores for single-molecule biosensing. *Journal of physics. Condensed matter: an Institute of Physics journal* 2010, 22 (45), 454128.
21. Kowalczyk, S. W.; Hall, A. R.; Dekker, C., Detection of local protein structures along DNA using solid-state nanopores. *Nano letters* 2010, 10 (1), 324-8.
22. Spiering, A.; Getfert, S.; Sischka, A.; Reimann, P.; Anselmetti, D., Nanopore translocation dynamics of a single DNA-bound protein. *Nano letters* 2011, 11 (7), 2978-82.
23. Squires, A.; Atas, E.; Meller, A., Nanopore sensing of individual transcription factors bound to DNA. *Sci Rep* 2015, 5, 11643.

24. Smeets, R. M. M.; Kowalczyk, S. W.; Hall, A. R.; Dekker, N. H.; Dekker, C., Translocation of RecA-Coated Double-Stranded DNA through Solid-State Nanopores. *Nano letters* 2009, 9 (9), 3089-3095.
25. Erik C. Yusko, J. M. J., Sheereen Majd, Panchika Prangkio, Ryan C. Rollings, Jiali Li, Jerry Yang and Michael Mayer, Controlling protein translocation through nanopores with bio-inspired fluid walls. *Nature nanotechnology* 2011, 6, 253-260.
26. Yusko, E. C.; Bruhn, B. R.; Eggenberger, O. M.; Houghtaling, J.; Rollings, R. C.; Walsh, N. C.; Nandivada, S.; Pindrus, M.; Hall, A. R.; Sept, D.; Li, J.; Kalonia, D. S.; Mayer, M., Real-time shape approximation and fingerprinting of single proteins using a nanopore. *Nature nanotechnology* 2016.
27. Singer, A.; Wanunu, M.; Morrison, W.; Kuhn, H.; Frank-Kamenetskii, M.; Meller, A., Nanopore based sequence specific detection of duplex DNA for genomic profiling. *Nano letters* 2010, 10, 738-742.
28. Singer, A.; Rapireddy, S.; Ly, D. H.; Meller, A., Electronic barcoding of a viral gene at the single-molecule level. *Nano letters* 2012, 12 (3), 1722-8.
29. Bell, N. A.; Keyser, U. F., Specific protein detection using designed DNA carriers and nanopores. *Journal of the American Chemical Society* 2015, 137 (5), 2035-41.
30. Bell, N. A.; Keyser, U. F., Digitally encoded DNA nanostructures for multiplexed, single-molecule protein sensing with nanopores. *Nature nanotechnology* 2016, 11 (7), 645-51.
31. Kong, J.; Bell, N. A.; Keyser, U. F., Quantifying Nanomolar Protein Concentrations Using Designed DNA Carriers and Solid-State Nanopores. *Nano letters* 2016, 16 (6), 3557-62.
32. Tuerk, C.; Gold, L., Systematic evolution of ligands by exponential enrichment: RNA ligands to bacteriophage T4 DNA polymerase. *Science (New York, N.Y.)* 1990, 249 (4968), 505-510.
33. Ellington, A. D.; Szostak, J. W., In vitro selection of RNA molecules that bind specific ligands. *Nature* 1990, 346 (6287), 818-822.
34. Smith, J. E.; Medley, C. D.; Tang, Z.; Shangguan, D.; Lofton, C.; Tan, W., Aptamer-conjugated nanoparticles for the collection and detection of multiple cancer cells. *Analytical chemistry* 2007, 79 (8), 3075-82.
35. Kelly, J. A.; Feigon, J.; Yeates, T. O., Reconciliation of the X-ray and NMR Structures of the Thrombin-Binding Aptamer d(GGTTGGTGTGGTTGG). *Journal of Molecular Biology* 1996, 256 (3), 417-422.
36. Russo Krauss, I.; Merlino, A.; Giancola, C.; Randazzo, A.; Mazzarella, L.; Sica, F., Thrombin-aptamer recognition: a revealed ambiguity. *Nucleic acids research* 2011.
37. Pasternak, A.; Hernandez, F. J.; Rasmussen, L. M.; Vester, B.; Wengel, J., Improved thrombin binding aptamer by incorporation of a single unlocked nucleic acid monomer. *Nucleic acids research* 2011, 39 (3), 1155-64.
38. Russo Krauss, I.; Merlino, A.; Randazzo, A.; Novellino, E.; Mazzarella, L.; Sica, F., High-resolution structures of two complexes between thrombin and thrombin-binding aptamer shed light on the role of cations in the aptamer inhibitory activity. *Nucleic acids research* 2012, 40 (16), 8119-8128.
39. Le, T. T.; Chumphukam, O.; Cass, A. E. G., Determination of minimal sequence for binding of an aptamer. A comparison of truncation and hybridization inhibition methods. *RSC Adv.* 2014, 4 (88), 47227-47233.
40. Chumphukam, O.; Le, T. T.; Cass, A. E., High efficiency acetylcholinesterase immobilization on DNA aptamer modified surfaces. *Molecules* 2014, 19 (4), 4986-96.

The invention claimed is:

1. A method of detecting one or more analytes in a sample, the method comprising:
   a. providing a carrier nucleic acid molecule with at least one single-stranded region;
   b. providing one or more aptamers specific for the analyte, wherein the aptamers additionally comprise a single-stranded portion complementary to at least one single-stranded region on the carrier nucleic acid;
   c. contacting the carrier nucleic acid and one or more aptamers with the sample, forming a carrier nucleic acid/aptamer/analyte complex;
   d. detecting the presence of the carrier nucleic acid/aptamer/analyte complex by voltage driven translocation through a nanopore.

2. The method of claim 1, wherein multiple aptamers specific for different analytes are provided, each analyte-specific aptamer having a single-stranded portion complementary to a different single-stranded region on the carrier nucleic acid.

3. The method of claim 1, wherein at least one aptamer comprises a single-stranded portion partially complementary to single-stranded portion of the carrier nucleic acid and partially complementary to the single-stranded portion of another aptamer.

4. The method of claim 1, wherein a change in nanopore conductance versus control indicates the presence of an analyte.

5. The method of claim 4, wherein the location of the change in nanopore conductance versus control in the time frame of translocation is indicative of the position of the aptamer along the carrier nucleic acid.

6. The method of claim 1, wherein the nanopore is located at the tip of a nanopipette.

7. The method of claim 1, wherein detection of the carrier nucleic acid/aptamer/analyte complex is by fluorescence detection.

8. The method of claim 1, wherein detection of the carrier nucleic acid/aptamer/analyte complex is by confocal microscopy.

9. The method of claim 1, wherein an additional analyte-specific binding molecule is contacted with the sample, forming a carrier nucleic acid/aptamer/analyte/analyte-specific binding molecule complex.

10. A method of detecting one or more analytes in a sample, the method comprising:
    a. providing a carrier nucleic acid molecule with at least one single-stranded region;
    b. providing one or more aptamers specific for the analyte, wherein the aptamers additionally comprise a single-stranded portion complementary to at least one single-stranded region on the carrier nucleic acid;
    c. providing a known quantity of the analyte conjugated to a high molecular weight label, forming a known quantity of carrier nucleic acid/aptamer/labelled-analyte complex;
    d. contacting the carrier nucleic acid/aptamer/labelled-analyte complex with the sample; and
    e. detecting the change of the presence of the carrier nucleic acid/aptamer/labelled-analyte complex by voltage driven translocation through a nanopore.

* * * * *

SEQUENCE LISTING

```
<160> NUMBER OF SEQ ID NOS: 9

<210> SEQ ID NO 1
<211> LENGTH: 15
<212> TYPE: DNA
<213> ORGANISM: artificial sequence
<220> FEATURE:
<223> OTHER INFORMATION: Thrombin binding aptamer (TBA) 15-mer

<400> SEQUENCE: 1
ggttggtgtg gttgg                                                     15

<210> SEQ ID NO 2
<211> LENGTH: 12
<212> TYPE: DNA
<213> ORGANISM: artificial sequence
<220> FEATURE:
<223> OTHER INFORMATION: 5 terminus 12 base oligonucleotide overhang

<400> SEQUENCE: 2
gggcggcgac ct                                                        12

<210> SEQ ID NO 3
<211> LENGTH: 12
<212> TYPE: DNA
<213> ORGANISM: artificial sequence
<220> FEATURE:
<223> OTHER INFORMATION: 3 terminus 12 base oligonucleotide overhang

<400> SEQUENCE: 3
```
aggtcgccgc cc                                                    12

<210> SEQ ID NO 4
<211> LENGTH: 51
<212> TYPE: DNA
<213> ORGANISM: artificial sequence
<220> FEATURE:
<223> OTHER INFORMATION: lambda DNA unspecific probe

<400> SEQUENCE: 4
ggttgactgt agctctggca gacgtagtgt gaaggtaccg ggcggcgacc t          51

<210> SEQ ID NO 5
<211> LENGTH: 27
<212> TYPE: DNA
<213> ORGANISM: artificial sequence
<220> FEATURE:
<223> OTHER INFORMATION: Target i (27 bases)

<400> SEQUENCE: 5
ggttggtgtg gttggaggtc gccgccc                                    27

<210> SEQ ID NO 6
<211> LENGTH: 51
<212> TYPE: DNA
<213> ORGANISM: artificial sequence
<220> FEATURE:
<223> OTHER INFORMATION: Target ii (51 bases) & a3 aptamer &
      complementary sequence 4

<400> SEQUENCE: 6
ggttggtgtg gttgggggcg gcgacctaag gtgtcgtgcg taagttttta a          51

<210> SEQ ID NO 7
<211> LENGTH: 69
<212> TYPE: DNA
<213> ORGANISM: artificial sequence
<220> FEATURE:
<223> OTHER INFORMATION: Target iii (69 bases) & a2 aptamer &
      complementary sequence 3

<400> SEQUENCE: 7
ggttggtgtg gttggttttt ttttgtcttt ttttttttc tgttttaaa aacttacgca   60 cgacacctt                                                        69

<210> SEQ ID NO 8
<211> LENGTH: 75
<212> TYPE: DNA
<213> ORGANISM: artificial sequence
<220> FEATURE:
<223> OTHER INFORMATION: Target ii (75 bases, AChE) & b1 aptamer &
      complementary sequence 2

<400> SEQUENCE: 8
ggttgactgt agctctggca gacgtagtgt gaaggtaccg ggcggcgacc taaggtgtcg   60
tgcgtaagtt tttaa                                                 75

<210> SEQ ID NO 9
<211> LENGTH: 27
<212> TYPE: DNA
<213> ORGANISM: artificial sequence

```
<220> FEATURE:
<223> OTHER INFORMATION: a1 aptamer & complementary sequence 1

<400> SEQUENCE: 9
ggttggtgtg gttggaggtc gccgccc                                              27
```